US008563283B2

(12) United States Patent
Martinez Jimenez et al.

(10) Patent No.: US 8,563,283 B2
(45) Date of Patent: Oct. 22, 2013

(54) **STRAINS OF *ESCHERICHIA COLI* MODIFIED BY METABOLIC ENGINEERING TO PRODUCE CHEMICAL COMPOUNDS FROM HYDROLYZED LIGNOCELLULOSE, PENTOSES, HEXOSES AND OTHER CARBON SOURCES**

(75) Inventors: Alfredo Martinez Jimenez, Morelos (MX); Guillermo Gosset Lagarda, Morelos (MX); Georgina Teresa Hernandez Chavez, Morelos (MX); Gerardo Huerta Beristain, Guerrero (MX); Berenice Trujillo Martinez, Morelos (MX); Jose Utrilla Carreri, Chiapas (MX)

(73) Assignee: Universidad Nacional Autonoma de Mexico, Mexico City (MX)

( * ) Notice: Subject to any disclaimer, the term of this patent is extended or adjusted under 35 U.S.C. 154(b) by 0 days.

(21) Appl. No.: 13/388,555

(22) PCT Filed: Aug. 6, 2010

(86) PCT No.: PCT/MX2010/000075
§ 371 (c)(1),
(2), (4) Date: Feb. 2, 2012

(87) PCT Pub. No.: WO2011/016706
PCT Pub. Date: Feb. 10, 2011

(65) Prior Publication Data
US 2012/0219997 A1     Aug. 30, 2012

(30) Foreign Application Priority Data
Aug. 7, 2009  (MX) .................. MX/A/2009/008453

(51) Int. Cl.
*C12P 7/06*    (2006.01)
*C12P 7/56*    (2006.01)
*C12N 1/22*    (2006.01)

(52) U.S. Cl.
USPC .................. 435/161; 435/139; 435/252.33

(58) Field of Classification Search
None
See application file for complete search history.

(56) References Cited

PUBLICATIONS

Dien et al., "Recombinant *Escherichia coli* engineered for production of L-lactic acid from hexose and pentose sugars", J. Ind. Microbiol. Biotechnol. 27:259-264, 2001.*

Utrilla et al., "Engineering and adaptive evolution of *Escherichia coli* for D-lactate fermentation reveals GatC as a xylose transporter", Metabolic Engineer. 14:469-476, 2012.*

Lindsay et al., "Improved strains of recombinant *Escherichia coli* for ethanol production from sugar mixtures", Appl. Microbiol. Biotechnol. 43:70-75, 1995.*

Metabolic Engineering VII: Health and Sustainability, Sep. 14-19, 2008, "The ATP Limitation in a Pyruvate Formate Lyase Mutant of *Escherichia coli* Increases Glycolytic Flux to D-Lactate", Poster 16, p. 134.

SIM Annual Meeting Program & Abstracts, Aug. 10-14, 2008, Poster Abstracts, p. 48.

L. J. Leal et al., Ingeniería Metabólica de *Escherichia coli* para producir L-lactato. XIII Congreso Nacional de Biotecnología y Bioingeniería y VII Simposio Internacional de Producción de Alcoholes y Levaduras. Acapulco, Jun. 21-26, 2009.

J. Utrilla et al., ATP limitation in a pyruvate formate lyase mutant of *Escherichia coli* MG1655 increases glycolytic flux to D-lactate. Journal of Industrial Microbiology & Biotechnology, Aug. 2009, vol. 36, No. 8, pp. 1057-1062.

H. Tao et al., Engineering a homo-ethanol pathway in *Escherichia coli*: increased glycolytic flux and levels of expression of glycolytic genes during xylose fermentation. Journal of Bacteriology, May 2001, vol. 183, No. 10, pp. 2979-2988.

A. Hasona et al., Pyruvate formate lyase and acetate kinase are essential for anaerobic growth of *Escherichia coli* on xylose. Journal of Bacteriology. Nov. 2004, vol. 186, No. 22, pp. 7593-7600.

R. Khankal et al., Rose of xylose transporters in xylitol production from engineered *Escherichia coli*. Journal of Biotechnology. Apr. 2008, vol. 134, No. 3-4, pp. 246-252.

M. Hibi et al., Improvement of NADPH-dependent bioconversion by transcriptome-based molecular breeding. Applied and Environmental Microbiology. Dec. 2007, vol. 73, No. 23, pp. 7657-7663.

* cited by examiner

*Primary Examiner* — David J Steadman
(74) *Attorney, Agent, or Firm* — Jacobson Holman PLLC

(57) ABSTRACT

The present invention refers to the new *Escherichia coli* strains denominated JU15, JU15A, LL26 and MS04 and their derivatives that produce metabolites, particularly D-lactate, L-lactate or ethanol, with high yield and selectivity from a wide variety of carbon sources, such as culture media with a high xylose content (as the main carbon source) and, in particular, media formulated with hydrolyzed vegetables, such as sugarcane bagasse, agave bagasse and fast-growing grasses, and a wide variety of agricultural and industrial wastes, such as whey or forestry wastes, celluloses, grasses, agave bagasse, paper wastes, shavings and sawdust, shrubs and generally any material derived from lignocellulose. These strains use the production of the metabolite of interest (especially D-lactate, L-lactate or ethanol) as the only way of regenerating the reducing power. The invention also refers to fermentation methods to produce these metabolites from media with a diversity of carbon sources, including glucose, lactose or xylose.

8 Claims, 42 Drawing Sheets

I)

II)

SEQUENCE LISTING

<160> NUMBER OF SEQ ID NOS: 25

<210> SEQ ID NO 1
<211> LENGTH: 70
<212> TYPE: DNA
<213> ORGANISM: Escherichia coli

<400> SEQUENCE: 1
taacattatc aggagagcat tatggctgtt actaatgtcg ctgaactttg tgtaggctgg    60
agctgcttcg                                                          70

<210> SEQ ID NO 2
<211> LENGTH: 68
<212> TYPE: DNA
<213> ORGANISM: Escherichia coli

<400> SEQUENCE: 2
ctcagcttta gccggagcag cttctttctt cgctgcagtt tcaccttcca tatgaatatc    60
ctccttag                                                            68

<210> SEQ ID NO 3
<211> LENGTH: 24
<212> TYPE: DNA
<213> ORGANISM: Escherichia coli

<400> SEQUENCE: 3
aatcttgctt acgccacctg gaag                                          24

<210> SEQ ID NO 4
<211> LENGTH: 24
<212> TYPE: DNA
<213> ORGANISM: Escherichia coli

<400> SEQUENCE: 4
ttgtgcagag ggcggaggca taag                                          24

<210> SEQ ID NO 5
<211> LENGTH: 61
<212> TYPE: DNA
<213> ORGANISM: Escherichia coli

<400> SEQUENCE: 5
gtacgtggct gtgggataaa aacaatctgg aggaatgtct gtgttaggct ggagctgctt    60
c                                                                   61

<210> SEQ ID NO 6
<211> LENGTH: 67
<212> TYPE: DNA
<213> ORGANISM: Escherichia coli

<400> SEQUENCE: 6
gggttatagc gcaccacctc aattttcagg ttttcatct cagccattca tatgaatatc     60
ctcctta                                                             67

<210> SEQ ID NO 7
<211> LENGTH: 18
<212> TYPE: DNA
<213> ORGANISM: Escherichia coli

<400> SEQUENCE: 7
ggagtacgtg gctgtggg                                                 18

<210> SEQ ID NO 8
<211> LENGTH: 20
<212> TYPE: DNA
<213> ORGANISM: Escherichia coli

<400> SEQUENCE: 8
tgcagagcct gaccatcaga                                               20

<210> SEQ ID NO 9
<211> LENGTH: 70
<212> TYPE: DNA
<213> ORGANISM: Escherichia coli

<400> SEQUENCE: 9
aacgttgctg cacacgccaa agaagtcaaa ataggtatgg cgattgattg tgtaggctgg   60
agctgcttcg                                                          70

<210> SEQ ID NO 10
<211> LENGTH: 68
<212> TYPE: DNA
<213> ORGANISM: Escherichia coli

<400> SEQUENCE: 10
gcacctttaa cgatatactg ccagaaggtc ggtacatcca tcatactcca tatgaatatc   60
ctccttag                                                            68

<210> SEQ ID NO 11
<211> LENGTH: 21
<212> TYPE: DNA
<213> ORGANISM: Escherichia coli

<400> SEQUENCE: 11
tgtcctctaa ctacagaagg c                                             21

<210> SEQ ID NO 12
<211> LENGTH: 20
<212> TYPE: DNA
<213> ORGANISM: Escherichia coli

<400> SEQUENCE: 12
tatcaaaatc aagaacggcg                                               20

<210> SEQ ID NO 13
<211> LENGTH: 63
<212> TYPE: DNA
<213> ORGANISM: Escherichia coli

<400> SEQUENCE: 13 aaatttgta aaatattttt agtagcttaa atgtgattca actcacacag gaaacagacc    60
atg                                                                 63

<210> SEQ ID NO 14
<211> LENGTH: 59
<212> TYPE: DNA
<213> ORGANISM: Escherichia coli

<400> SEQUENCE: 14
ttaaaccagt tcgttcgggc aggtttcgcc tttttccagc atatgaatat cctccttag    59

<210> SEQ ID NO 15
<211> LENGTH: 26
<212> TYPE: DNA
<213> ORGANISM: Escherichia coli

<400> SEQUENCE: 15
cagcccgagc gtcatcagca gcagcg                                        26

```
<210> SEQ ID NO 16
<211> LENGTH: 22
<212> TYPE: DNA
<213> ORGANISM: Escherichia coli

<400> SEQUENCE: 16
gtagctgttc tggcgtaaca gc                                              22

<210> SEQ ID NO 17
<211> LENGTH: 62
<212> TYPE: DNA
<213> ORGANISM: Escherichia coli

<400> SEQUENCE: 17
atcactggag aaagtcttat gaaactcgcc gtttatagca cagtgtaggc tggagctgct     60
tc                                                                    62

<210> SEQ ID NO 18
<211> LENGTH: 56
<212> TYPE: DNA
<213> ORGANISM: Escherichia coli

<400> SEQUENCE: 18
aggggagcgg caagattaaa ccagttcgtt cgggcacata tgaatatcct ccttag         56

<210> SEQ ID NO 19
<211> LENGTH: 23
<212> TYPE: DNA
<213> ORGANISM: Escherichia coli

<400> SEQUENCE: 19
cagcccgagc gtcatcagca gcg                                             23

<210> SEQ ID NO 20
<211> LENGTH: 22
<212> TYPE: DNA
<213> ORGANISM: Escherichia coli

<400> SEQUENCE: 20
gtagctgttc tggcgtaaca gc                                              22

<210> SEQ ID NO 21
<211> LENGTH: 21
<212> TYPE: DNA
<213> ORGANISM: Escherichia coli

<400> SEQUENCE: 21
ggttgggttg acatactggg t                                               21

<210> SEQ ID NO 22
<211> LENGTH: 21
<212> TYPE: DNA
<213> ORGANISM: Escherichia coli

<400> SEQUENCE: 22
gcttcaccgc cggatgcggt a                                               21

<210> SEQ ID NO 23
<211> LENGTH: 63
<212> TYPE: DNA
<213> ORGANISM: Escherichia coli

<400> SEQUENCE: 23
tacgcagtaa ataaaaaatc cacttaagaa ggtaggtgtt acatgagtta tactgtcggt     60
```

```
acc                                                              63

<210> SEQ ID NO 24
<211> LENGTH: 60
<212> TYPE: DNA
<213> ORGANISM: Escherichia coli

<400> SEQUENCE: 24
attgtacgct ttttactgta cgatttcagt caaatctaat tagaaagcgc tcaggaagag    60

<210> SEQ ID NO 25
<211> LENGTH: 111
<212> TYPE: DNA
<213> ORGANISM: Escherichia coli

<400> SEQUENCE: 25
tacgcagtaa ataaaaaatc cacttaagaa ggtaggtgtt acatgtccga gcaagcttct    60
caatctatgt aattagattt gactgaaatc gtacagtaaa aagcgtacaa t             111
```

STRAINS OF ESCHERICHIA COLI MODIFIED BY METABOLIC ENGINEERING TO PRODUCE CHEMICAL COMPOUNDS FROM HYDROLYZED LIGNOCELLULOSE, PENTOSES, HEXOSES AND OTHER CARBON SOURCES

This is a national stage of PCT/MX10/000075 filed Aug. 6, 2010 and published in Spanish, which claims the priority of Mexican number MX/a/2009/008453 filed Aug. 7, 2009, hereby incorporated by reference.

TECHNICAL FIELD

The present invention refers to the new *Escherichia coli* strains denominated JU15, JU15A, LL26 and MS04 deposited in the Agricultural Research Service (ARS) patent Culture Collection (NRRL) of the Agricultural department of the United States, with access numbers NRRL B-50140, NRRL B-50137, NRRL B-50139 and NRRL B-50138, and their derivatives that produce metabolites, particularly D-lactate, L-lactate or ethanol, with high yield and selectivity from a wide variety of carbon sources. These sources include media formulated with hydrolyzed vegetables, such as sugarcane bagasse, agave bagasse and fast-growing grasses; a wide variety of agro-industrial wastes, such as whey or forestry waste, cellulose, grasses, agave bagasse, paper waste, shavings and sawdust; shrubs and generally any material derived from lignocellulose; glycerol derived from biodiesel production; and sugars derived from starch and sucrose. Through the use of the strains of *E. coli* referenced above, these sources are used in the production of the metabolites of interest (especially D-lactate, L-lactate or ethanol) as the only way to regenerate the reducing power. The invention also refers to the fermentation methods to produce these metabolites from media with different carbon sources, including glucose, lactose or xylose.

BACKGROUND OF THE INVENTION

In recent years, the use of recombinant DNA technology and the systematic analysis of biological data have increased considerably, yielding Metabolic Pathway Engineering (MPE), which is defined as the modification and/or introduction of new biochemical reactions for the direct improvement of cellular properties through recombinant DNA technology (Stephanopoulos, 1999; Bailey, 1991). Specifically, new strains are now being developed through MPE that have the property of being able to grow in mineral media and to produce primarily a single microbial metabolite—for example, only one lactate isomer (Bai et al. 2003; Dien et al., 2002; Zhou et al. 2003a and 2003b; Zhu and Shimizu 2004; Zhou et al., 2006a; Zhou et al. 2006b; Zhou et al., 2005).

Lactic Acid.

In the chemical industry, especially in the manufacturing of raw materials for the production of plastics of biological origin, the biotechnological production of lactic acid has attracted a large amount of interest recently, as this compound offers a sustainable alternative for the manufacturing of high-quality biodegradable plastics known by the generic name of polylactates (PLAs); examples include polylactate and ethyl-lactate (Dien et al., 2002; Skory, 2003). The synthesis of biodegradable PLAs requires the separate production of the D and L lactate isomers. In addition, the physical and biodegradative properties of PLA depend on the proportion of the D and L forms used in the synthesis of the polymer. Lactate can be produced by microbial fermentation or by chemical synthesis (Narayanan et al., 2004). The most commonly used chemical process is the hydrolysis of lactonitrile with strong acids; however, there are other chemical routes (John et al., 2007), such as the oxidation of propylene glycol, the reaction of acetaldehyde with carbon monoxide and water at high temperatures and the hydrolysis of chloropropionic acid, among others. All of these routes yield a mixture of D and L isomers as a final product and depend on raw materials derived from petroleum, which makes these production processes less sustainable. In contrast, the biotechnological production of lactic acid has several advantages over chemical synthesis: 1) the low cost of the substrates, 2) the low production temperature, 3) the low energy consumption and 4) the specificity for the desired stereoisomer. The lactate is produced through a process of microbial fermentation of culture media with an easily assimilated carbon source, such as glucose.

Ethanol

One of the most difficult challenges in the present search for substitutes for fuels derived from petroleum is the identification of possible alternative liquid fuels.

The production of ethanol from biomass is one of the few currently viable options (Mielenz, 2001). Several technologies are in the growth stage; a large variety of raw materials can be used; and the ethanol produced is a valuable and versatile compound, as it can be used as an oxygenating agent, fuel or solvent or be transformed, using established technologies, into other fuels (e.g., biodiesel) (Bungay, 2004).

Ethanol can be used for many applications. The primary application discussed in this document is as a liquid fuel that will oxygenate, substitute for or complement fossil fuels that are currently used in internal combustion engines. Other applications of ethanol include its use as a fuel in industrial boilers, lamps, furnaces, turbines, among others.

When compared in volumetric terms, the energetic content of ethanol is approximately two-thirds of that stored in gasoline or diesel. However, ethanol has a high octane value, which causes the engines that use gasoline-ethanol mixtures to have a better efficiency. Mixtures that contain up to 22% (v/v) ethanol can be used successfully in current gasoline engines, that is, without the need of modifying these internal combustion engines.

Another alternative use of ethanol is as an oxygenating agent. To improve combustion and to reduce the levels of carbon monoxide produced, fuels need to elevate their octane value without using lead. To that end, alcohols and esters have been used. Currently, in Mexico, tert-butyl ethers are used, of which methyl tert-butyl ether (MTBE) is the most commonly used. However, it is known today that these compounds can accumulate in groundwater, are resistant to chemical and biological degradation and are carcinogenic to humans in parts per million concentrations. In several states, such as California, their use has been prohibited.

Traditionally, ethanol is obtained through the fermentation of glucose or sucrose, which are obtained from corn starch and cane sugar, respectively. This fermentation is conducted using ethanol-generating organisms, such as *Saccharomyces cerevisiae*. This organism is traditionally used for the production of ethanol from glucose, which is generated from the hydrolysis of grain starch and sucrose obtained from cane sugar or sugar beet. This microorganism does not have the ability to metabolize the five-carbon sugars, known as pentoses that are abundantly found in hydrolyzed vegetable material (Hahn-Hagerdal of al., 1993). Another ethanol-generating organism is *Zymomonas mobilis*, a Gram-negative bacterium, which has the native ability to produce a good yield of ethanol due to its metabolic characteristics. Among these characteristics are two very efficient enzymatic activities, those of pyruvate decarboxylase (Pdc) and alcohol dehydrogenase (Adh), which convert pyruvate into acetaldehyde and ethanol, respectively. However, as also occurs with *S. cerevisiae*, *Z. mobilis* is limited in the sugars that it can metabolize. This organism can only use sucrose, glucose and fructose, and it does not use xylose, other pentoses or other disaccharides.

Carbon Sources

Glucose

Cellulose is the greatest component of lignocellulose (20-50%). It is a linear polymer composed of dextrose subunits (D-glucose) that are joined by glycosidic bonds β-(1-4), and due to its structural conformation, it is highly resistant to hydrolysis. To take advantage of cellulose, it is necessary to hydrolyze it with cellulases. The hydrolysis of cellulose yields glucose, which is fermentable by the strains mentioned in the present invention. Glucose is primarily obtained from the hydrolysis of starch Xylose and Other Monomers In contrast to cellulose, hemicellulose is not chemically homogeneous, as it is a heterogeneous polysaccharide that contains hexose monomers (glucose, mannose and galactose), pentose monomers (xylose and arabinose) and several acids (acetic acid and glucuronic acid). This composition increases the difficulty of the bioconversion of hemicellulose to fermentation products that are of interest for industrial use. In addition, hemicellulose is the second most common polysaccharide in nature, as it represents 20-35% of the cell mass of lignocellulose. The proportions of pentoses and hexoses in hemicellulose are 85 and 15%, respectively, where xylose is the most abundant, followed by glucose and arabinose (75, 15 and 10%, respectively) (Saha, 2003). Hemicellulose can be converted into monomeric sugars through the use of hydrolysis at temperatures below 200° C. using low acid concentrations, although there are several hydrolysis methods: physical, physicochemical, chemical and/or biological (Sun et al., 2002).

Thus, it can be concluded that, excepting glucose, xylose is the most abundant monosaccharide in nature and is generally found polymerized in the hemicellulose fraction of the vegetable tissue. However, the variety of microorganisms that metabolize both pentoses and hexoses is very limited. Furthermore, there are no wild microorganisms that can efficiently catabolize pentoses or mixtures of pentoses and hexoses through fermentation processes into products of industrial interest at high yields (Hernández-Montalvo et al., 2001).

Therefore, the conversion of lignocellulose materials has serious limiting factors, as these materials are composed of sugar polymers, primarily glucose and xylose; xylose is a pentose that is not fermentable by most of the wild or genetically modified microorganisms used in industry, such as *Saccharomyces cerevisiae*, *Corynebacterium glutamicum*, certain lactobacilli, *Zymomonas mobilis* or *Bacillus subtillis* (Dien et al., 2001). Another disadvantage for the industrial use of lignocellulose materials is that the majority of microorganisms used to this end, such as lactobacilli, require complex culture media, thus increasing the costs of production because of the need for nutrients, product purification, etc. In addition, in the case of lactic acid, most of the microorganisms synthesize only the D-lactic isomer or a mixture of D and L-lactic.

Lactose

Lactose is a disaccharide made up of glucose and galactose molecules joined by a beta 1-4 link. This disaccharide is found in mammalian milk, and it is common to find it in whey as an agro-industrial residue obtained in cheese production.

*Escherichia coli*

Among the microorganisms used industrially for the production of D-lactate, species from the genera *Lactobacillus*, *Rhizopus* and *Escherichia* are most commonly used. Of these microorganisms, *Escherichia coli* have several advantageous characteristics as the base microorganism for the development of strains and for the production of biotechnology products. Among these characteristics are the following: it grows rapidly under aerobic or anaerobic conditions, its complete genome is known, methodologies are available to modify its genome, and it can metabolize both hexoses and pentoses, as well as disaccharides and a wide variety of other sugars and carbon sources, using only mineral salts as nutrients. For this reason, the strategies of metabolic engineering propose changes in the fermentation pathways to modify the balance of carbon toward the desired product, maintaining the redox balance and preventing the formation of subproducts, with the goal of improving the accumulation of a single fermentation product. For example, if the end product is lactic acid (Zhu et al., 2007), a homolactic microorganism is obtained, whereas, if only ethanol is produced, the microorganism is homoethanologenic (Zhou et al., 2008).

According to the functional metabolic network of *E. coli* in fermentation conditions, for each mole of glucose (Glc) that is catabolized to pyruvate, two moles of ATP are obtained. If half of the pyruvate generated is converted into acetic acid, the yield increases to 3 $mol_{ATP}/mol_{Glc}$. However, in the case of xylose (Xyl), the yield is only 0.67 $mol_{ATP}/mol_{Xyl}$ when *E. coli* catabolizes this sugar into pyruvate. This value is so low that the enzymes pyruvate formate lyase (Pfl) and acetate kinase (Ack) are essential in the growth of *E. coli* from xylose in fermentation conditions, as the conversion of one mole of pyruvate into acetyl-CoA and, in turn, into acetate generates one extra mole of ATP, increasing the yield of ATP to 1.5 $mol_{ATP}/mol_{Xyl}$. As a consequence, the *E. coli* W3110 strains without pflB cannot grow in pentose, as they only yield 0.67 $mol_{ATP}/mol_{Xyl}$. The insufficiency of ATP was confirmed by inactivating the acetate kinase (ack) gene in *E. coli* W3110. This mutant was incapable of growing in the minimal media supplemented with xylose in anaerobic conditions, verifying the need for the ATP produced by Ack (Hasona et al., 2004). For glucose, the transport and phosphorylation is carried out by the PTS system, with an equivalent cost of ATP. In contrast, for xylose, the cell spends two molecules of ATP, one for the transport (high-affinity ABC transporter) and the second for phosphorylation (Lin, 1996; Linton and Higgins 1998). In arabinose, the internalization of the pentose in the cell is carried out by symport (arabinose/$H^+$) through AraE, a low- and high-affinity transporter. This approach conserves one molecule of ATP spent in the transport of pentoses through the ABC transporter, and both mutants (pfl and ack) grow in arabinose (Hasona et al., 2004).

The Use of *E. coli* in the Production of Lactic Acid

For the production of lactic acid, *E. coli* has a gene that codes for an enzyme vital to lactate production, lactate dehydrogenase (IdhA), which is expressed in anaerobic conditions (Zhou et al., 2003a). However, when grown in the presence of glucose or xylose, *E. coli* is heterofermentative, yielding acetic, formic, lactic and succinic acids, in addition to ethanol, hydrogen and carbon dioxide (Bock and Sawers 1996). Through MPE techniques, *E. coli* strains have been modified by the blockade of pathways that compete for pyruvate availability to induce the microorganism to become homofermentative and mostly produce D-lactate (U.S. Patent Application No US2007/0037265) from pyruvate; however, those strains were modified to use only glucose as a carbon source and to produce D-lactate, with high conversion yields. In contrast, there are reports that detail the inability of *E. coli* strains that produce D-lactate to grow using xylose as the main source of carbon, due to the low yield of ATP that is obtained with this sugar (Hasona et al., 2004).

The most commonly used strategy for the generation of *E. coli* strains that produce high optical purity D-lactate consists of suppressing the gene that codes for the pyruvate formate lyase activating enzyme (pflB) (Zhou et al., 2003a and 2003b; Zhu and Shimizu 2004; Zhou et al. 2006a; Zhou et al., 2006b; Zhou et al., 2005). This strategy has yielded conversion efficiencies of the carbon source into D-lactate above the theoretical 95% value (Zhou et al., 2003a and 2003b) but has restricted the industrial process to use glucose as the only carbon source. Another disadvantage comes as a response to a low availability of acetyl-CoA (a key metabolite in the contribution of carbon backbone to cell mass), yielding strains with a very low or null growth rate in anaerobic growth conditions or with glucose as the only carbon source. Typically, these strains are incapable of growing unless the media is supplemented with acetate (Zhou et al., 2003a), driving up the price of the culture media and/or complicating the industrial process.

The Use of *E. coli* in the Production of Organic Acids and Ethanol

In contrast, *E. coli* has a pathway to produce other compounds of industrial interest, such as ethanol, in a natural fashion. However, the amount of alcohol that is produced in this manner is very low. In addition to the product of interest, a mixture of other fermentation products is produced, among which are acetic, formic, succinic and lactic acids (Gonzalez et al., 2002; Dien et al., 2003; Lawford and Rousseau 1996; Lawford and Rousseau, 1997); thus, the microorganism is heterofermentative. With the use of Metabolic Pathway Engineering (MPE), the flow of carbon has been redirected to a heterologous ethanol production pathway in *E. coli*, yielding strains with a different genetic background from those reported in the present invention that are capable of providing good yields in the fermentation of glucose or xylose to ethanol (Otha et al., 1991).

DETAILED DESCRIPTION OF THE INVENTION

Figure 1:
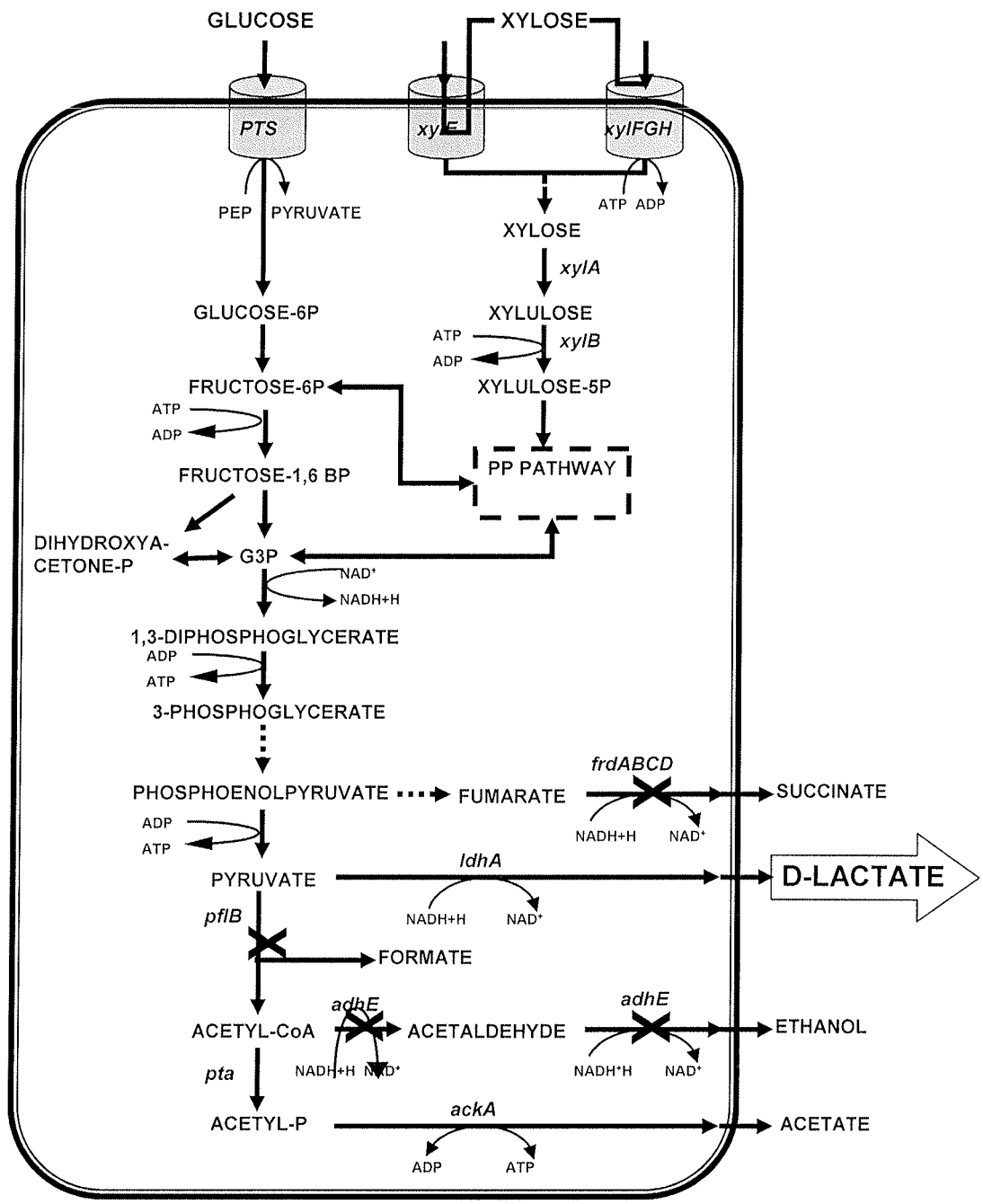
FIG. 1. Image that shows the inactivated pathways in the glucose and xylose metabolic network of *E. coli*; and the main fermentation products, including the ATP, in CL3 strain.

In the present invention, through the use of a Metabolic Pathway Engineering (MPE) original design and adaptive evolution, *E. coli* strains capable of growing with different basic carbon sources, such as glucose, xylose, arabinose and/or lactose, among others, are used to convert the carbon source into a single metabolite of interest, particularly L-lactate, D-lactate or even ethanol, with high productivity and yield. The starting material was a homolactic strain that showed superior abilities in terms of the specific growth rate, glucose consumption and D-lactate production compared with the *E. coli* strains previously reported. The *E. coli* strain named in the present invention as strain JU15, which has been deposited in the ARS Patent Culture Collection (NRRL) of the U.S. Department of Agriculture with access number NRRL B-50140, is capable of fermenting sources that are difficult to assimilate, such as hydrolysates of the hemicellulose fraction of vegetable tissues (abundance of xylose), including sugar cane bagasse, and of producing D-lactate with a yield of 95% of the theoretical value, with velocities comparable to that of lactic acid bacteria (strains commonly used to produce D-lactate).

In a time when the planet is experiencing climate change, which is a consequence of an indiscriminate use of 'dirty' technologies that consume finite raw materials, there is a need to develop sustainable technologies that are capable of producing intermediate raw materials for the chemical, pharmaceutical, petrochemical or processing industries that will allow the substitution of grains or seeds (which are the basis for the processing of industrialized cereals, sweeteners, bread, tortillas, etc., and are of critical importance to human sustenance) for petroleum derivatives (finite and continuously increasing in price). In addition, there is the opportunity to use the abundant agro-industrial resources or vegetable tissues, which are currently underused in the best of cases and which can be significant pollution sources in the worst-case scenario. However, as has been mentioned before, few microorganisms found in nature are able to grow and produce metabolites of industrial interest from less conventional sugars, such as xylose, the second most abundant monosaccharide in nature (although in its polymerized form), or lactose, a residual disaccharide of the milk product industry. Thus, a technical problem is identified that consists of constructing strains for industrial use that efficiently and preferentially produce metabolites of industrial interest, starting not only from glucose but also from less conventional sugars, such as xylose and lactose; from other carbohydrates; and even from high concentrations of acetic acid.

The developers of the present invention, seeking to propose a solution to that technical problem, have generated new microbial strains that are capable of growing and fermenting glucose. However, most importantly, these strains can also use xylose and even lactose efficiently, converting these carbon sources into a single metabolite of industrial interest. Among the metabolites that can be produced with the strains in the present invention are the acetic, succinic, malic, pyruvic and lactic organic acids, with the last being produced as either the D or L isomer with a high degree of optical purity. Other possible metabolites include alcohols, such as ethanol or 1,2- and 1,3-propanediol, among others. To achieve this end, the inventors used the most recent techniques of metabolic pathway engineering, following original criteria.

In another aspect, the present invention refers to methods or processes to bioconvert sugars into metabolites of industrial interest through the use of the strains of the present invention. With these methods, the sugars present in vegetable tissues, such as sugar cane bagasse, are converted into different metabolites of industrial interest, such as D and L-lactate with yields on the order of 95% and volumetric productivities of approximately 1 g/(L*h) and ethanol with a 90% yield and 1 g/(L*h) productivity. A great advantage of the methods of the present invention is that the yield of such metabolites can be obtained through fermentation in a simple and cheap medium using the sugars found, for example, in hydrolysates of the hemicellulose fraction of vegetable tissues, such as sugar cane bagasse, or in agro-industrial residues, such as whey, and resulting in high yield and productivity. These strains are compared with other strains of *E. coli* previously reported that do not efficiently metabolize xylose and that require complex media to grow.

The present invention yielded several bacterial strains that were genetically modified in an incremental fashion so that lactate production is the only major pathway for the regeneration of reducing power. Among these strains is the modified recombinant strain CL3 (Utrilla et al., 2009), with the genes pflB, adhE and frd suppressed to stimulate the homofermentative production of D-lactate (see FIG. 1); this strain shows superior abilities in terms of the specific growth rate, specific glucose consumption rate and specific D-lactate production rate relative to the strains previously reported. In contrast to the strains previously reported, this strain is capable of growing efficiently at a specific rate of $0.22\ h^{-1}$ in a simple mineral medium formulated with glucose as the only carbon source. This strain shows a 95% conversion yield of glucose to D-lactate at a specific velocity of glucose consumption of 6 g/(g cells*h). Additionally, as a result of this strain's unusual ability of growing at densities of approximately 1 g/L, it has the highest volumetric productivity of D-lactate achieved in a culture of an unevolved strain. Because of the characteristics previously mentioned, this strain was used as a starting point for subsequent modifications for the efficient metabolism of xylose and the production of other metabolites. The unprecedented ability of the CL3 strain to grow optimally in anaerobic conditions was considered to be a key ability for use as a starting point for the development of the present invention.

Figure 2:
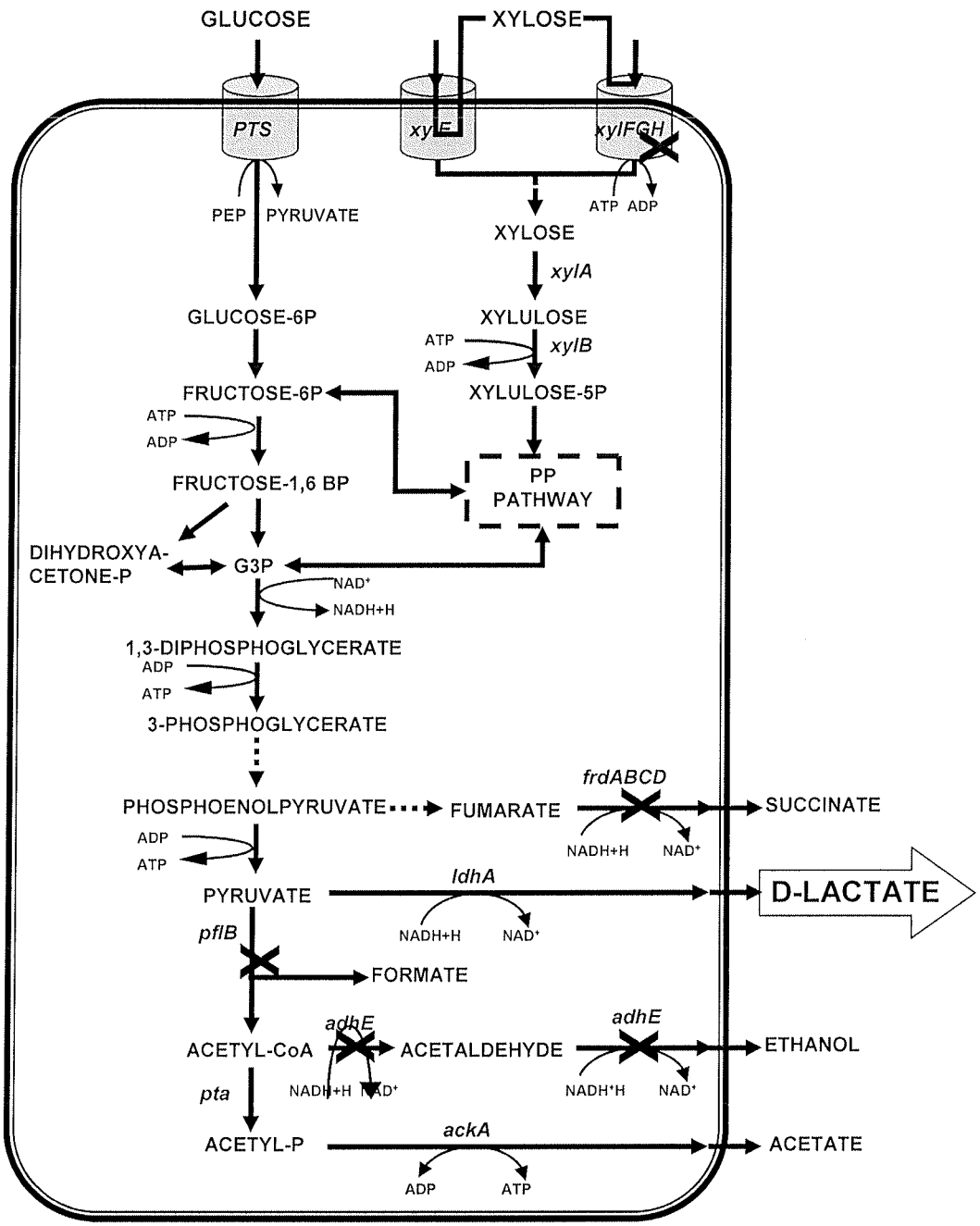
FIG. 2. Image that shows the inactivated pathways in the glucose and xylose metabolic network of *E. coli*; and the main fermentation products, including the ATP, in JU15 strain.
Figure 3:
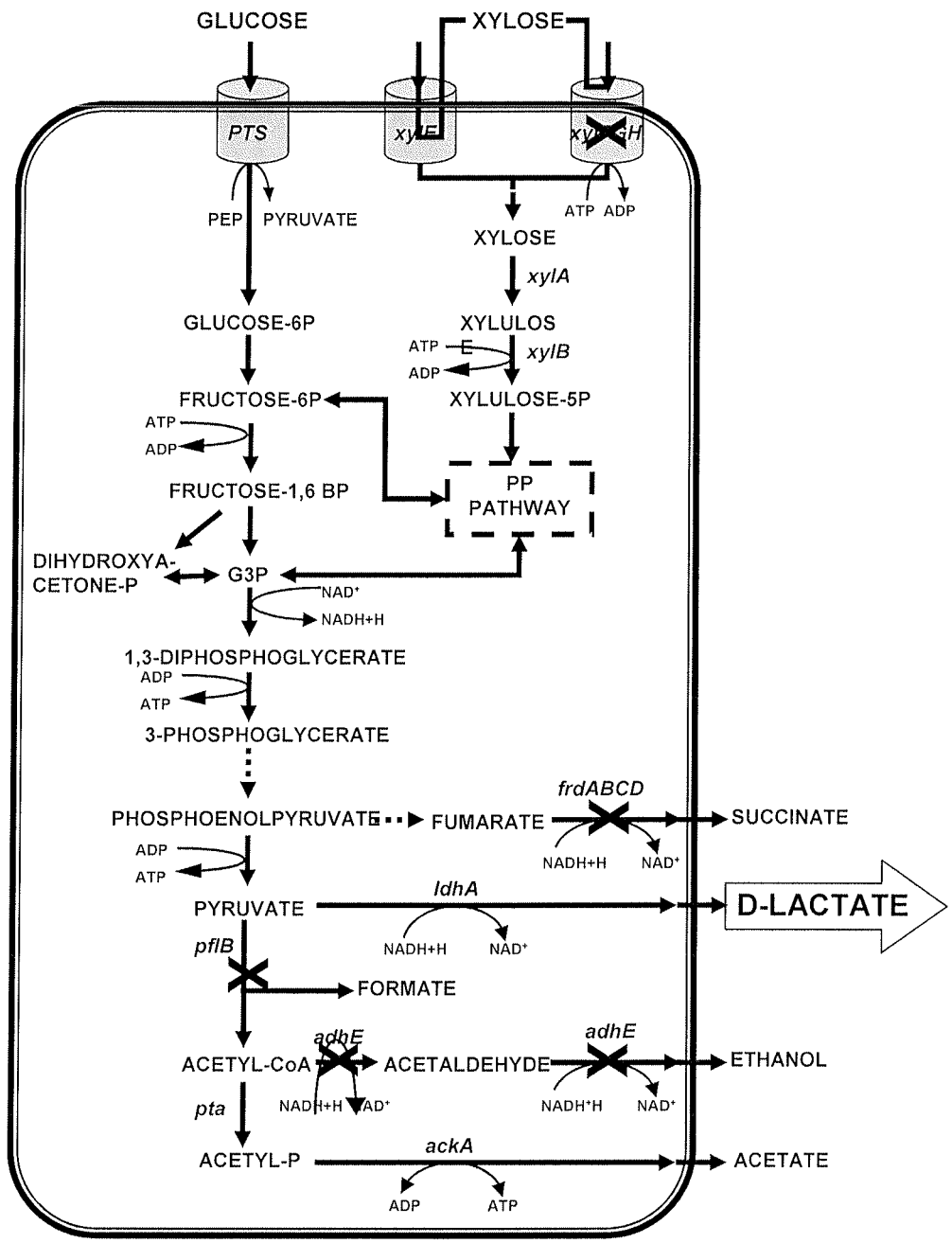
FIG. 3. Image that shows the inactivated pathways in the glucose and xylose metabolic network of *E. coli*; and the main fermentation products, including the ATP, in JU15A strain.

This CL3 strain was used as the starting point for subsequent modification and to achieve the efficient conversion of xylose into lactate, for which modifications to xylose transport were performed, inactivating the ATP-dependent transporter (xylFGH) (see FIG. 2) and subjecting this bacterial strain to a process of adaptive evolution in mineral media (AM2) with 12% xylose. This process yielded the new strain labeled in the present invention as JU15 (deposited in the ARS Patent Culture Collection (NRRL) of the U.S. Department of Agriculture with access number NRRL B-50140). Through a second process of adaptive evolution, using medium with both xylose and acetate to prevent growth inhibition by acetate, a derivative strain named JU15A was obtained (see the diagram of its metabolism in FIG. 3) (deposited in the ARS Patent Culture Collection (NRRL) of the U.S. Department of Agriculture with access number NRRL B-50137). In contrast to previous stains, JU15A is capable of growing even in culture media with high acetate concentrations, even those greater than 15 g/L, which is the acetate concentration that is found in vegetable hydrolysates, because the acetate is usually liberated when the hemicellulose is hydrolyzed, as it is already acetylated.

Figure 40:
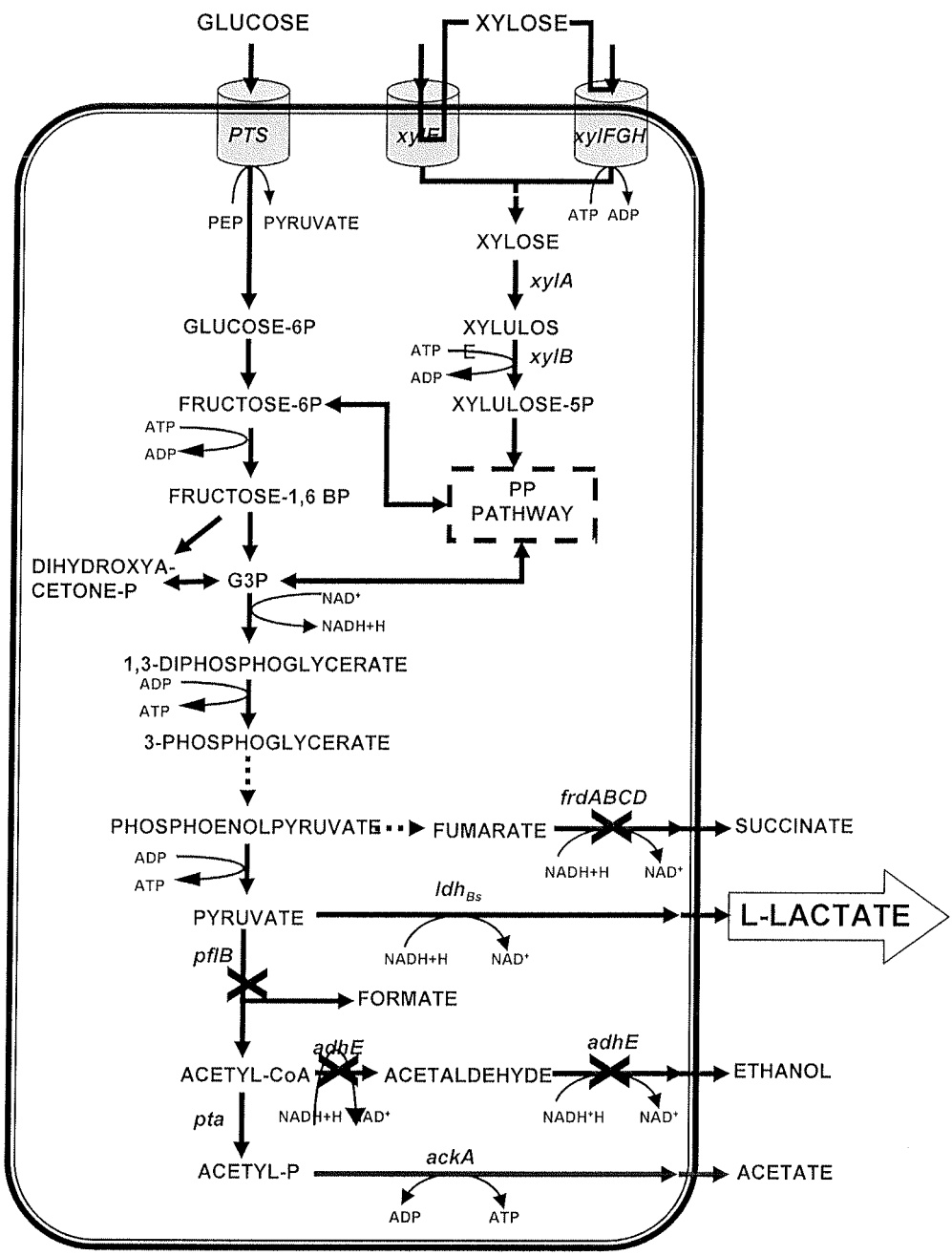
FIG. 40. Image that shows the inactivated pathways in the glucose and xylose metabolic network of *E. coli*; and the main fermentation products, including the ATP, in strain LL26.
Figure 41:
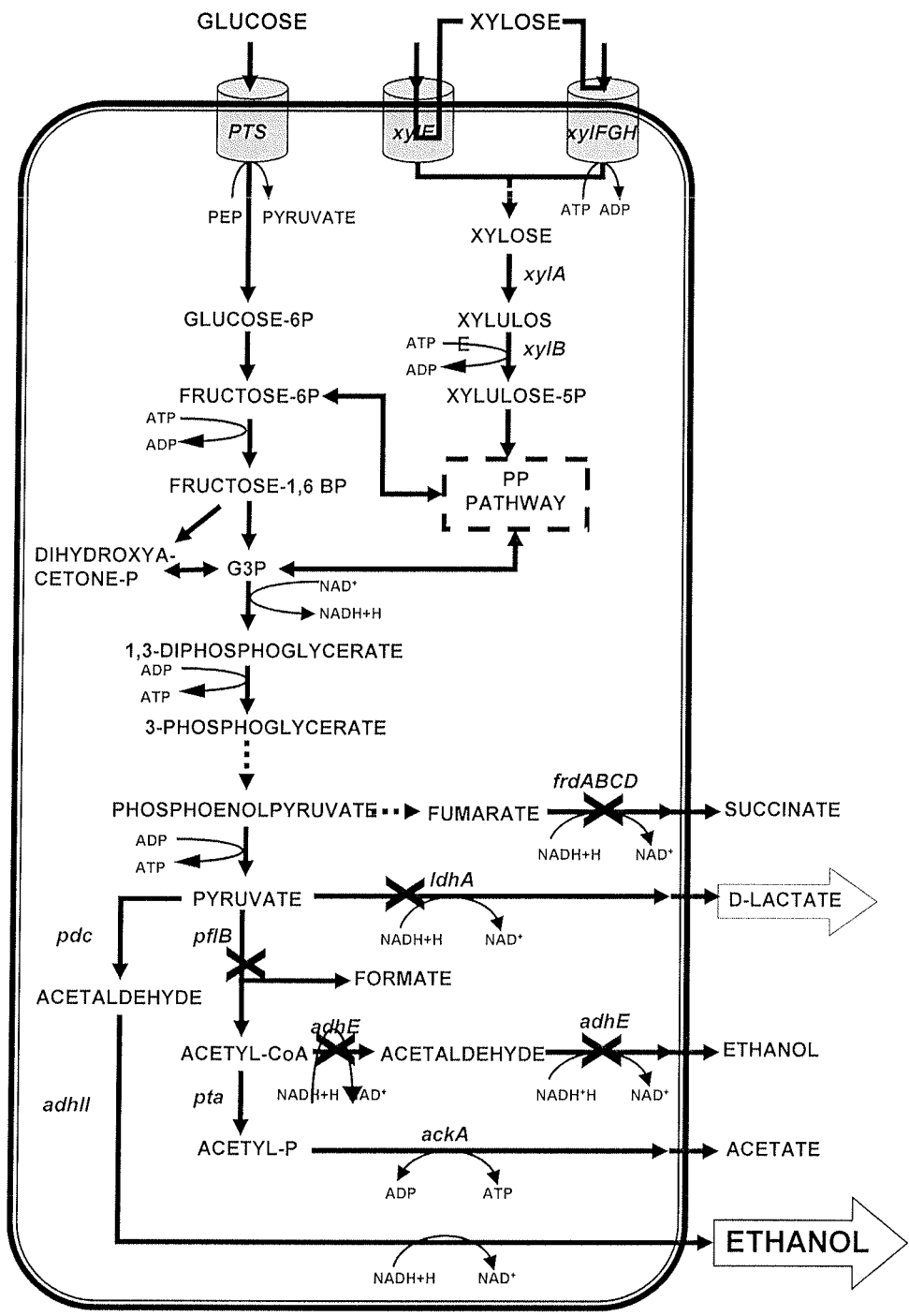
FIG. 41. Image that shows the inactivated pathways in the glucose and xylose metabolic network of *E. coli*; and the main fermentation products, including the ATP, in strain MS04.

To demonstrate the versatility of the strains in the present invention, both strains, JU15 and JU15A, had the gene that codes for the homologous lactate dehydrogenase of *E. coli* (IdhA) suppressed to disable D-lactate production. Next, the necessary coding gene or genes for the synthesis of other metabolites of industrial interest were inserted; L-lactate and ethanol were the metabolites of interest in the present invention. To illustrate, yet not limit, the versatility of the JU15 and JU15A strains, the first strain received the gene that codes for the lactate dehydrogenase of *B. subtilis* (see FIG. 40) and was subjected to a process of adaptive evolution in the presence of acetate; the new recombinant strain thus obtained was capable of not only growing with xylose as the main carbon source and in the presence of acetate but also producing L-lactate. This strain is labeled in the present invention as LL26 (deposited in the ARS Patent Culture Collection (NRRL) of the U.S. Department of Agriculture with access number NRRL B-50139) (Examples 12 and 13). In similar fashion to the JU15A strain, after suppressing the gene IdhA and inserting the *Z. mobilis* genes pdc and adhB, (see FIG. 41), another new recombinant strain was obtained that was capable of growing with xylose as its main carbon source in the presence of acetate and, in addition, of producing ethanol while efficiently consuming xylose; this project represents the first time that this combination of traits has been reported for strains of *E. coli*. This strain was labeled MS04 in the present invention and deposited in the ARS Patent Culture Collection (NRRL) of the U.S. Department of Agriculture with access number NRRL B-50138.

Thus, the present invention also refers to the methods of producing D-lactate, L-lactate or even ethanol from xylose as the main carbon source utilizing different fermentation processes and using the strains in the present invention.

In addition and with the purpose of showing the versatility of the strains in the present invention with regard to their use of several carbon sources, the growth possibility and acetate conversion of the strain JU15 was evaluated with lactose as the main carbon source, in mineral medium and with an agro-industrial residue, such as whey. The results show that this strain is capable of using lactose both for growth and for the conversion into a single metabolite of interest, in this case, D-lactate. Because this pathway is inherent to the parent strain used for the genetic modifications, it is obvious that the other strains, such as JU15A, MS04, CL3 and LL26, have the same ability.

Thus, the present invention yields new strains of genetically modified *Escherichia coli* for the versatile, efficient and preferential production of metabolites from the versatile consumption of a variety of low-cost carbon sources. Similarly, the present invention provides methods for the production of said metabolites from such carbon sources through their fermentation by those new strains.

For the construction of the strains of the present invention, the parent strain used was derived (see the Materials and Methods) from the strain *E. coli* MG1655, which was previously sequenced (Hayashi K., et al. 2006). To promote the efficient conversion of sugars (glucose, xylose, lactose, among others) into a preferential product of industrial interest (D or L-lactate, ethanol, etc.), the carbon flux toward other metabolites was eliminated through the suppression of genes that code for the fermentation metabolism enzymes and that compete for pyruvate (pflB and dhE, in the first step and frdA in a second step, see Examples 1, 2 and 3). This process yielded the strains CL1 and CL3, of which the latter is capable of growing and converting glucose into D-lactate at high rates, $0.22\ h^{-1}$ and $4\ g_{Lact}/(g_{DCW}*h)$ [DCW: dry cellular weight] (see Example 4 for details). Through the suppression of the genes that code for the ATP-dependent xylose transporter in the present invention, another improved *E. coli* strain was obtained and was labeled JU01 (*E. coli* MG1655 ΔpflB ΔadhE Δfrd ΔxylFGH). Thus, for the first time, with the use of a symport-type transporter (xylose/$H^+$), an increased yield of ATP per mole of metabolized xylose was achieved, notably improving the capacity of the strains to grow in xylose as the only (or main) carbon source. This result was achieved through the suppression of the xylF, xylG and xylH genes (for details, see Example 5). However, this strain required a long period of time to consume the xylose present. Therefore, through a process of subsequent transferences in mineral medium with 12% xylose (adaptive evolution), the present invention yielded a mutant strain with an improved capacity for growing in xylose and for producing organic acids, such as D-lactate. This new strain is labeled in the present invention as JU15 (for details, see Example 6). This strain was characterized in mineral medium with xylose.

Afterwards, in a simulated hydrolyzed vegetable tissue medium that was abundant in xylose, although with relatively high acetate concentrations (because acetate usually is liberated when hydrolyzing hemicellulose, as it is acetylated, and such concentrations can dampen the growth of microorganisms in such media), it was observed that the JU15 strain showed an inconveniently prolonged lag phase of 12 h, which led the inventors to newly improve the strain. To this end, they subjected the JU15 strain to two steps of adaptive evolution in the presence of acetate, with the goal of obtaining a mutant with a significantly decreased lag phase. This new strain was labeled JU15A (see Example 7) and was subsequently characterized (see Examples 8 and 9).

Similarly, the possibility of using other carbon sources, such as certain industrial residues, including whey, which is rich in lactose (see Examples 10 and 11), was tested. Whey is considered to pose an environmental problem because it generates pollution when dumped in groundwater by considerably increasing the biochemical demand for oxygen, diminishing the availability of this important nutrient to the wild flora and fauna. To illustrate this possibility in the present invention, it was shown that the JU15 strain is capable of converting the lactose present in whey to D-lactate (see Example 11).

An additional objective of the present invention was to present a method for producing D or L-lactate that is optically pure from media rich in xylose, such as the hydrolysates of vegetable tissues, including sugar cane bagasse, using these new strains of *E. coli*. To this end, the inventors decided to genetically modify strain JU15 by the suppression of the gene that codes for *E. coli* lactate dehydrogenase and the insertion of the gene that codes for *B. subtilis* lactate dehydrogenase in the same JU15 strain. These modifications yielded a strain that produced L-lactate, labeled in the present invention as LL2 (Examples 12 and 13). To improve this strain's ability to grow in culture medium abundant in xylose, the inventors subjected strain LL2 to a procedure of adaptive evolution, obtaining an improved strain, labeled in the present invention as LL26 (*E. coli* JU15,:: $ldh_{Bs}$, for details, see Example 14).

Finally, with the goal of illustrating the application of MPE and adaptive evolution techniques for the production of other raw materials of great industrial and commercial interest, such as bioethanol, the inventors obtained a mutant strain of *E. coli* derived from JU15A. This strain was subjected to an interruption of ldha gene and the incorporation of the pdc and adhB genes of *Z. mobilis*, under the pflB promoter, in addition to the adaptive evolution process The mutant strain finally obtained was labeled in the present invention as strain MS04 (*E. coli* JU15A ΔldhA, PpflB:$pdc_{Zm}$-$adhB_{Zm}$) and is capable of growing in culture media abundant in xylose as the most important carbon source and of producing ethanol with high productivity and yield (93% with respect to the theoretical maximum) (for details, see Example 15).

Thus, the present invention shows that modifications to the fermentation pathways and to xylose transport, followed by a selection process in subsequent transfers, yielded new genetically modified bacterial strains. These strains are capable of appropriately growing in mineral media abundant in xylose, glucose or lactose, among other sugars, and of converting the sugars present in vegetable hydrolysates, such as sugarcane bagasse, into only D or L-lactate or even into only ethanol. These strains can be used to obtain such products using formulated culture media based on vegetable hydrolysates, such as sugarcane bagasse.

Similar to the examples of L-lactate and ethanol, the strains in the present invention can have the ldhA gene suppressed and the necessary gene(s) inserted for the production of some other metabolite. For example, the pyruvate consumption pathways can be inactivated to thereby obtain a pyruvate-producing strain, or the strains can be forced to use homologous pathways for the production of succinate, 1,2-propanediol or malate as the only pathway of reducing power regeneration. Heterologous pathways, such as that of 1,3-propanediol, can be inserted to regenerate the reducing power, or L-alanine can be used as an amino acid that also allows the regeneration of the reducing power.

The selection of the starting strain from those described in this document will depend on several criteria, including the carbon source for fermentation and the possible presence of acetate in the culture media. Thus, for example, if the fermentation is to occur in glucose, strain CL3 can be used. In contrast, in xylose-rich media, JU15 can be used, and if the growth medium contains acetate, strain JU15A can be used. If the fermentation is to occur in lactose, any of the strains can be used. Despite not being the most optimal manner, strains LL26 or MS04 can be used, suppressing gene $ldh_{Bs}$ or genes $pdc_{Zm}$ and $adhB_{Zm}$ instead of gene ldhA and inserting the gene(s) that make it possible to produce the metabolite of interest.

MATERIALS AND METHODS

The microorganisms and plasmids used in the present invention are presented in Tables 1 and 2, and also in the SEQUENCE LISTING.

TABLE 1

*E. coli* strains used in this invention

| Strains | Genotype | Reference or NRRL deposit number | Main phenotype |
| --- | --- | --- | --- |
| *E. coli* K12 | *E. coli* MG1655 | Wild type strain | Wild type strain, heterofermentative |
| *E. coli* CL1 | *E. coli* MG1655 ΔpflB ΔadhE | Utrilla et al., 2009, NRRL B-50195 | Heterolactic, lactate producer, succinate as byproduct |
| *E. coli* CL3 | *E. coli* MG1655 ΔpflB ΔadhE ΔfrdA | Utrilla et al., 2009, NRRL B-50195 | Homolactic (D-Lactate) |

TABLE 1-continued

E. coli strains used in this invention

| Strains | Genotype | Reference or NRRL deposit number | Main phenotype |
|---|---|---|---|
| E. coli JU01 | E. coli MG1655 ΔpflB ΔadhE ΔfrdA ΔxylFGH | This invention | Homolactic (D-Lactate), Improved growth on xylose |
| E. coli JU15 | E. coli MG1655 ΔpflB ΔadhE ΔfrdA ΔxylFGH E15 | This invention, NRRL B-50140 | Homolactic (D-Lactate), Improved growth on xylose |
| E. coli JU15A | E. coli JU15 derivative with improved acetate tolerance. JU15 Ac$^r$ | This invention, NRRL B-50137 | Homolactic (D-Lactate), Improved growth on xylose. Acetate tolerant |
| E. coli LL26 | E. coli JU15 ΔldhA PldhA:: lctE$_{Bs}$, | This invention, NRRL B-50139 | Homolactic, L-Lactate producer |
| E. coli MS04 | E. coli JU15A ΔldhA, PpflB::pdc$_{Zm}$-adhB$_{Zm}$ | This invention, NRRL B-50138 | Homofermentative, Ethanol producer |

Abbreviations:
Δ Deletion
P Promoter
pflB pyruvate formate lyase gene
adhE E. coli alcohol hydrogenase gene
frdA fumarate reductase gene
xylFGH ATP dependent xylose transport
E15 Evolved strain 15
JU15A JU15 derivative with improved acetate tolerance
ldh$_{Bs}$ B. subitilis L-lactate dehydrogenase de gene
ldhA E. coli lactate dehydrogenase gene
pdc$_{Zm}$-adhB$_{Zm}$ Z. mobilis pyruvate decarboxylase and alcohol dehydrogenase genes
Ac$^r$ Acetate tolerant

TABLE 2

Plasmids used in this invention

Figure 27:
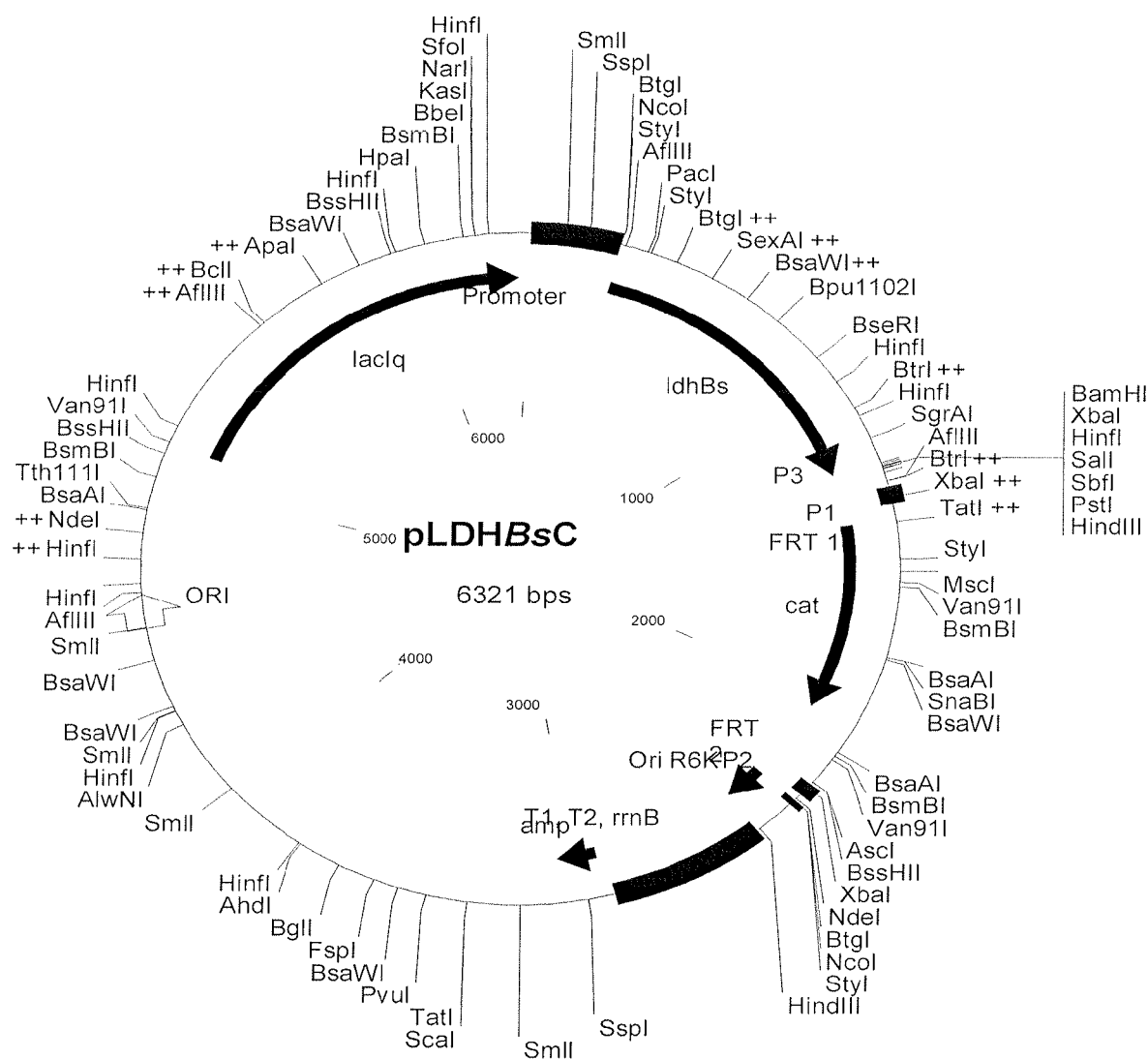
FIG. 27. Image that shows the pLDHBsC plasmid carring the gene $LDH_{Bs}$, the P1, FRT sites; the chloramphenicol acetyl transferase gene; and the FRT and P2 sites.

| Plasmid | Description | Reference |
|---|---|---|
| pKD46 | Thermosensitive vector, arabinose inducible expression of the red recombinase system | Datsenko and Wanner 2000 |
| pKD4 | Template used to amplify the Km resistance cassette flanked by FRT sites | Datsenko and Wanner 2000 |
| pCP20 | Thermosensitive vector, used for the FLP recombinase expression | Datsenko and Wanner 2000 |
| pKO3-pflB | pKO3 (Church et al 1999) derivative with pflB homology regions | Lara et al., 2006 |
| pTrclctE | pTrc99A derivative expressing the B. subtilis lactate dehydrogenase | Vázquez-Limón et al., 2007 |
| pLDH$_{Bs}$C | pTrclctE derivative with Cm resistance gen cloned | This invention (see FIG. 27) |
| pLOI510 | Used as template for pdc and adhII PCR amplification | (Ohta et al., 1991) |

All plasmids and PCR products used in this work were analyzed by restriction patterns on agarose 1-1.2% gels electrophoresis.

Vegetal Tissues Hemicellulosic Hydrolysates such as Sugar Cane Bagasse

In the present invention sugar cane bagasse was used as an example, it was obtained from Emiliano Zapata's sugar mill in Zacatepec, Morelos, Mexico. The hydrolysis process for the production of fermentable sugars was carried out with sulfuric acid at different concentrations, temperature conditions, liquid-solid relation and time, as shown in the following section. Some hydrolysis tests were carried out in autoclave and most of them were carried out at pilot plant scale in a jacketed reactor.

The obtainment of sugar cane bagasse hemicellulosic hydrolysates was carried out in several stages: a) sugarcane bagasse homogenization b) dispersion of dilute sulfuric acid in the sugarcane bagasse at different liquid: solid ratios; c) selection of temperature, concentration and time for diluted acid hydrolysis treatment; d) obtaining of the hemicellulosic hydrolysates from bagasse; e) neutralization and detoxification of the hydrolysate by Ca(OH)$_2$ (30.5 g of Ca(OH)$_2$/L hydrolyzed) addition based on the milliequivalents needed to raise pH ~10-11 at room temperature, and f) concentration of the hydrolysate.

Hydrolysate Obtainment Conditions

Eight batches of hemicellulosic hydrolysates from sugarcane bagasse treated with sulfuric acid were conducted at pilot plant scale; treatments were divided into two groups: 1) Batches 1-4 and 2) Batches 5-8; furthermore, two batches were performed in a laboratory autoclave, The diluted-acid hydrolysis conditions for different groups in autoclave and pilot plant are indicated in Table 3.

TABLE 3

Group formation according to the acid: bagasse relation; hydrolysis time; temperature and acid concentration.

| Batch | Relation H$_2$SO$_4$:Bagasse | Time (h) | Temperature (° C.) | Acid concentration (%) |
|---|---|---|---|---|
| PILOT PLANT - HYDROLYZATOR GROUP 1 | | | | |
| 1 | 4:1 | 2 | 121 | 2 |
| 2 | 4:1 | 1 | 121 | 2 |
| 3 | 3:1 | 1 | 121 | 2 |
| 4 | 2:1 | 1 | 121 | 2 |
| GROUP 2 | | | | |
| 5 | 2:1 | 2 | 140 | 4 |
| 6 | 2:1 | 1 | 121 | 4 |
| 7 | 2:1 | 2 | 121 | 2 |
| 8 | 2:1 | 1 | 140 | 2 |
| AUTOCLAVE | | | | |
| 1 | 2:1 | 1 | 121 | 4 |
| 2 | 2:1 | 1 | 121 | 2 |

In group 1, an evaluation of the liquid-solid ratio ($H_2SO_4$: bagasse) and time on the formation of fermentable sugars was carried out, keeping the temperature and acid concentration constant. From these results, the relation 2:1 was maintained constant (group 2) and a factorial experimental design was carried out. The dependent variables were: temperature (121 and 140° C.), acid concentration (2 and 4%) and time (1 and 2 hours). The final experimental design was 4 experiments (Table 4)

TABLE 4

Diluted acid hydrolysis conditions of sugar cane bagasse

| $H_2SO_4$ (%) | T (° C.) | Time (hours) |
|---|---|---|
| 2 | 121 | 2 |
| 4 | 121 | 1 |
| 2 | 140 | 1 |
| 4 | 140 | 2 |

From the analysis of sugars in the hydrolysates, batches 4-8 were selected to be mixed, detoxified with Ca $(OH)_2$ at room temperature and concentrated in a Büchi Rotavapor 185 Ex, with the aim of increasing the concentration of sugars from ~29 g/L to 70 g/L. As a last step, solid waste removal was carried in a centrifuge tube MiniSharples CL-I-1. In order to avoid pollution problems the detoxified hydrolysates were stored in a cold room (4° C.), and before starting a test they were sterilized by filtration (0.2 μm).

Strains and Cell Bank In the present invention the *E. coli* JU15 strain was handled in some cases. The JU15 strain is an *E. coli* MG1655 derivative, which was obtained from the strain collection of the inventors of this invention. JU15 strain has disrupted the ethanol, formate-acetate and the succinate production pathways, and the ATP dependent xylose transport system. The inventors of the present invention assume that the route used to transport xylose is a symport. JU15 genotype is *E. coli* ΔadhE ΔpflB ΔxylFGH. In the cases where acetate was present in the culture medium, a JU15 derivative was used, the JU15A strain; this strain was adapted to grow faster and more efficiently in the presence of acetate. The JU15A strain was obtained from two serial cultures of JU15 strain in AM2 medium containing xylose and acetate as carbon sources.

Cell banks were generated, for both strains: JU15A JU15, from exponentially growing cells; one mL of each strain culture (JU15A and JU15) was frozen mixed with one mL of 80% glycerol into 2 mL cryovials, after mixing the culture with glycerol dry ice was used for a very fast freezing. With the purpose of having an inoculum with the same conditions throughout the study cryovials, with frozen cells, were stored at −70° C. in a ultra freezer.

Conditions and Culture Media
Inoculum: *Escherichia coli* JU15 y JU15A

In a mini-fermenter (fleaker) with 200 mL of mineral medium (AM2, Martinez et al., 2007) and 20 g/L of xylose or glucose, the latter only in cultures where glucose was used as the sole carbon source, cells were added from a glycerol cryovial. Temperature was controlled to 37° C. with a thermal bath and stirring was controlled to 100 rpm. The inoculum was incubated for 24 h until reaching an OD600 approx. 1.5-2. The cultures were inoculated by centrifugation (4000 rpm, 10 minutes at room temperature), to provide enough cells for an initial OD600 of approximately 0.1 (0037 gDCW/L) in the culture. Subsequently, cell pellets were transferred to each culture by suspending them in the culture media. The inoculum for JU15A strain was carried out under the same conditions as for JU15 strain, with the only difference that the culture medium contained 20 g/L xylose and 1.48 g/L acetate in 200 mL of mineral medium (AM2).

Culture Media and Control Cultures

The AM2 medium composition for fleakers cultures (Martinez et. al., 2007) was: 2.63 g/L $(NH_4)_2HPO_4$, 0.87 g/L $NH_4H_2PO_4$, 1.0 mL/L $MgSO_4 7H_2O$ (1M), 1.5 mL/L trace elements, 1.0 mL/L KCl (2M), 1.0 mL/L Betaine HCl (1M), 100 mg/L citric acid. The medium was supplemented with different concentrations of xylose, glucose, arabinose and/or sodium acetate. The trace element solution contains per liter: 1.6 g $FeCl_3$, 0.2 g $CoCl_2.6H_2O$, 0.1 g $CuCl_2$, 0.2 g $ZnCl_2 4H_2O$, 0.2 g $Na_2MoO_4$, 0.05 g $H_3BO_3$ y 0.33 g $MnCl_2.4H_2O$.

Hydrolyzed Supplemented Cultures Labeled from A-F

In cultures AF, elements of the AM2 medium were used in different proportions but at the same concentration mentioned above. The Table 5 summarizes the proportions of each of these elements, using the following abbreviations Salts: $(NH_4)_2HPO_4$ and $NH_4H_2PO_4$, Mg, $MgSO_4.7H_2O$; Bet: betaine HCl; T.E. trace elements, C.A.: citric acid and KCl: KCl. The A to F cultures media were supplemented with 50 g/L xylose, 6.7 g/L glucose, 3.3 g/L arabinose and 1.48 g/L sodium acetate.

TABLE 5

AM2 medium composition used in A-F cultures

| (A) | (B) | (C) | (D) | (E) | (F) |
|---|---|---|---|---|---|
| 1X Bet | 1X Bet | 1X Bet | 1X Bet | 1X Bet | 1X Bet |
| 1X C.A. | 1X C.A. | 1X C.A. | 1X C.A. | — | — |
| 0.25X Salts | 0.25X Salts | 0.25X Salts | 0.25X Salts | 0.125X Salts | — |
| 0.25X KCl | 0.25X KCl | 0.25X KCl | — | — | — |
| 0.25X Mg | 0.25X Mg | — | — | — | — |
| 0.25X T.E. | — | 0.25X T.E. | — | — | — |

Culture Conditions
Fleakers (250 mL Mini-Fermentors)

Anaerobic cultures were carried out in fleakers (mini-fermentors) (Beall et al., 1991) with a 200 mL working volume. Temperature was controlled to 37° C. with a thermal bath and stirring was controlled to 100 rpm. The pH was controlled in the range of 6.6 to 7.0 with the automating addition of KOH 2N or 4N. The stirring was maintained at 100 rpm using a magnetic cross stirrer with a diameter of 2.54 cm. All experiments were carried out at least by duplicate and in most of the cases by triplicate.

The fleaker system used in the present work has the following elements: a) 6 mini-fermentors (300 mL) with a magnetic stirrer; b) a temperature control consisting in a thermocycler and a water bath; c) a pH controller, consisting of six automated controllers with valves used to release the base, and six pH electrodes: d) stirring control integrated by a magnetic plate (100-850 rpm).

10 L Fermenter

The anaerobic cultures in a greater volume where carried out in a pilot scale 10 L fermentor (Microferm, New Brunswick, N.J., USA). The controlled conditions of pH, temperature and stirring speed were kept in the values 6.6-7.0, 37° C. and 240 rpm respectively. The pH was controlled with the addition of 4N KOH base and the temperature was controlled with an internal coil. A marine propeller impeller was used to keep the agitation.

Analytic Methods

Spectrophotometric Determination of the Cell Concentration

The optical density was measured at 600 nm ($OD_{600}$) in a spectrophotometer Beckman (DU-70) (Beckman instrument, Inc. Fullerton, Calif., USA) and it was converted to dry cellular weight (DCW) according to a calibration curve: 1 $OD_{600}$ equal to 0.37 $g_{DCW}$/L. All the samples were centrifuged (5,000 rpm at room temperature) the cell pellet was discarded and the supernatant was frozen for latter analyzes.

Viable Count (CFU)

The number of cells in the cultures with hydrolysates, where the medium did not allow measuring the optical density was measured by viable count of colony forming units (CFU) and converted to a number of cells per milliliter (cells/mL) by considering the dilution respectively. Similarly, all samples were centrifuged (5,000 rpm at room temperature) separating the supernatant for further analysis.

Determination of Organic Acids and Sugars

Calculation from the Base KOH Consumption (Organic Acids)

The base consumption used for pH control during a growth kinetic gives an approximate value of the organic acid (lactic acid) present in the medium. The calculation for the determination of the organic acid concentration ($C_A$) is made using the following known data: base concentration ($C_B$); consumed base volume ($V_{BA}$); initial working volume in the mini-fermentor ($V_T$). and the equation 1:

$$C_A = \frac{(C_C)(V_{BA})}{V_T} \qquad \text{Equation 1}$$

where:

$C_A$ and $C_B$, are molar concentrations (mol/L)

$V_{BA}$ and $V_T$, are in mL

Quantification of Organic Acids and Sugars by High Performance Liquid Chromatography (HPLC)

The determination of organic acids and sugars by HPLC was carried out by isocratic chromatography with a solution of 5 mM $H_2SO_4$ as mobile phase at a flow rate of 0.5 mL/min in an Aminex HPX-87H column (Biorad) at 50° C. The detection of the separated compounds was carried out simultaneously with a diode array detector (Waters 996) and a refractive index detector (Waters 410). The data processing and analysis was performed with the "Millennium" software (Version 3.01 Waters). The internal and external temperatures of the column were adjusted to 45 and 50° C. respectively. The supernatants of the samples to be analyzed were filtered with 0.45 μm membrane and automatically injected using the autoinjector (Waters 717). For confirmation of the sugars and the products analyzed HPLC standards of xylose, glucose, arabinose, sodium acetate and organic acids were injected. The data obtained from the concentrations of each of the analyzed compounds were calculated with a calibration method-Interpolation of the same software.

Kinetic Parameter Evaluation of the Fermentation Processes.

The evaluated parameters were: specific growth rate (μ); cell mass/substrate yield ($Y_{X/S}$); product/substrate yield ($Y_{P/S}$); product/cell mass yield ($Y_{P/X}$); volumetric productivity of the desired product (P); specific substrate consumption rate ($q_S$); specific production rate ($q_P$). All of them where calculated during the exponential growth phase of each bacterial strain generated in the present invention. In order to calculate the kinetic parameters, the dilution factor caused for the addition of the base for pH control was considered. The dilution factor ($F_D$) is given by the amount of added base to the initial working volume (Equation 2). The way to correct the substrate, product and cell mass measurements is multiplying by the dilution factor.

$$F_D = \frac{(V_I + V_{BA})}{V_I} \qquad \text{Equation 2}$$

where:

$V_I$, is the initial working volume in mL $V_{BA}$, is the volume of added base used for pH control in mL

EXAMPLES

In the following examples, the invention is better illustrated, although its possible uses extend beyond these examples.

Inactivation of Fermentative Genes in the Bacterial Strains

The microorganisms, plasmids and primers used in the present invention are shown in the MATERIALS AND METHODS section or in the SEQUENCE LIST appendix.

Example 1 pflB Gene Suppression

Figure 4:
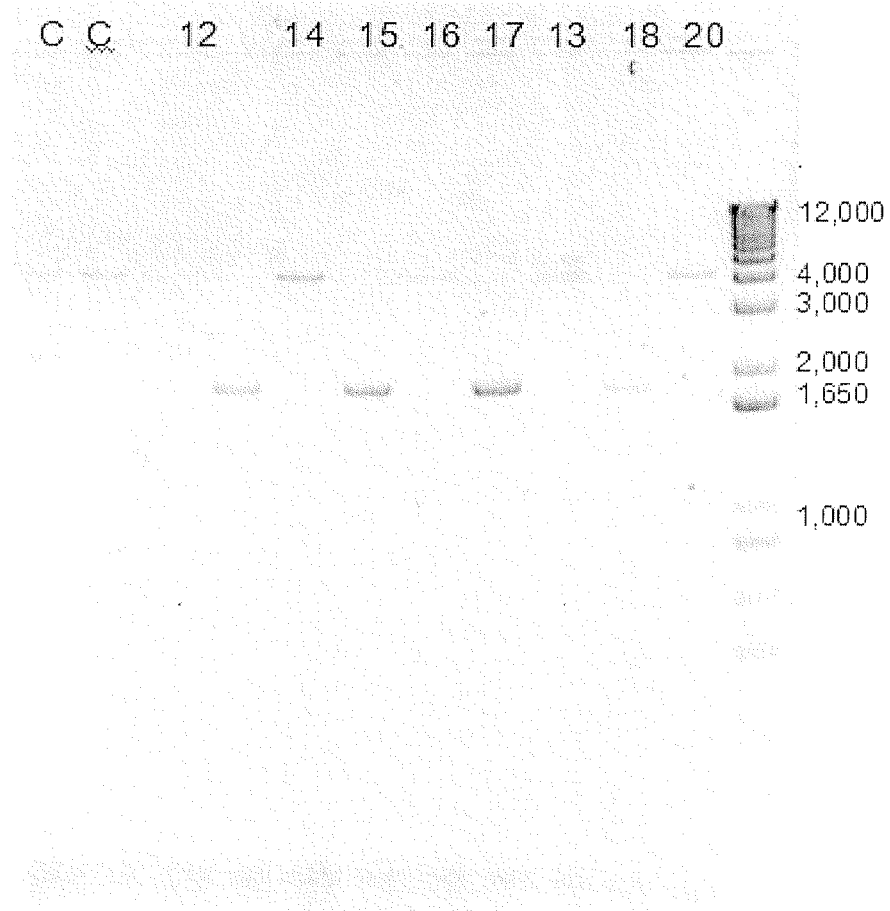
FIG. 4. Image that shows an agarose gel with the PCR products of possible ΔpflB. Mutants (Lane heading represents the colony number) (C: control). Lanes 12, 15, 17, 18 product corresponds to the size of the inactivated gene. Lanes 13, 14, and 16 corresponds to the size of the intact gene. The numbers represent the size of the product in base pairs.

As the first part of the present invention, the gene pflB of the E. coli strain MG1655 was suppressed using the plasmid PKO3-pflB (Lara et al., 2006). The pflB suppression was verified with PCR (FIG. 4) using the parent strain as a control and another mutant strain of E. coli, ΔpflB W3110.

Figure 5:
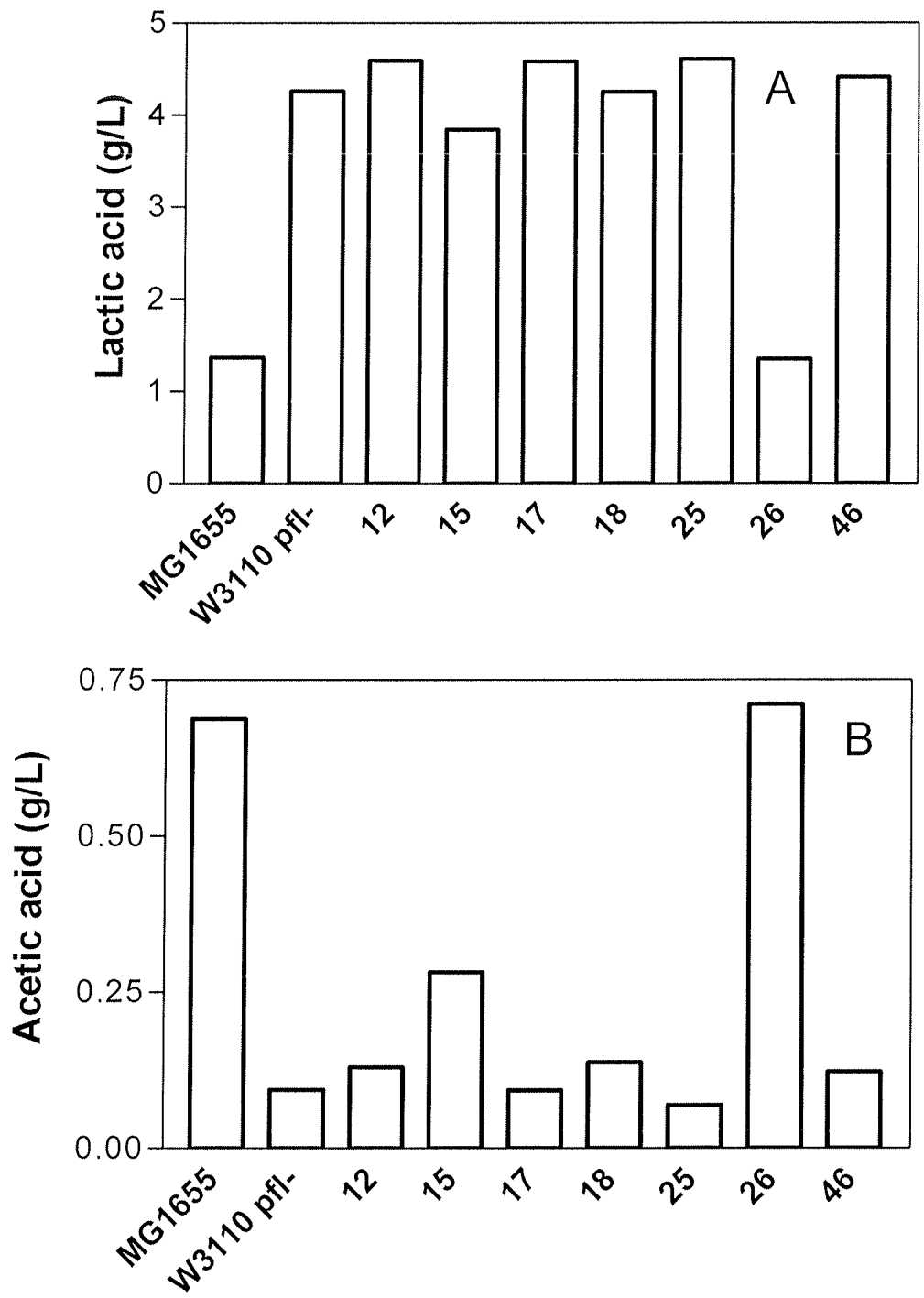
FIG. 5. Illustrates the production of: A) Lactic acid and B) Acetic acid of the selected colonies (12, 15, 17, 18, 25, 26, 46), as well as W3110 pfl⁻ and MG1655 strains.
Figure 6:
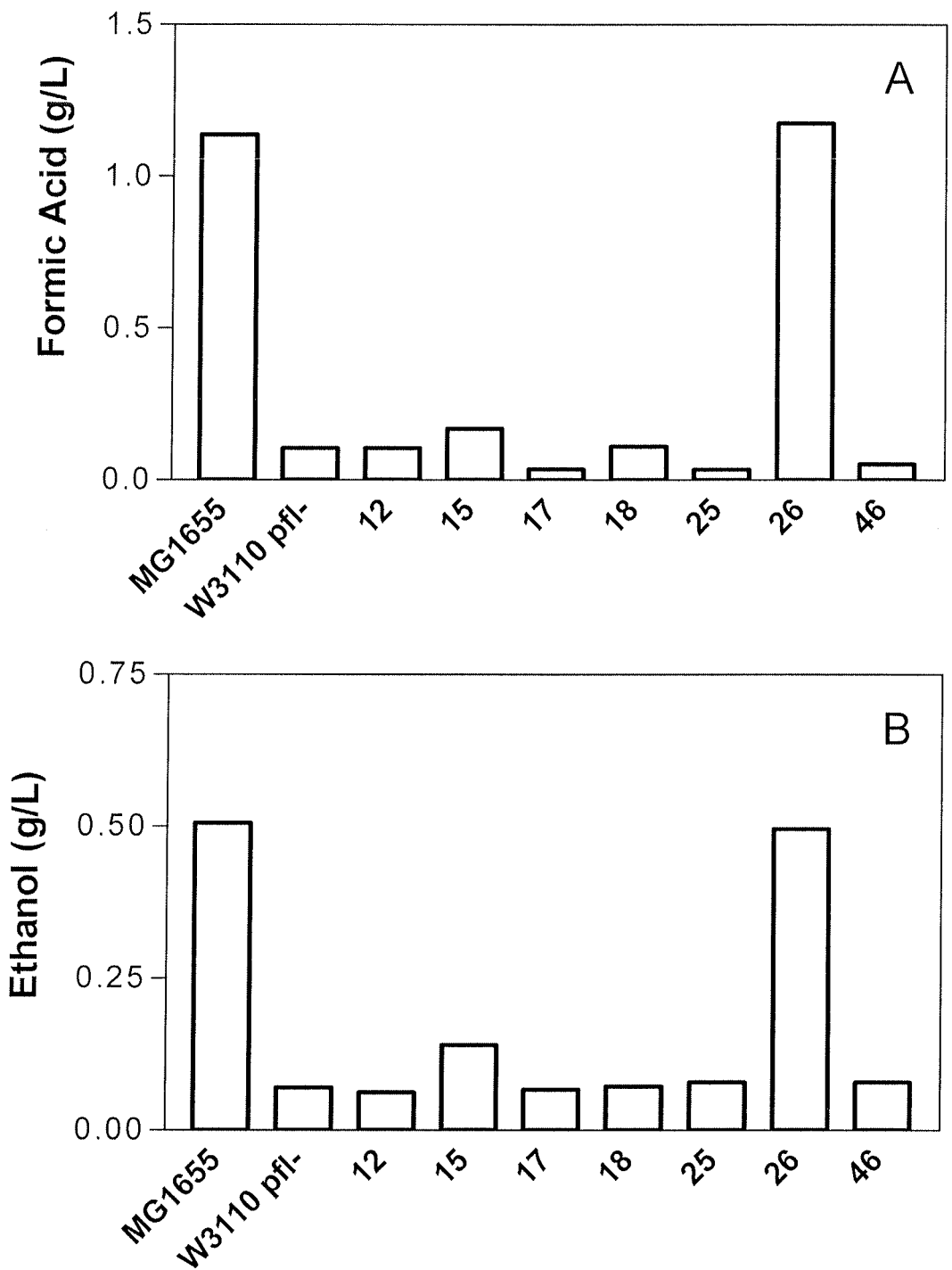
FIG. 6. Illustrates the production of: A) Formic acid and B) Ethanol of the selected colonies (12, 15, 17, 18, 25, 26, 46), as well as W3110 pfl⁻ and MG1655 strains.

The expected PCR product in the mutants corresponds to 1.7 Kbp, or to 4.5 Kbp in false positives, which is the size corresponding to the amplification of the intact gene. From the analysis of different gels, 7 mutants were selected. From these strains, cultures were grown in test tubes in AM2 media with 10 g/L of glucose and at 37° C. to verify the fermentation products after 24 h (FIGS. 5 and 6).

The phenotype observed in the colonies that have pflB suppression was a noticeable decrease in the products that are obtained from a reaction catalyzed by pyruvate formate lyase, that is, formic and acetic acids and ethanol, with a concurrent substantial increase in the production of lactic acid. As is seen in FIGS. 5 and 6, with the exception of colony number 26 (false positive), this phenotype is found in all of the colonies analyzed.

Example 2 adhE Gene Suppression

To perform the adhE gene suppression, a PCR product with regions homologous to this gene was obtained with the Adh Forw primers (SEQ. ID NO: 1) and Adh Rev primers (SEQ. ID NO: 2), and the plasmid pKD4 was used as a template (Datsenko and Wanner 2000). The product was electroporated into cells induced with arabinose and with a co-plasmid (pKD46). Several colonies resistant to kanamycin were obtained and analyzed with PCR with the adhck forward and reverse primers (SEQ. ID NO: 3 and SEQ. ID NO: 4, respectively), which amplify a 3.0-Kbp product corresponding to the regions 200 by downstream and upstream plus the adhE (2.6-Kbp) gene. Following suppression, a 1.9-Kbp product, corresponding to the kanamycin-resistance cassette and the adjacent regions already mentioned, is obtained.

Figure 7:
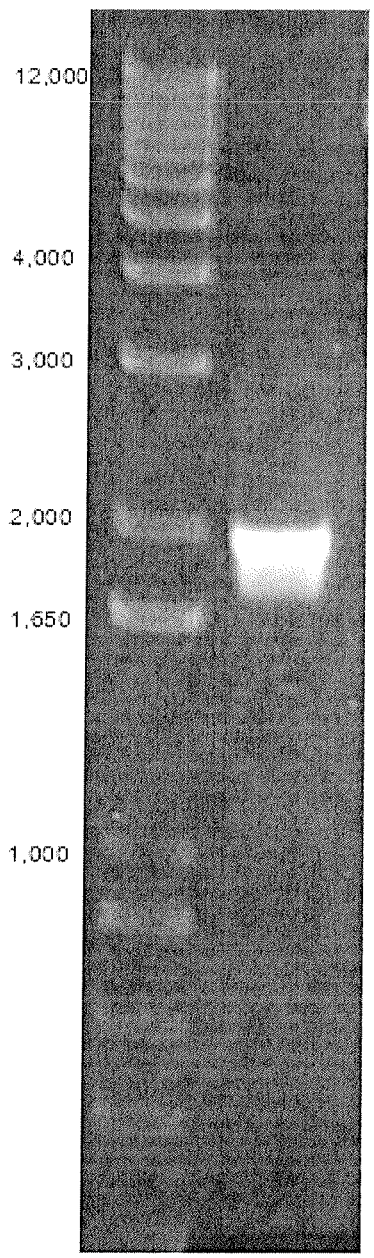
FIG. 7. Picture that shows an agarose gel with a 1.9 Kbp PCR product that corresponds to the inactivated adhE gene. The numbers represent the size of the product in base pairs.

FIG. 7 shows the 1.9-Kbp fragment obtained by adhE gene suppression, which yielded the *E. coli* strain MG1655 ΔpflB ΔadhE that was labeled as CL1 in the present invention.

Example 3 frd Gene Suppression

To carry out the frd gene suppression, a PCR product with regions homologous to target gene was obtained using the frd Forw and frd Rev primers (SEQ. ID NO: 5 and SEQ. ID NO: 6, respectively) and the plasmid pKD4 as a template (Datzenko and Wanner 2001). This product was electroporated into cells induced with arabinose and with the co-plasmid (pKD46). Several colonies resistant to kanamycin were obtained and analyzed with PCR with the frdck forward and reverse primers (SEQ. ID NO: 7 and SEQ. ID NO: 8, respectively), which amplify a 1.9-Kbp product that corresponds to regions 50 bp downstream and upstream, plus the frd gene (1.8-Kbp). Following suppression, a 1.6-Kbp product is obtained, corresponding to the kanamycin-resistance cassette and the adjacent regions already mentioned.

The *E. coli* strain obtained, which was resistant to kanamycin, was transformed with the pCP20 plasmid carrying the FLP recombinase gene. The latter was grown in petri dishes with ampicillin, yielding isolated colonies. The colonies were selected for the loss of kanamycin resistance. The colonies obtained that were sensitive to kanamycin were evaluated by PCR to verify the suppression. The PCR yielded a product near 200 bp, which corresponds to the sites adjacent to the gene and to the FRT sequences that recognize FLP recombinase. This process yielded the strain labeled as CL3 (*E. coli* MG1655 ΔpflB adhE Δfrd) in the present invention.

Example 4

Phenotype Characterization of CL3

Figure 8:
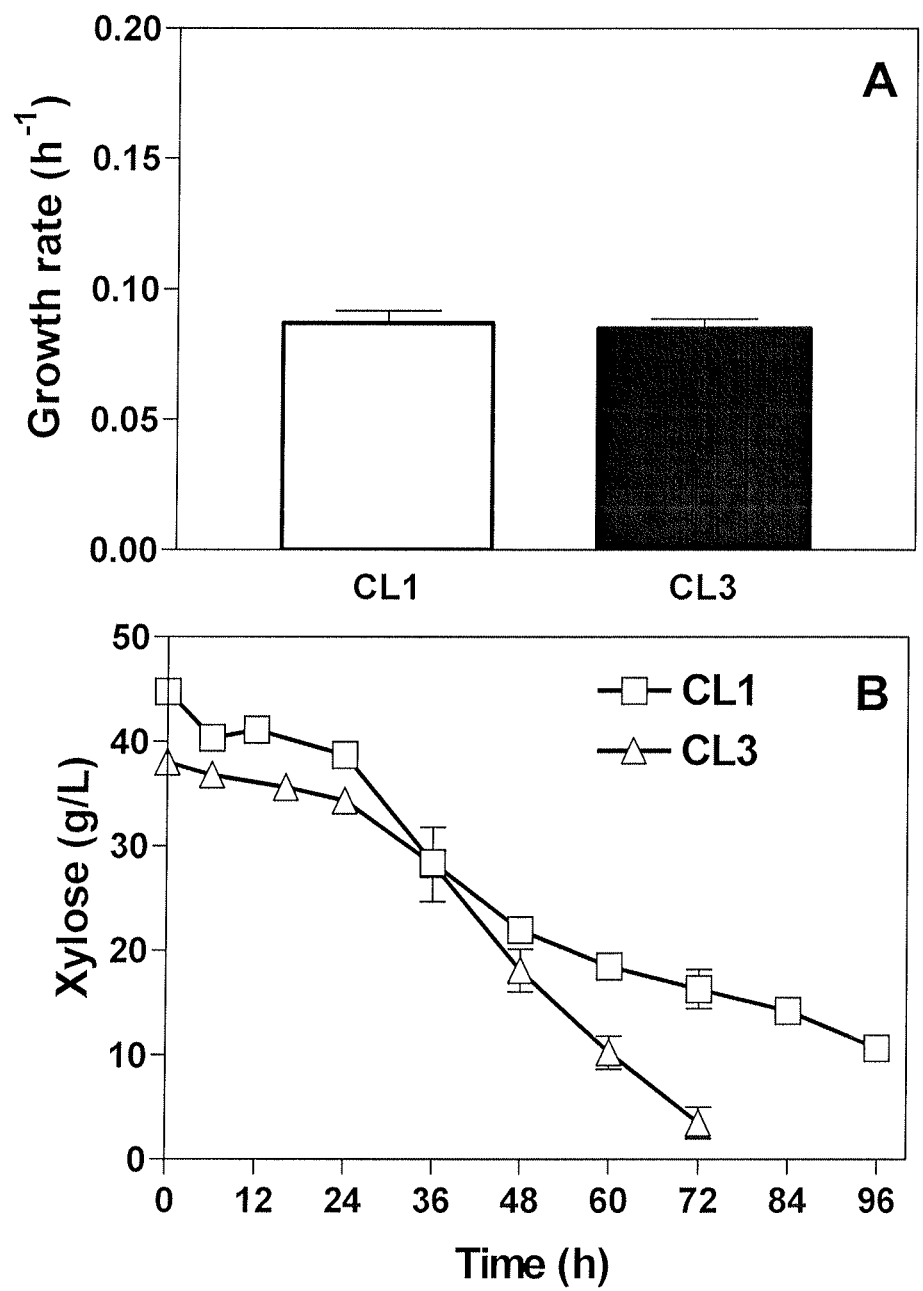
FIG. 8. Graphics that show a comparison of strains CL3 and CL1 in their: A) Growth rate and B) xylose consumption kinetics.
Figure 9:
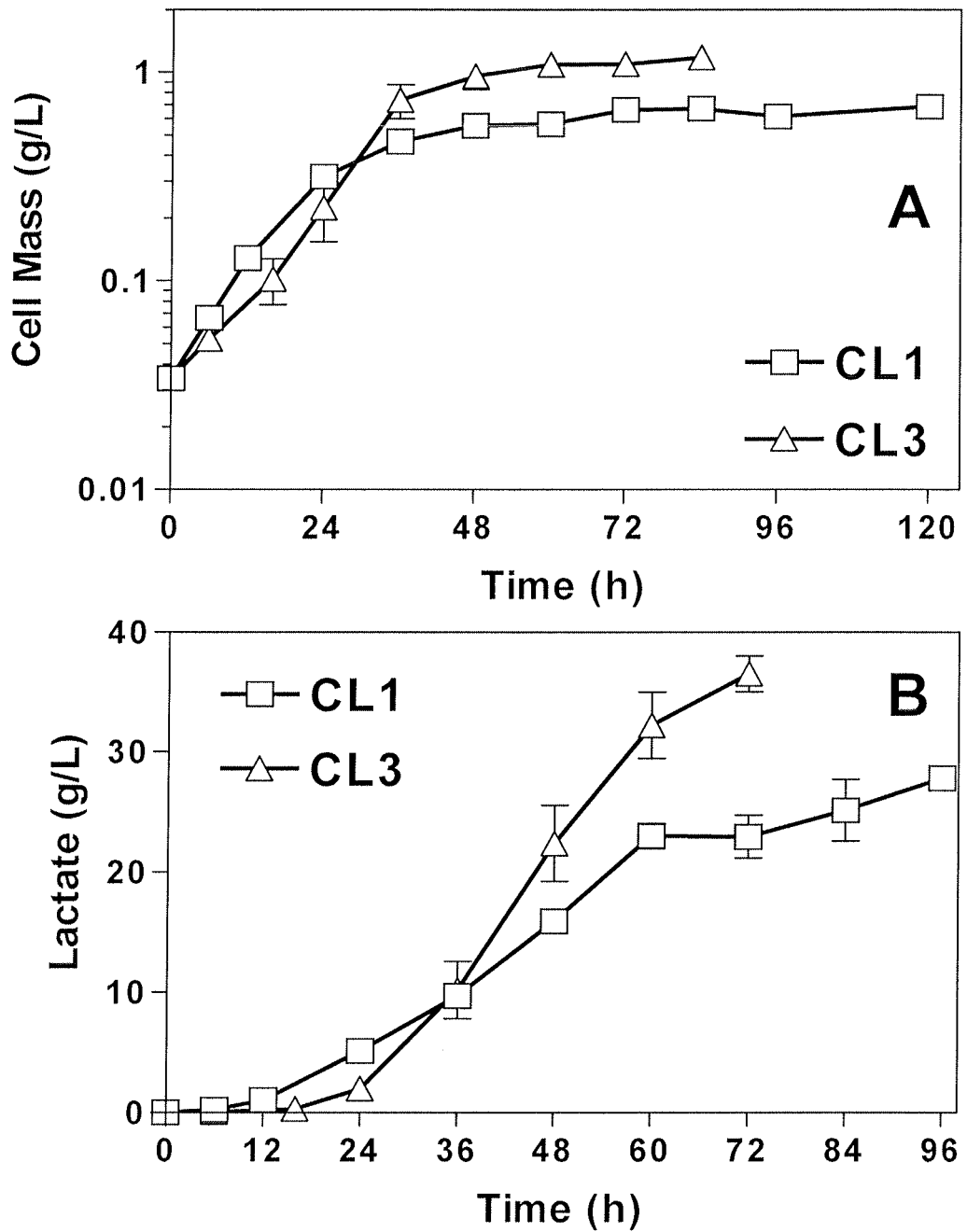
FIG. 9. Graphics that show a comparison of strains CL3 and CL1 in their: A) Growth and B) lactate production kinetics.

To characterize the CL3 strain (*E. coli* MG1655 ΔpflB ΔadhE Δfrd) obtained by Utrilla et al., 2009, cultures were cultivated in mini-fermentors with controlled pH in AM2 medium, which has a low salt content and is optimized for the anaerobic growth of *E. coli* (Martinez et al., 2007), and with 40 g/L of xylose or glucose. The specific growth rate and the production level of lactate, ethanol, acetate, formate and succinate were obtained. Strain CL1, from which strain CL3 is derived, was characterized in mineral medium with xylose or glucose at a concentration of 40 g/L. The CL3 strain in AM2 medium with xylose and glucose has a growth rate similar to that obtained for CL1 in mineral medium with xylose or glucose, but there is an increase in cell mass production of 38% and 14% in xylose and glucose, respectively. In contrast to the other mutant pfl strains that have been reported (Zhou et al. 2003a), the CL1 and CL3 strains have the capacity of growing at 0.22 $h^{-1}$. This increase in cell mass production had an effect on the consumption of sugar and on the lactate productivity. In glucose, 40 g/L of sugar was consumed in approximately 24 h, and a lactate yield close to the theoretical value (1 g of lactate/g of glucose) was obtained, equivalent to a volumetric productivity of 1.66 g of lactate/h (FIG. 8). In xylose, the 40 g/L of sugar was consumed in approximately 72 h by the CL3 strain in AM2 medium, in contrast to the findings with the CL1 strain in mineral medium. In this case, after 96 h, approximately 10 g of xylose remained (FIG. 8). For both sugars, it was found that frd gene suppression eliminated succinate production, resulting in D-lactate (FIG. 9) and acetate as the only products of the CL3 strain. Acetate was found in concentrations below 2 g/L in the medium with glucose and below 5 g/L in the medium with xylose at the end of the fermentation (data not shown).

Example 5

Suppression of the ATP-Dependent Xylose Transport System

Figure 10:
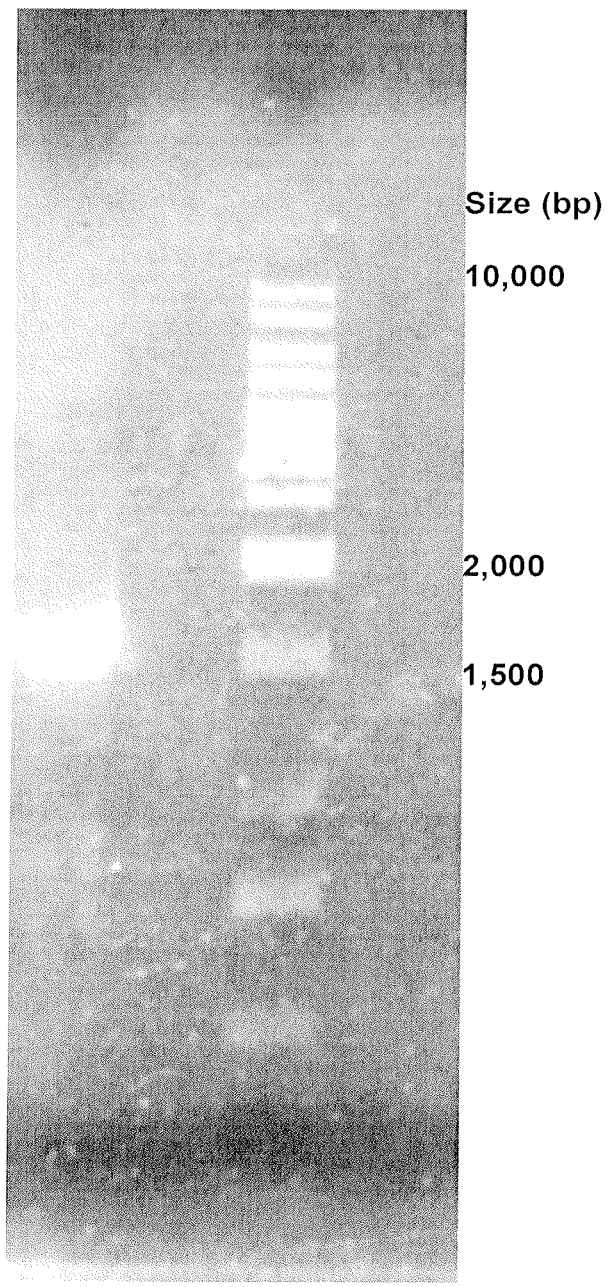
FIG. 10. Picture that shows an agarose gel with a PCR product that corresponds to the inactivated xylFGH genes.

The inventors of the present work suppressed the ATP-dependent xylose transport system (xylF, xylG and xylH genes) using the technique of inactivation of chromosomal genes by a PCR product (Datsenko and Wanner, 2000). The inventors obtained a PCR product of 1.6 Kbp using the Xyl Forw and Xyl Rev primers (SEQ. ID NO: 9 and SEQ. ID NO: 10, respectively) and the plasmid pKD4 as a template. This product corresponded to the kanamycin cassette with regions homologous to the genes to be suppressed. The xylck Forw and xylck Rev primers (SEQ. ID NO: 11 and SEQ. ID NO: 12, respectively) were designed to amplify the regions adjacent to the xylFGH genes, which have a size of 3.7 Kbp in the wild strain and 1.6 in the suppressed strain (FIG. 10).

Figure 11:
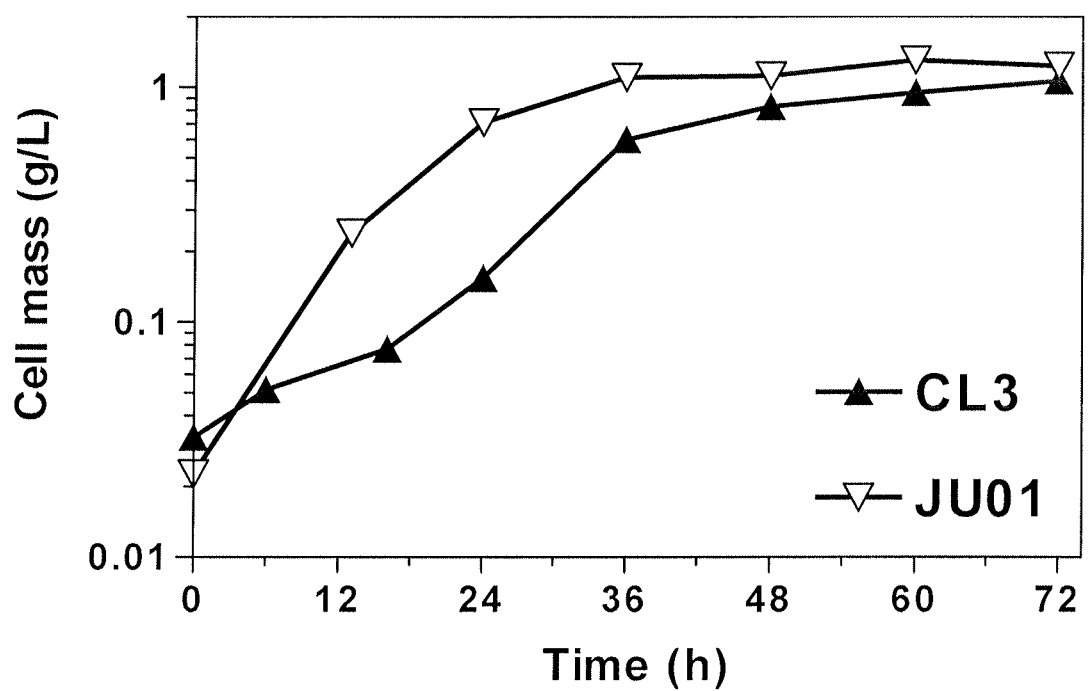
FIG. 11. Growth kinetics of strains JU01 and CL3 in xylose 40 g/L AM2 medium

The inventors obtained the strain labeled in the present invention as JU01 (*E. coli* MG1655 ΔpflB ΔadhE Δfrd ΔxylFGH), which was tested in AM2 medium with 40 g/L of xylose. It was found that JU01 grows 37% faster than the CL3 strain (p=0.14 $h^{-1}$) (FIG. 11) and completed the fermentation of 40 g/L of xylose in 72 h. This result suggests that a higher yield of ATP per mole of metabolized xylose can be obtained when using alternative transport systems that do not depend on ATP (most likely XylE). However, compared with the results obtained with glucose, JU01 takes three times the amount of time to consume 40 g/L of xylose, and the volumetric productivity of organic acids is affected, producing a third of what is obtained in glucose. This result indicates that improving the xylose consumption rate can potentially help obtain lactate production velocities similar to those obtained with glucose.

Example 6

Figure 12:
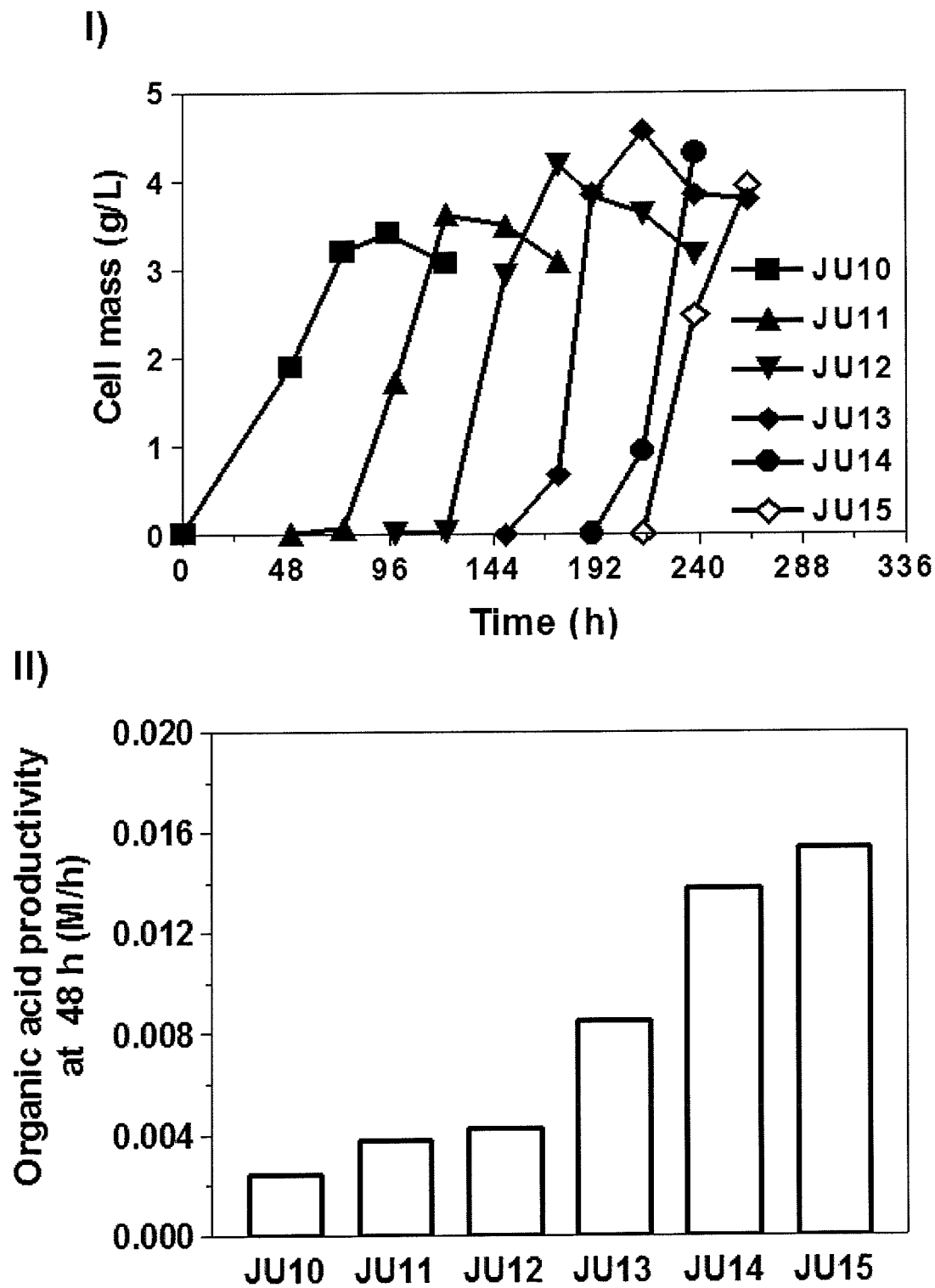
FIG. 12. Graphic that shows: I) the growth kinetics during the adaptive evolution of strain JU01 in 120 g/L xylose AM2 medium and II) a bar graphic that show the organic acid productivity at 48 h.

Adaptive Evolution of the JU01 Strain and Optimization of the Production pH for the Derived Strain Based on the statements in the previous paragraph, the developers of this invention subjected the JU01 strain to a process of adaptive evolution in AM2 medium with 40 g/L of xylose (as the only carbon source); nine transfers were performed, and none of these was able to significantly increase the growth rate or the organic acid production as determined through the consumption of the base used to control the pH. A concentration of 120 g/L of xylose was used to increase the selection pressure and to obtain mutants with a better capacity to grow in xylose. Six transfers were conducted, and in the present invention, the growth capabilities and organic acid production of the JU01 strain were improved (FIG. 12), yielding a new strain of *E. coli* labeled in the present invention as JU15.

Figure 13:
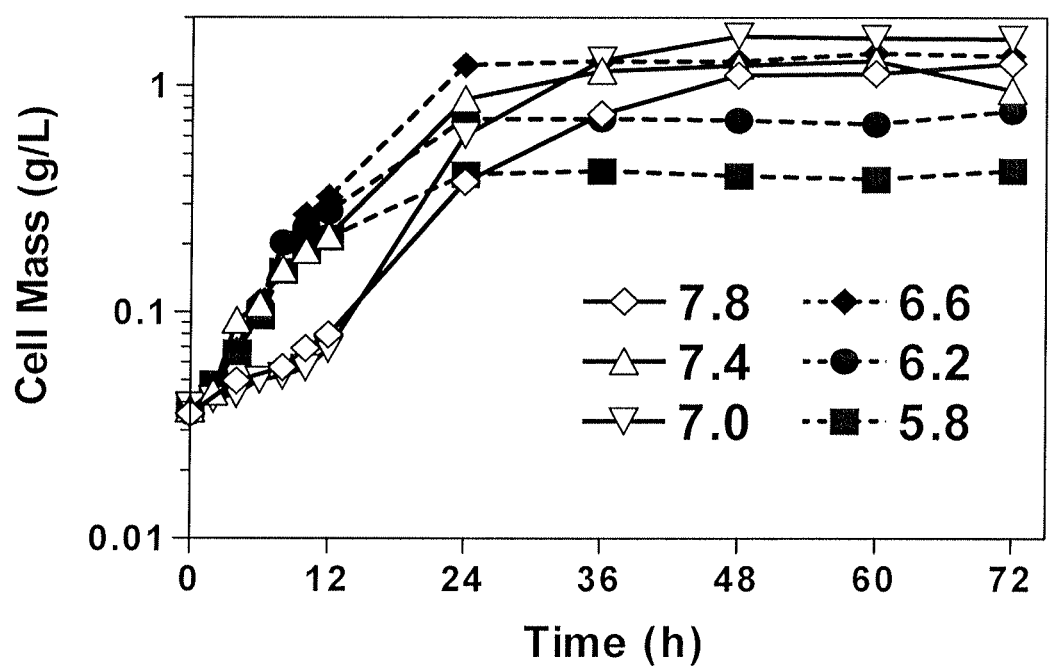
FIG. 13. Illustrates the effect of the pH in the growth of strain JU15.

There are reports in which fermentations are performed at different pH values for lactic acid production, using strains derived from *E. coli* B and *E. coli* K12 (Dien et al., 2001). However, in the case of *E. coli* JU15, because it is a new strain, its behavior was unknown when fermenting at different pH values. For this reason, the inventors characterized the fermenting process at the pH values 5.8, 6.2, 6.6, 7.0, 7.4 and 7.8 in mineral medium enriched with 6% xylose and in fermentation processes lasting 72 h to obtain the optimal pH conditions for the best growth of the strain. FIG. 13 shows the behavior obtained when the pH is varied, and Table 6 summarizes the experimental kinetic parameters.

As seen in Table 6, one of the optimal pH values for the process developed in the present invention is 7.0, but lactate can be produced without a problem from a value of 5.8 up to 7.8.

TABLE 6

Kinetic parameters of *E. coli* JU15 strain at different pH values

| pH | *X (g/L) | $X_{max}$ (g/L) | *$\mu$ ($h^{-1}$) | *$q_P$ ($g_{lactate}/g_{cell\ mass} \cdot h$) | P ($g_{lactate}/L \cdot h$) |
|---|---|---|---|---|---|
| 7.8 | 0.08 | 1.25 | 0.068 | 2.06 | 0.66 |
| 7.4 | 0.22 | 0.96 | 0.147 | 2.57 | 0.68 |
| 7.0 | 0.07 | 1.61 | 0.150 | 8.97 | 0.73 |
| 6.6 | 0.32 | 1.36 | 0.175 | 3.07 | 0.71 |
| 6.2 | 0.28 | 0.77 | 0.171 | 2.85 | 0.50 |
| 5.8 | 0.21 | 0.42 | 0.142 | 2.20 | 0.23 |

*Values obtained during exponential growth phase

Example 7

Figure 14:
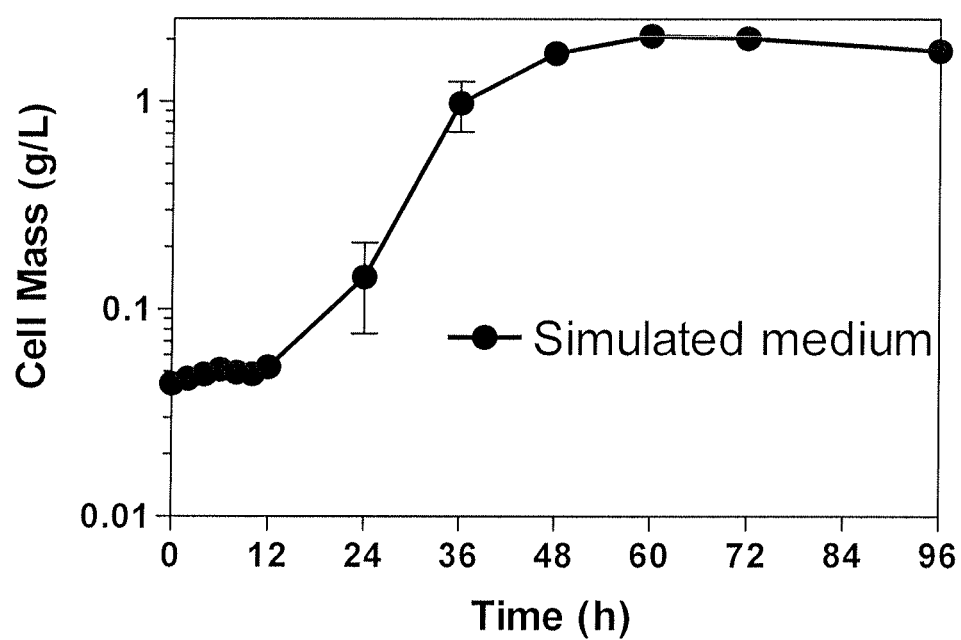
FIG. 14. Growth kinetics of *E. coli* strain JU15 on simulated hydrolysate 1.
Figure 15:
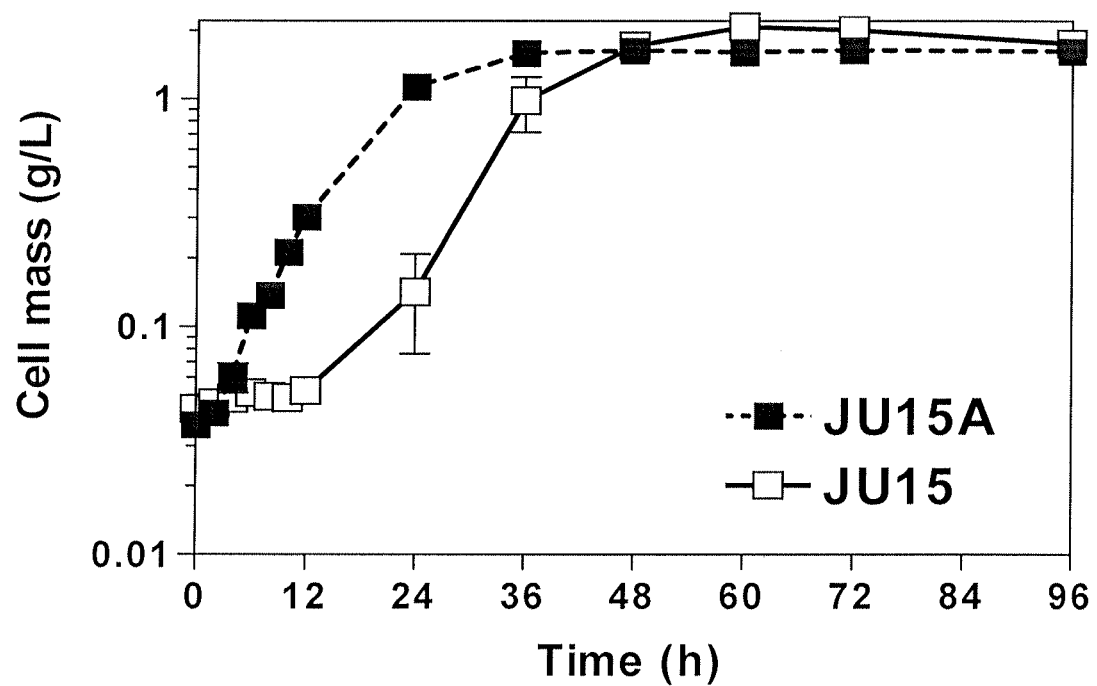
FIG. 15. Growth kinetics of *E. coli* strains JU15 and JU15A on simulated hydrolysates.

Characterization of *E. coli* JU15 and JU15A in Mineral Medium Simulating Hydrolysate Composition For the present invention, the new strain JU15 has also been characterized in a simulated vegetable tissue hydrolysate, numbering it as 1 (simulated hydrolysate 1). For this experiment, the mineral medium AM2 was used with the addition of other major components in the following concentrations: xylose 50 g/L, glucose 6.7 g/L, arabinose 3.3 g/L and acetic acid 1.1 g/L. The total sugar concentration was 60 g/L, and the pH value started at 6.6 and changed to pH 7.0 at the start of fermentation. In this culture medium, it is seen that the strain had a dampened growth phase of 12 h because of the presence of acetic acid, causing a possible growth inhibition effect for the JU15 strain (FIG. 14). This strain finally reached a specific growth rate ($\mu$) of 0.12 $h^{-1}$ and a $q_P$ of 1.93 $g_{lactate}/g_{cell\ mass} \cdot h$ after 96 h. Due to the dampened growth phase, the inventors carried out two passes in the presence of acetate to improve the growth of the strain, by which process another new strain was obtained, named JU15A in the present invention. To illustrate its behavior, another control culture was performed with this evolved strain, adding sodium acetate to the inoculum. The behavior obtained is shown in FIG. 15, demonstrating that the inventors eliminated the lag phase that the strain JU15 normally exhibits, thereby demonstrating better tolerance to acetic acid than the other strains previously reported (Lawford and Rousseau, 1992). Because this result contrasts with the behavior shown by *E. coli* K12, which was inhibited by the addition of 35 mM of sodium acetate (Lawford and Rousseau, 1992), this observation shows that, despite the microorganism being the same (*E. coli*), the difference between strains indicates tolerance to inhibition by acetic acid.

Figure 16:
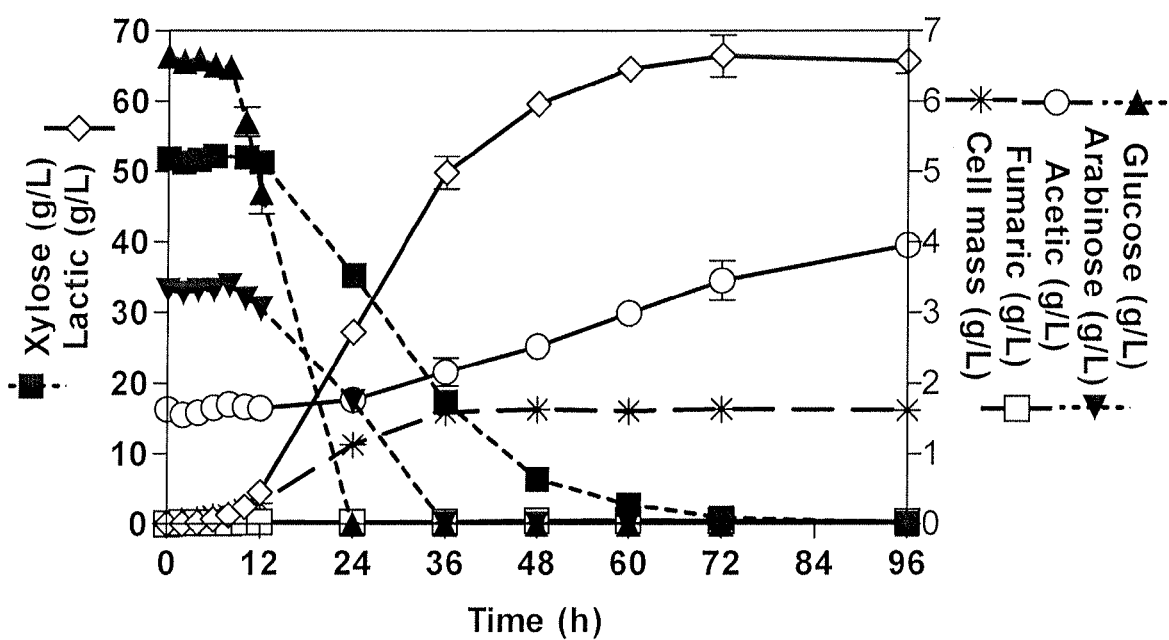
FIG. 16. Growth kinetics of *E. coli* strain JU15A on simulated hydrolysate 1.

For the new strain JU15A, neither the $q_P$ nor the productivity (P) was affected by the addition of 1.1 g/L of acetic acid to the simulated hydrolysate 1 (AM2 medium with added xylose, glucose and arabinose) (see Table 7). FIG. 16 shows the kinetics of *E. coli* JU15A in the simulated hydrolysate 1, which was conducted by the inventors of the present invention at 100 rpm, with the pH maintained in the interval 6.6-7.0 and at a temperature of 37° C. Under these conditions and with the evolved strain, the specific growth rate increased 1.5 times. The volumetric productivity (P, $g_{lactate}/L/h$) was obtained by dividing the final concentration of lactic acid by the total time of the fermentation. The final product yield was determined according to the maximum obtained lactate concentration divided by the total sugar concentration consumed in the media, yielding in this case 100% of the theoretical value. Table 7 summarizes the kinetic parameters obtained in the present invention.

TABLE 7

Kinetic parameters of the evaluation of *E. coli* JU15A in hydrolyzed simulated medium 1.

| *$\mu$ ($h^{-1}$) | *$q_S$ | *$q_P$ | *$Y_{X/S}$ | $Y_{P/S}$ | P | $X_{max}$ (g/L) | $X_{max}$ (CFU/mL) |
|---|---|---|---|---|---|---|---|
| 0.18 | 1.80 | 3.27 | 0.097 | 1.06 | 0.70 | 1.64 | $4.8 \times 10^{10}$ |

Figure 17:
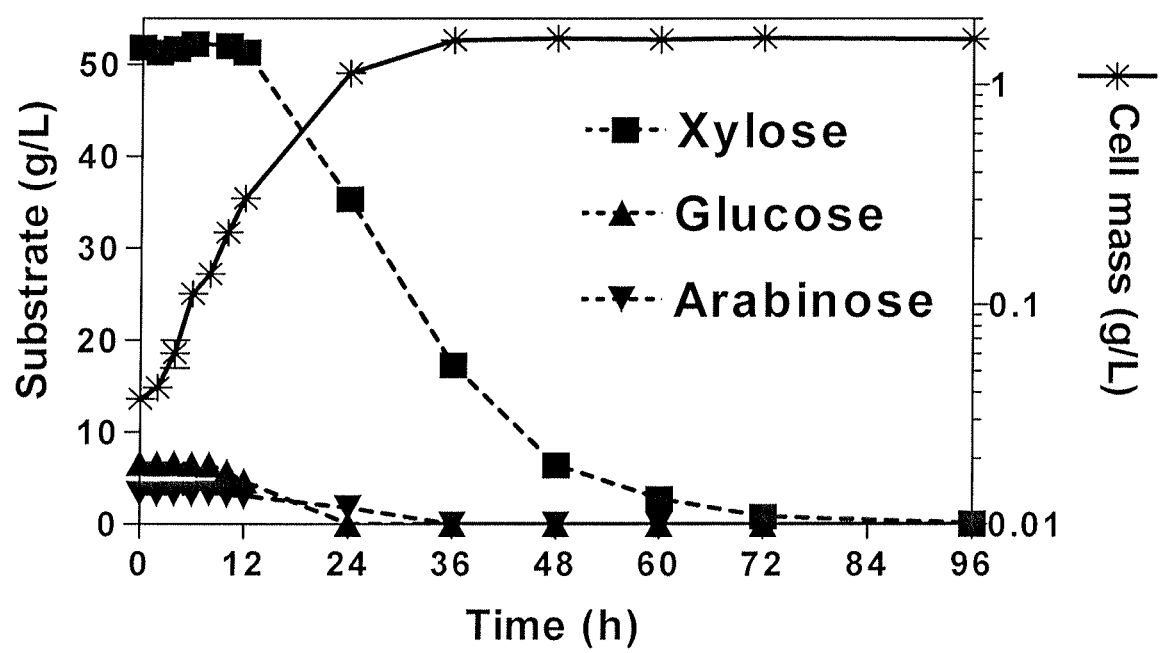
FIG. 17. Graphic that shows the growth and substrate consumption kinetics of JU15A strain on simulated hydrolysates 1

$Y_{P/S}$: $g_{lactate}/g_{sugar}$;
$Y_{X/S}$: $g_{cell\ mass}/g_{sugar}$;
$q_P$: $g_{lactate}/g_{cell\ mass} \cdot h$;
$q_S$: $g_{sugar}/g_{cell\ mass} \cdot h$; and
P: $g_{lactate}/L \cdot h$.
*Values obtained during exponential growth phase Looking at FIGS. 16 and 17, the simultaneous consumption of two carbon sources can be observed in the first instance: glucose-arabinose and afterward, with glucose exhausted, the simultaneous consumption of xylose-arabinose. The formation of cell mass shows that the phenomenon of catabolic repression by the preference for one carbon source does not occur, and the behavior does not show diauxic (two-stage) growth. Similarly, FIG. 16 shows that acetate was not consumed, which is why this compound is not considered to be a carbon source for the new *E. coli* JU15A strain. In the fermentation process of the present invention, there is only a total production of 2.3 g/L of acetic acid, considering the initial and final concentration at the end of the fermentation.

Additionally, the inventors of the present invention determined that in fermentations with the new strain JU15A, the carbon sources (xylose, glucose and arabinose) were totally consumed and that the lactate production achieved 100% of the theoretical yield. There was no acetate consumption, but this compound was produced after 24 h. There was no formation of ethanol or formate, and trace concentrations of fumarate were detected.

When comparing the new strains JU15 and JU15A, the effect of acetate is seen as causing a larger dampened growth phase, which results in a decrease of the specific growth rate and productivity. Acetic acid is typically used as an antimicrobial agent in the food industry because it is known for its inhibitory effect on bacteria and yeasts. This compound inhibits growth because of its ability to travel freely across the membrane, acidifying the cytoplasm, collapsing the transmembrane pH gradient and destabilizing homeostasis with respect to the intracellular pH.

Figure 18:
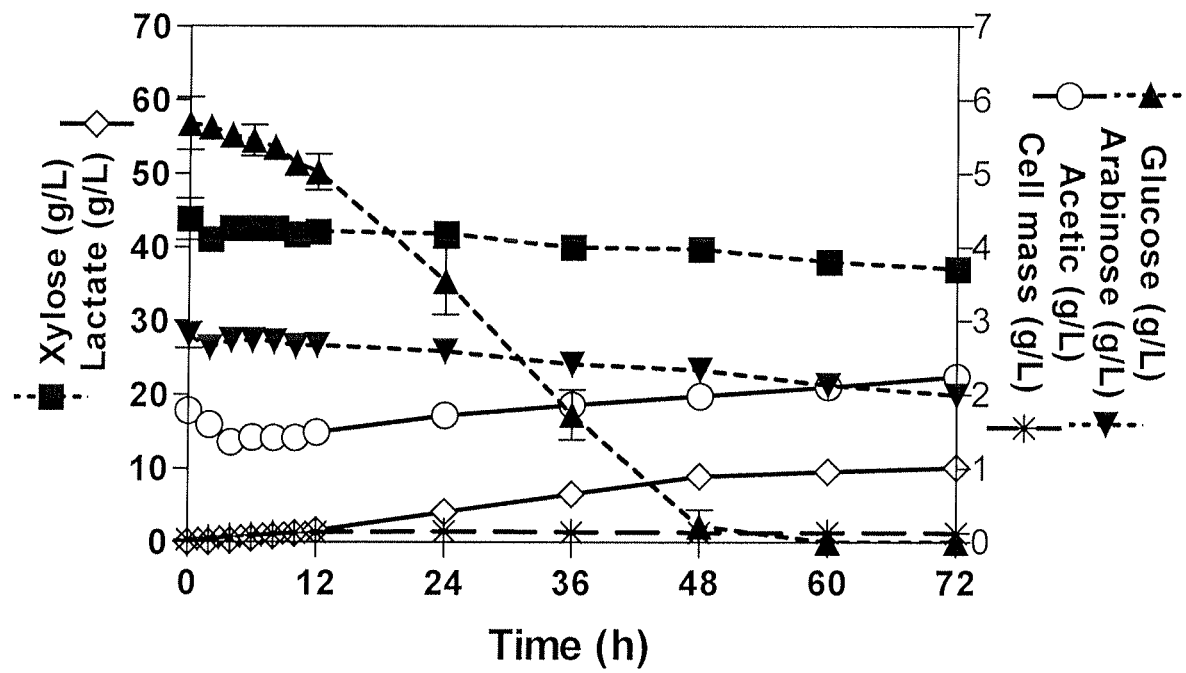
FIG. 18. Fermentation kinetics of strain JU15A on simulated hydrolysate 2.
Figure 19:
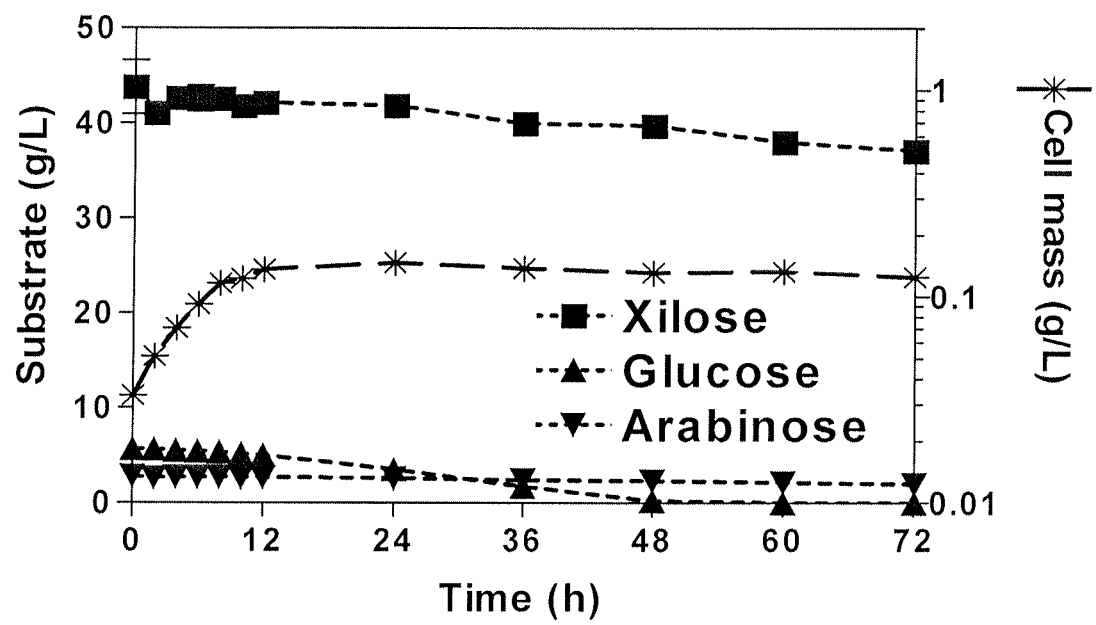
FIG. 19. Graphic that shows the growth and substrate consumption kinetics of strain JU15A on simulated hydrolysate 2

Afterward, the inventors of the present invention tested the new *E. coli* strain JU15A in a second control culture (simulated hydrolase 2) under the same pH, temperature and rpm conditions but changing the concentrations of the components present in the AM2 medium. In other words, the amount of $(NH_4)_2HPO_4$ and $NH_4H_2PO_4$ salts were reduced by one quarter without adding KCl, $MgSO_4 7H_2O$ or trace elements and maintaining the concentration of betaine and citric acid at a constant level, as well as those of the carbon sources (xylose, glucose and arabinose) and acetate. Table 8 and FIGS. 18 and 19 summarize the results obtained in this fermentation process.

TABLE 8

Kinetic parameters of the evaluation of *E. coli* JU15A in hydrolyzed simulated medium 2.

| *μ (h⁻¹) | *$q_S$ | *$q_P$ | *$Y_{X/S}$ | $Y_{P/S}$ | P | $X_{max}$ (g/L) | $X_{max}$ (CFU/mL) |
|---|---|---|---|---|---|---|---|
| 0.16 | 3.09 | 1.63 | 0.05 | 0.19 | 0.14 | 0.14 | $1.3 \times 10^{10}$ |

$Y_{P/S}$: $g_{lactate}/g_{sugar}$;
$Y_{X/S}$: $g_{cell\ mass}/g_{sugar}$;
$q_P$: $g_{lactate}/g_{cell\ mass} \cdot h$;
$q_S$: $g_{sugar}/g_{cell\ mass} \cdot h$; and
P: $g_{lactate}/L \cdot h$.
*Values obtained during exponential growth phase When comparing the control cultures with simulated hydrolysates 1 and 2, the inventors of the present invention clearly observed that the absence of potassium salts, magnesium and trace elements and lesser amounts of phosphate salts (nitrogen source) directly affected the growth of the new JU15A strain, even with specific growth rates (μ) being similar between the two cultures. The other kinetic parameters are drastically reduced, and the maximum cell mass reached in simulated hydrolysate 2 was 11 times less than that in simulated hydrolysate 1. Unexpectedly, and despite the amount of cell mass being lower in control culture 2, $q_S$ has a greater value (1.7 times in the exponential phase) for control culture 2. This result demonstrates, along with the value of μ, that at first, there is good growth that is rapid, but afterwards, the lack of essential nutrients results in an inability to maintain growth, which is why JU15A is limited in this type of culture.

Example 18

Characterization of *E. coli* JU15A in Cultures with Hydrolysates (A-F) in a System of Mini-Fermenters (Fleakers)

Figure 20:
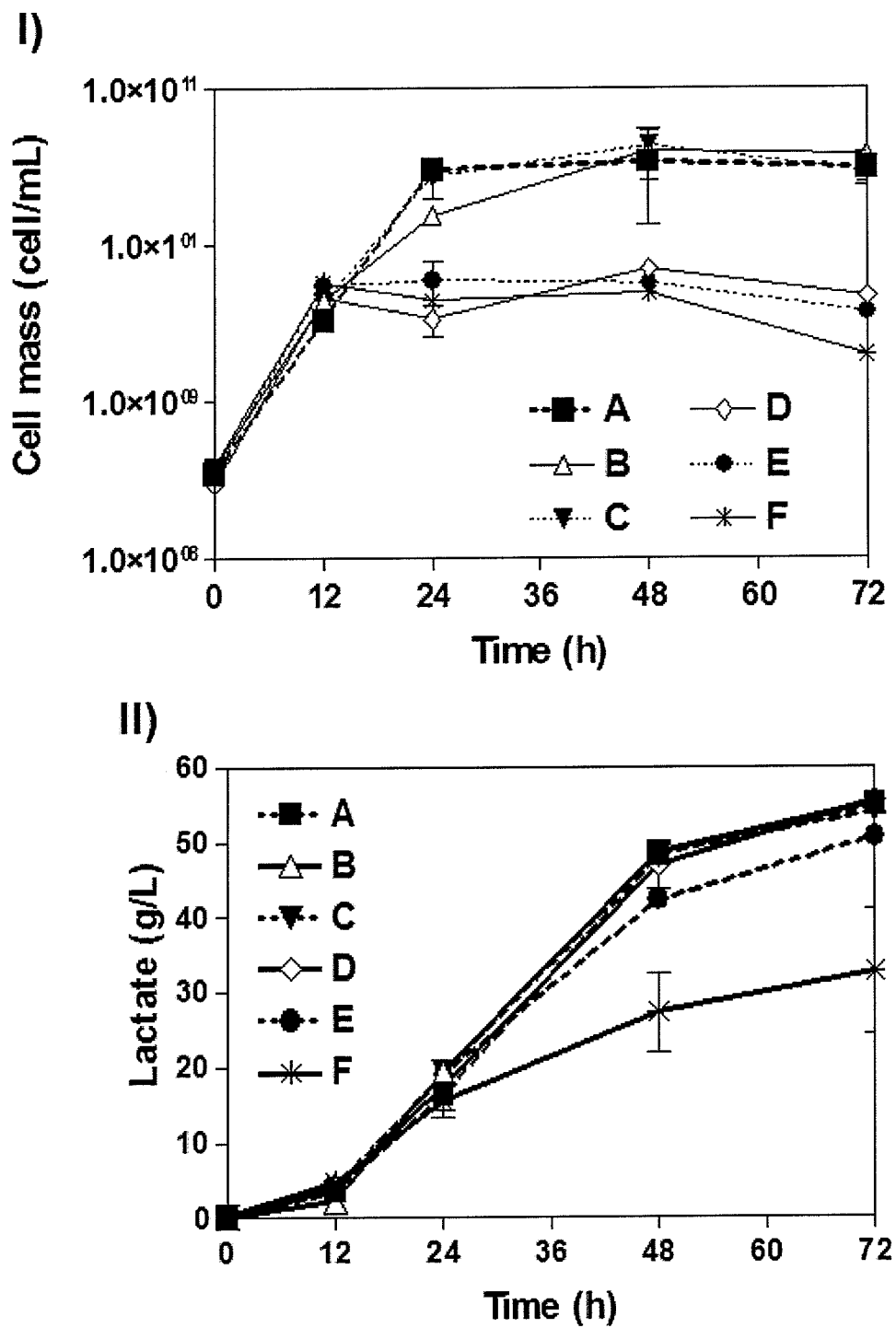
FIG. 20. Graphics that show: I) growth kinetics and II) lactate production kinetics on sugarcane bagasse hydrolysates of 6 independent experiments (A, B, C, D, E, F) using *E. coli* strain JU15A.
Figure 21:
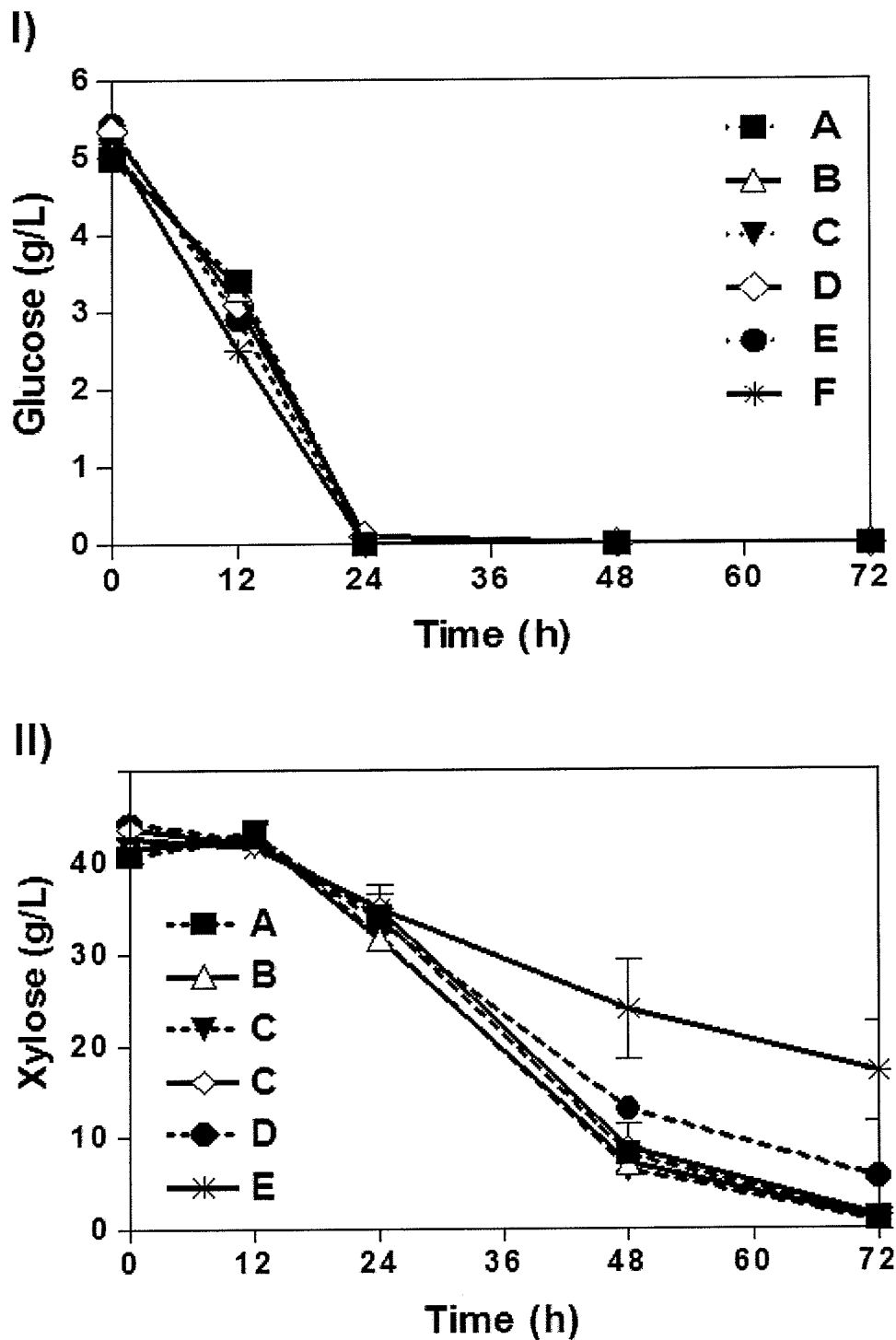
FIG. 21. Graphics that show kinetics of: I) glucose consumption and II) xylose consumption on sugarcane bagasse hydrolysates of 6 independent experiments (A, B, C, D, E, F) using *E. coli* strain JU15A.
Figure 22:
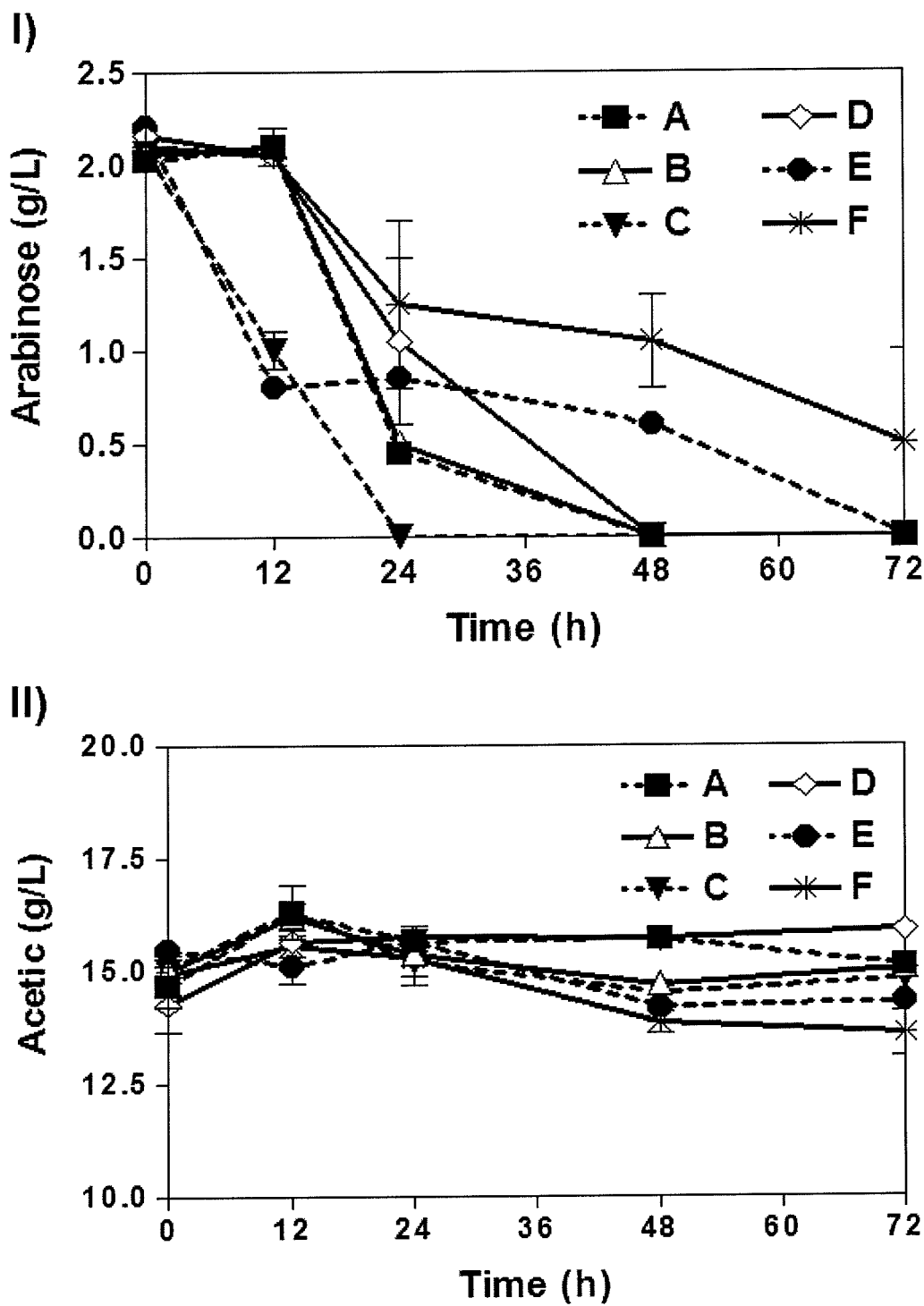
FIG. 22. Graphics that show kinetics of: I) arabinose consumption II) acetic acid accumulation on sugarcane bagasse hydrolysates of 6 independent experiments (A, B, C, D, E, F) using *E. coli* strain JU15A.

The inventors of the present invention also conducted experiments to test the effect of supplementing the culture medium with nutrients, both on productivity and on lactate yield. The inorganic salts of the AM2 medium were selected, and the concentrations were varied to supplement the hemicellulose hydrolysates of the vegetable tissues that were utilized, such as sugar cane bagasse, and to select the most appropriate culture medium to subsequently scale up the fermentation process to a 10-L operating volume. The results obtained when the hydrolysates contain both sugars (xylose, glucose and arabinose) and acetic acid are summarized in Table 5. The main results obtained from the fermentations with vegetable tissue hydrolysates, such as sugar cane bagasse, are shown in Table 9, and FIGS. 20, 21 and 22 show the behavior of JU15A in A-F cultures. Although the specific growth rate, volumetric productivity and product-substrate yield remained similar for cultures A-E, the cell mass achieved in the hydrolysates without supplements of magnesium, potassium and trace elements was 7.5 times less, which demonstrates a limitation caused by the fermentation medium that may affect various parameters, such as the cell mass-substrate yield and the specific rates of substrate consumption and product formation, which depend directly on the formation of cell mass.

TABLE 9

Kinetic parameters of the fermentation of different hemicellulosic hydrolysates from sugar cane bagasse.

| Kinetic parameter | JU15A | | | | | |
|---|---|---|---|---|---|---|
| | A | B | C | D | E | F |
| $X_{max}$ (CFU/mL) | $5.9 \times 10^{10}$ | $5.5 \times 10^{10}$ | $4.9 \times 10^{10}$ | $7.9 \times 10^{9}$ | $7.7 \times 10^{9}$ | $6.1 \times 10^{9}$ |
| *μ (h⁻¹) | 0.19 | 0.21 | 0.20 | 0.23 | 0.23 | 0.22 |
| $Y_{P/S}$ ($g_{lactate}/g_{substrate}$) | 1.14 | 1.14 | 1.11 | 1.09 | 0.98 | 0.66 |
| P ($g_{lactate}/L \cdot h$) | 0.77 | 0.77 | 0.75 | 0.77 | 0.70 | 0.45 |

*Values obtained during exponential growth phase. The nutrient addition is as detailed in table 5.

For the sugars, the glucose was totally consumed in all of the fermentations within 24 h. The arabinose was completely consumed for fermentations A-D in a period no greater than 48 h, but for fermentations E and F, in which the salt supplementation was very little or none, the arabinose was consumed in 72 h for the first case, and total consumption was not achieved in the second case. Similarly, the xylose was completely consumed in 72 h for four cases (A-D), with xylose remaining in the last two fermentations (E and F). However, in contrast to the results observed in the simulated hydrolysates, acetate was consumed in certain cases, indicating its participation as a carbon source under certain conditions and indicating that it does not act as an inhibiting compound for the growth of *E. coli* JU15A.

When the inventors of the present invention compared culture A with simulated hydrolysate 1, they observed similar results to those reported in the preceding tables for the documentation of the present invention with respect to the kinetic parameters, with a slight decrease in the amount of cell mass formed ($4.8 \times 10^{10}$ & $5.9 \times 10^{10}$ UFC/mL). However, when comparing culture D, which has a similar medium composition with simulated hydrolysate 2, a μ value that was 1.4 times larger was obtained, along with a product-substrate yield that was ~6 times larger and a volumetric productivity that was 5 times larger. These results indicate that the components found in the hydrolysates benefit the metabolism of JU15A.

Unexpectedly, the specific growth rates obtained for cultures A-F were greater than those previously reported. In the present invention, when JU15A strain was tested in mineral media at different conditions for glucose/xylose and despite the total sugars in the fermentations not being completely consumed, the yield surprisingly surpassed the theoretical maximum reported in the majority of cases. This observation leads to the conclusion that hydrolysates have other carbon sources that are converted to D-lactate and that were not considered in the control cultures. In addition, the present characterization surprisingly showed that the addition of supplemental compounds, such as KCl, $MgSO_4 7H_2O$ or trace elements, is not necessary, as the new strain, JU15A, has the capability of growing with only the addition of a nitrogen source—$(NH_4)_2HPO_4$ and $NH_4H_2PO_4$ salts) and of producing a large amount of D-lactate rapidly, showing that the hemicellulose hydrolysates of vegetable tissue, such as sugar cane bagasse, provide an adequate fermentation medium. To illustrate the invention utilized in a 10-L fermentation, the medium composition of culture D was selected because it gave good yields and productivity, despite not forming the maximum amount of cell mass obtained in other fermentations reported for the present invention.

Example 9

Characterization of *E. coli* JU15A in Culture Medium D in a 10-L Fermenter

The inventors conducted the characterization of the new strain of *E. coli*, JU15A, in the hemicellulose hydrolysates of vegetable tissue, such as sugar cane bagasse, with added betaine, citric acid and phosphate salts in a 10-L pilot fermenter. The operating parameters, such as the temperature and pH, were the same as those used in the mini-fermenters, and the shaking rate was empirically determined to achieve homogeneous mixing of the hydrolysate in the bioreactor (240 rpm). The data obtained during the fermentation process are shown in Table 10 and FIG. 23. These results showed that there was rapid growth, reflected in a $\mu$ value of 0.28 h$^{-1}$. However, there was a yield greater than the theoretical maximum, $Y_{P/S}$ de 1.3 $g_{lactate}/g_{sugar}$, because of other compounds, aside from sugars, that are present in the hydrolysates and that serve as a source of carbon. Although the xylose was not completely consumed, the final volumetric productivity attained was 0.50 $g_{lactate}$/L·h, which is lower in comparison to fermentations carried out in mini-fermenters (Fleakers) under similar conditions.

TABLE 10

Kinetic parameters of *E. coli* JU15A strain in a 10 L fermentation.

| *$\mu$ (h$^{-1}$) | $Y_{P/S}$ $g_{lactate}/g_{sugar}$ | P $g_{lactate}$/ L·h | $X_{max}$ (CFU/mL) |
|---|---|---|---|
| 0.28 | 1.30 | 0.50 | 6.0 × 10$^9$ |

*Exponential growth phase

Figure 23:
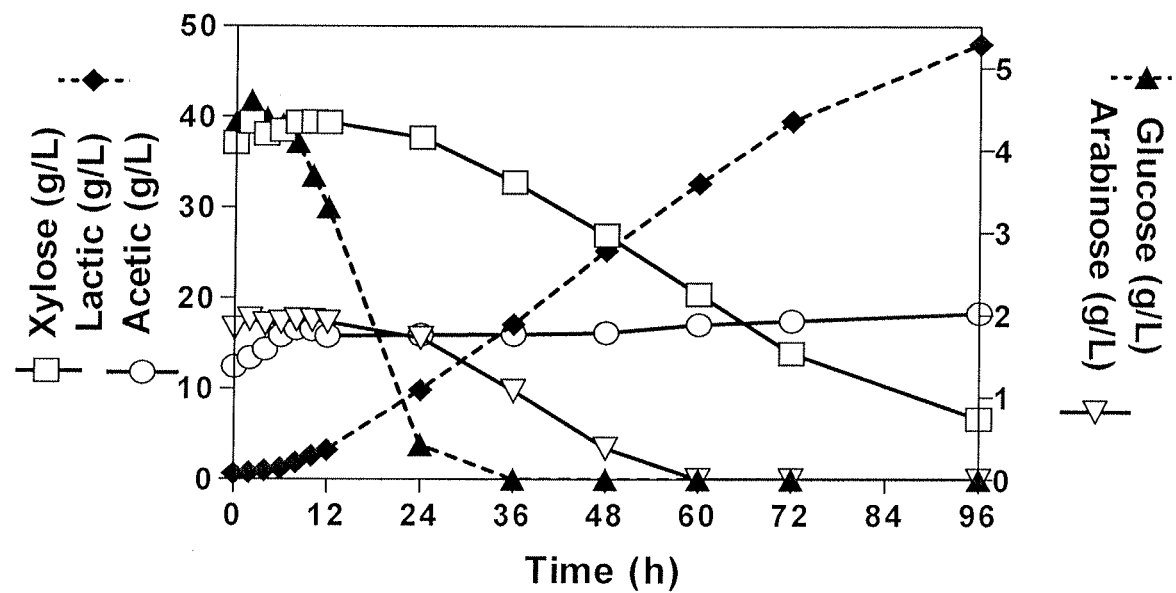
FIG. 23. Fermentation kinetics of strain JU15A on sugarcane bagasse hydrolysates.

The hydrolysate that was used in this experiment was stored for several months at 4° C., and it had a concentration of 15.9 g/L of acetic acid at the start of the 10-L culture. FIG. 23 shows that the acetate was not consumed and actually had a slight increase in its concentration (+6 g/L), once again showing the remarkable ability of the new strain of *E. coli*, JU15A, to maintain its growth in concentrations of up to 15.9 g/L of acetic acid (265 mM) or of up to 36 g/L of sodium acetate. The amount of cell mass formed did not reach the maximum values attained by the cultures cultivated in the mini-fermenters. This result could be due to the high concentration of acetate in the medium, which, although not completely inhibiting, can have a slight impact on the growth of the strain.

Example 10

Lactose Fermentation

Figure 24:
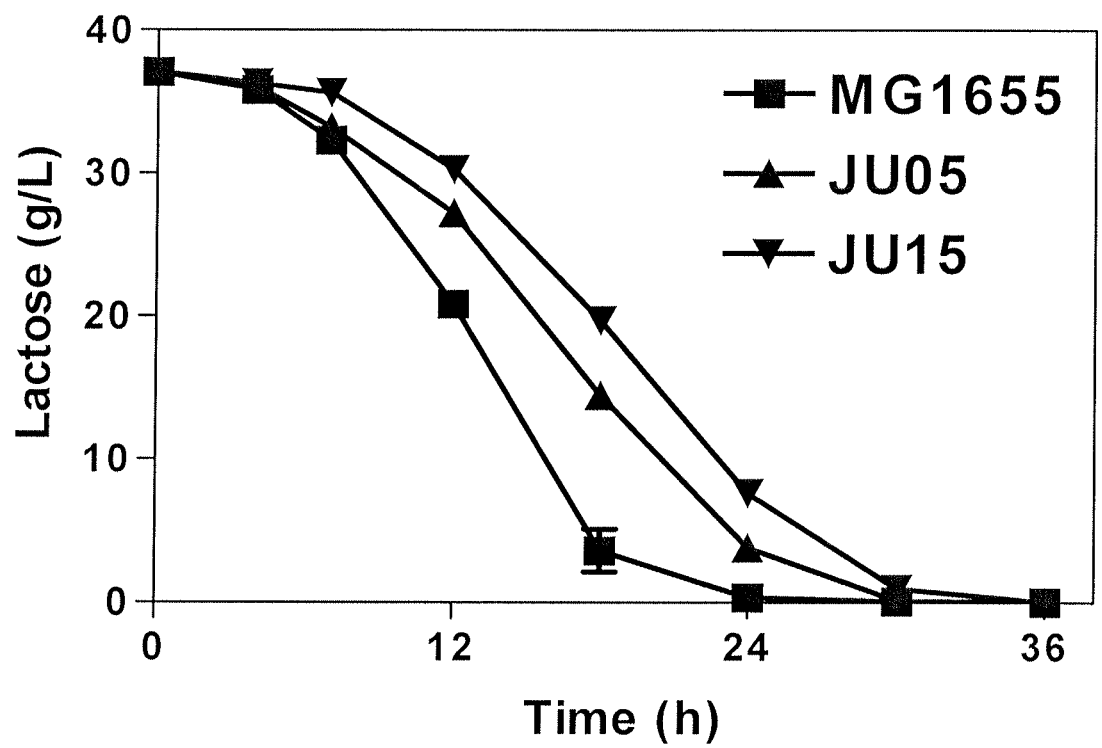
FIG. 24. Lactose consumption kinetics of three different strains: MG1655, JU01 and JU15
Figure 25:
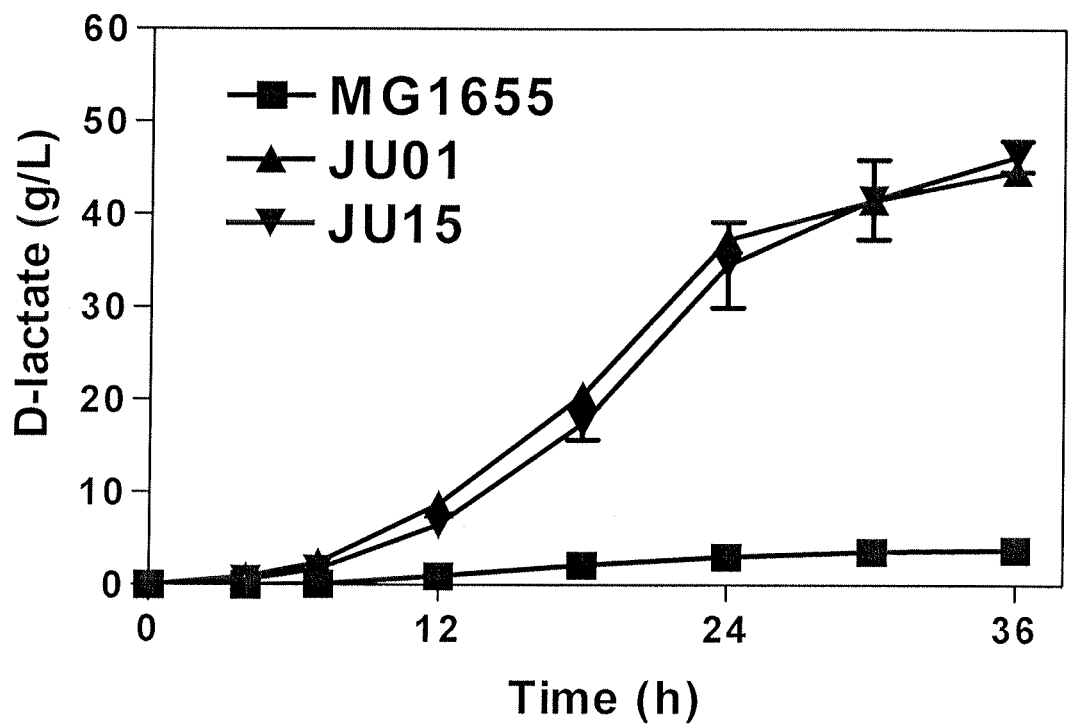
FIG. 25. Graphic that shows D-lactate production kinetics from lactose of three different strains: MG1655, JU01 and JU15.

For the present invention, the capacity of the JU15 strain to use lactose as a carbon source in AM2 mineral medium with 4% lactose to produce lactate was tested, and the following results were obtained: a) strain JU15 consumes lactose at the same rate as its parent JU01 (see FIG. 24) and b) this strain is capable of converting lactose into D-lactate with yields higher than 95% and productivities of approximately 1 g/L·h. The data obtained from the fermentation process in the present work are shown in FIGS. 24 and 25.

Example 11

Fermentation of Whey

For the present invention, it was considered to be important to evaluate the capability of the JU15 strain to ferment other low-cost raw material sources, such as whey (Nutting, 1970). Taking into account the chemical composition of whey, only betaine was added (at a 1 mM concentration) as an osmoprotector for the whey. In addition, the present invention tested the fermentation of whey supplemented either with 50 g/L of lactose or of xylose. It was not possible in these fermentations to quantify the growth of the strain via optical density, due to the initial turbidity of the whey. Therefore, the fermentation of whey was determined by the consumption of the base used to neutralize the lactic acid produced.

Figure 26:
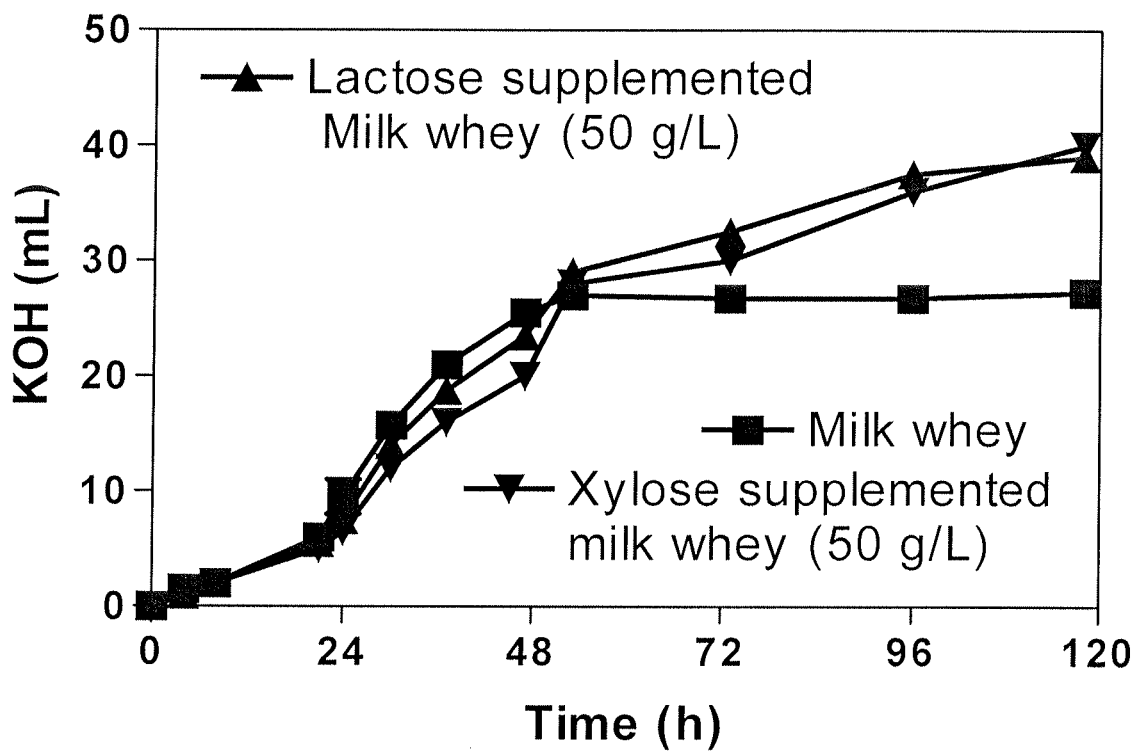
FIG. 26. Graphic that shows base consumption kinetics in three different media with milk whey using JU15 strain.

The results obtained in this part of the present invention showed two relevant findings: a) strain JU15 can grow in and ferment the sugars present in whey and b) the productivity of the process was lower than that obtained using AM2 mineral medium, which was most likely due to whey being limited in minerals required for the growth of JU15 (FIG. 26).

Example 12

Integration of L-Lactate Dehydrogenase from *Bacillus subtilis* for the Production of L-Lactate Construction of the pLDH$_{Bs}$C Plasmid During the development of the present invention, this plasmid was constructed with the goal of using it as a template for the PCR to be used in chromosome integration. Starting from the pTrclctE plasmid (Vázquez-Limón et al., 2007), the inventors constructed the plasmid pLDH$_{Bs}$C by cloning the PCR fragment containing the gene that confers resistance to chloramphenicol (Cm$^r$) flanked by FRT sites that facilitated the recombination in the chromosome. This fragment was obtained from the pKD3 plasmid (Datsenko and Wanner 2000). The Cm$^r$ gene in the pLDH$_{Bs}$C plasmid was downstream of the lactate dehydrogenase gene of *B. subtilis* (ldh$_{Bs}$) (see FIG. 27).

Example 13

Insertion of the *B. subtilis* ldh Gene in the Chromosome of JU15

The inventors of the present invention had to design a pair of primers with homologous regions at the start and finish of the ldh gene of *E. coli* in order to insert the ldh$_{Bs}$ gene in the JU15 strain. The insertion of the ldh$_{Bs}$ gene into the chromosome of JU15 was accomplished through the modification of the strategy provided by Datsenko and Wanner 2000. Initially, the inventors designed a pair of primers to amplify a DNA fragment that contains the ldh$_{Bs}$ gene and the chloramphenicol resistance cassette flanked by FRT sites using the pLDH$_{Bs}$C plasmid.

The specific primers EcLDHBsIntFw (SEQ. ID NO: 13) and EcLDHBsIntRv (SEQ. ID NO: 14) have homology with the regions adjacent to the gene that is to be suppressed (H1 and H2) and with the plasmid (pKD3) template (P1 and P2) that contains the gene for resistance to chloramphenicol flanked by FRT sites.

Figure 28:
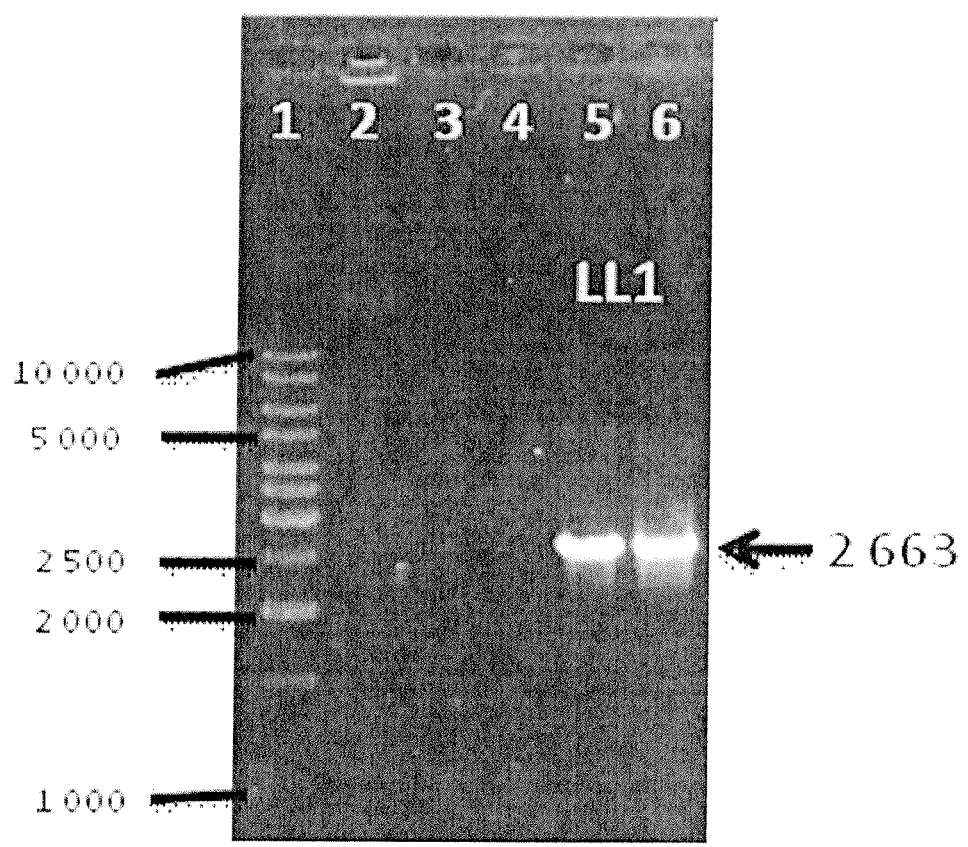
FIG. 28. Image that shows an agarose gel with a PCR product corresponding to the integration of the heterologous gene. Lane 1: Molecular weight marker (size in base pairs); Lanes 2 and 3: 2.6 kbp PCR products corresponding to the verification of the gen in the LL1 strain.

FIG. 28 depicts a gel used in the analysis of the colonies as previously described. Lane 1 shows the molecular weight marker, and lanes 5 and 6 correspond to strain LL1 (JU15 ΔldhA::ldh$_{Bs}$Cm). A PCR product was amplified that coincided with the expected molecular weight (2,663 bp) when the heterologous gene was inserted.

The inventors obtained strains resistant to Cm and, using PCR, confirmed a fragment that corresponded to the size of the ldh$_{Bs}$ gene and the Cm resistance cassette, which is why the inventors assumed a successful insertion of the heterologous Idh$_{Bs}$ gene and the Cm resistance cassette. The PCR indicated that the Idh$_{Bs}$ gene is under the control of the native promoter of *E. coli*.

The inventors transformed the LL1 strain with the pCP20 plasmid, which contains FLP recombinase, which, in turn, recognizes FRT sites. The FRT sites flank the gene responsible for conferring resistance to chloramphenicol. The inventors carried out a simple recombination in which the cat gene was excised, leaving only a single FRT site in the chromosome.

In the present invention, Primer 1189 Fwd (SEQ. ID NO: 15) and Primer 1190 Rvs (SEQ. ID NO: 16) were designed to verify this suppression, and these primers showed regions of homology 200 by before and after *E. coli* IdhA.

Figure 29:
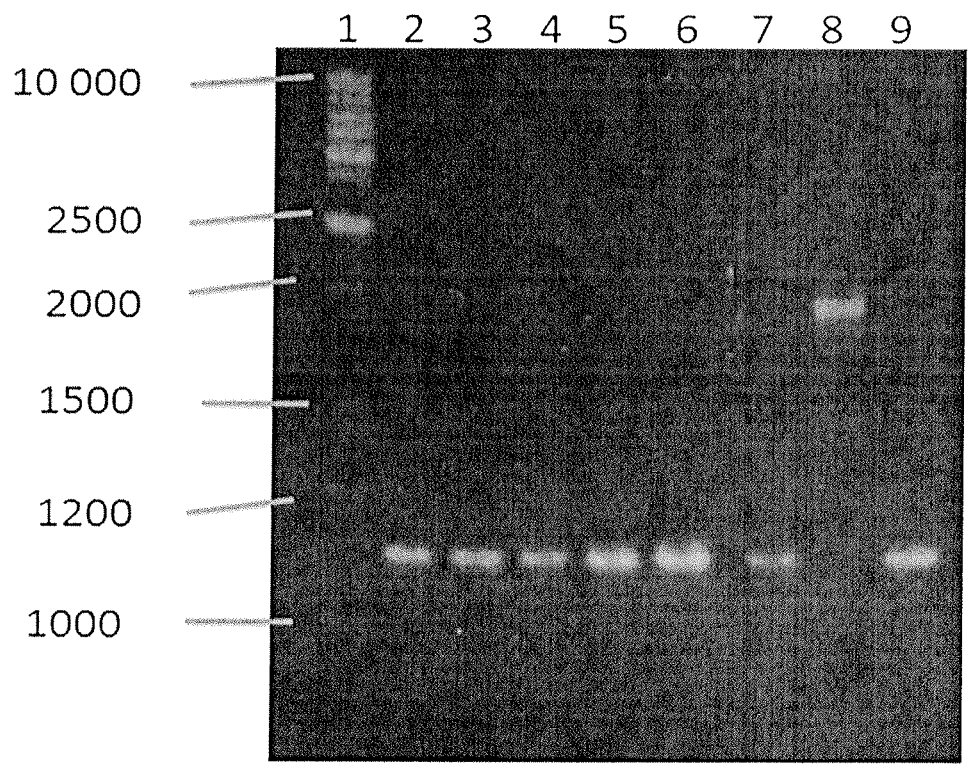
FIG. 29. Image that shows an agarose gel with the verification of the heterologous gene integration and the elimination of the chloramphenicol acetyl transferase gene. The PCR products of the colonies with the inactivated ldhA gene and without the Cm resistance gene are showed in the 2-6 lanes, as well as the control strain JU15 in the 7 and 9 lanes which product is 1069 by size. The 8 lane is the negative control of 1860 by size.

The inventors obtained a product close to 1,093 bp, which corresponded to the sites adjacent to the gene and the FRT recognition sequences of FLP recombinase. Thus, they obtained the strain labeled in the present invention as LL2 (*E. coli* MG1655, ΔpflB, ΔadhE, ΔfrdA, ΔxylFGH, IdhBs, km$^r$) (LL2 lakes Cm$^r$) (see FIG. 40). The PCR products of the colonies with a suppressed IdhA gene and that lack the gene that confers resistance to Cm are shown in FIG. 29, lanes 2 to 6; the control JU15 strain is in lanes 7 and 9 with a 1,069-bp product, and lane 8 corresponds to a negative control of 1-860 bp.

From strain LL2, the inventors obtained five colonies that were then phenotypically characterized. These colonies were denominated as LL2, with the addition of a parenthesized range number (1-5). The following parameters were tested: growth, glucose consumption and consumption of the 2 N KOH base, using minimal AM2 media in anaerobic conditions at a temperature of 37° C. and stirring at 150 rpm.

The inventors observed that the strains labeled as LL2(2) and LL2(3) showed lag phases of 12 and 24 h, respectively, (data not shown) which is why they decided to subject these two strains to the process of adaptive evolution.

Example 14

The Adaptive Evolution of the LL2 Strain in 40 g/L Xylose

The adaptive evolution consisted of performing culture transferences when the culture was in the exponential phase from one mini-fermenter to another along with 40 g/L of the carbon source (xylose), which was inoculated to an optical density of 0.01 (0.0037 g$_{DCW}$/L).

The inventors required six passes to obtain a constant behavior, that is, a state from which the capacity to grow in xylose did not improve. The strain that was finally obtained was labeled as LL26, and it exhibited a correlation of optical density and base consumption that represented the highest level and the fastest time, respectively. Previously, this invention described how adaptive evolution was performed on JU15, which ferments xylose yielding 95% conversion to D-lactate; the results are mentioned above.

Figure 30:
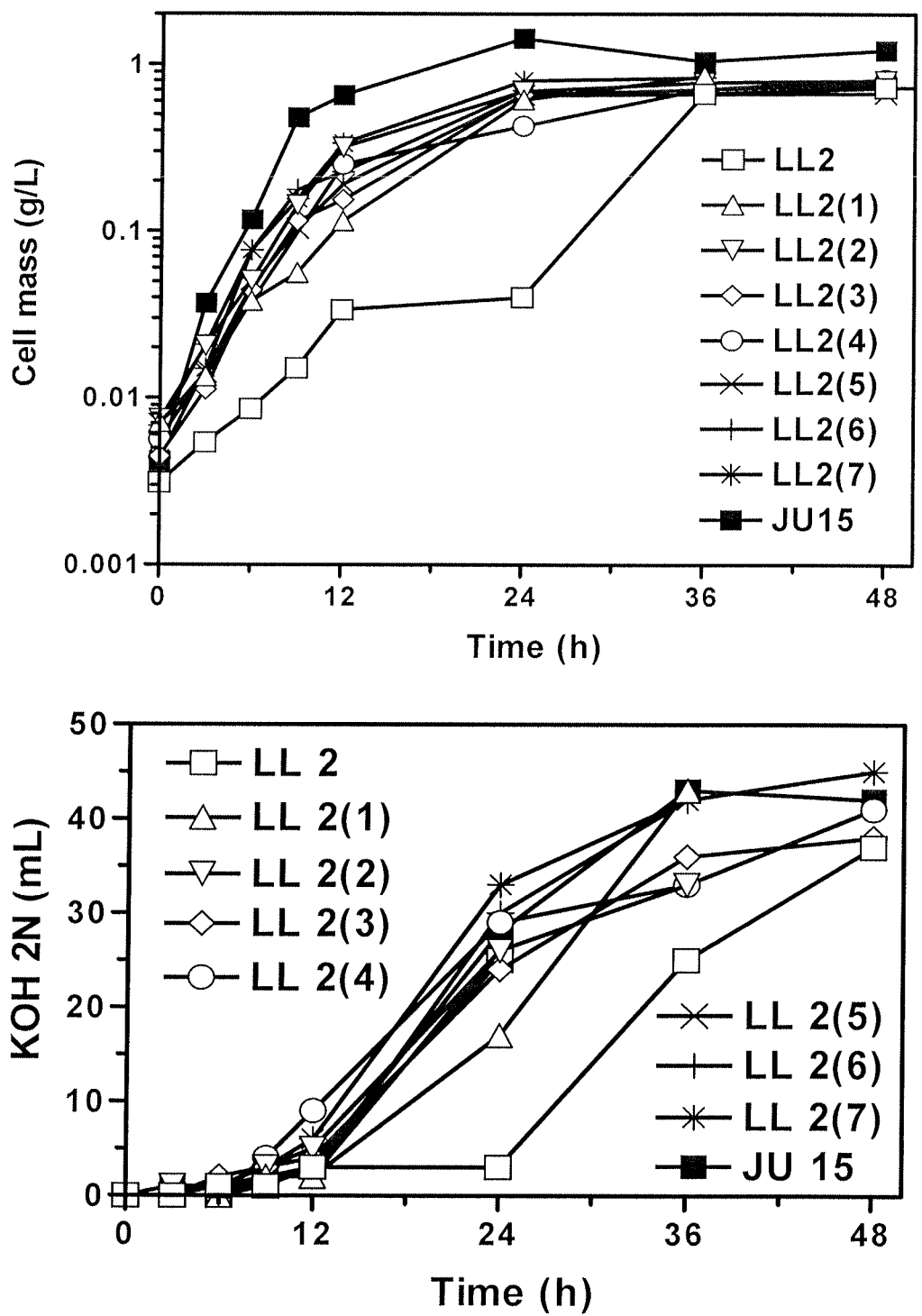
FIG. 30. Illustrates the adaptive evolution and the KOH 2N consumption of the strains LL2 vs strain JU15 in xylose 40 g/L.

FIG. 30 compares the transferences of LL2(1) to LL2(7) in 40 g/L xylose fermentation conditions. The 7$^{th}$ pass is a replica of the behavior of LL2(6); there is no improvement from pass 7 to pass 9 (data not shown), which is why pass 6 was selected as the evolved strain. As a control, the JU15 strain was used, and the behavior of the LL26 transferences is very similar. The inventors observed that the maximum consumption of 2 N KOH occurs in the interval from 12 h to 24 h for all of the strains. The consumption of the base is used to determine the growth of the strain and the consumption of xylose, given that it is a homofermentative strain, whose capacity for regenerating its reducing power is restricted to the production of L-lactate from xylose.

Figure 38:
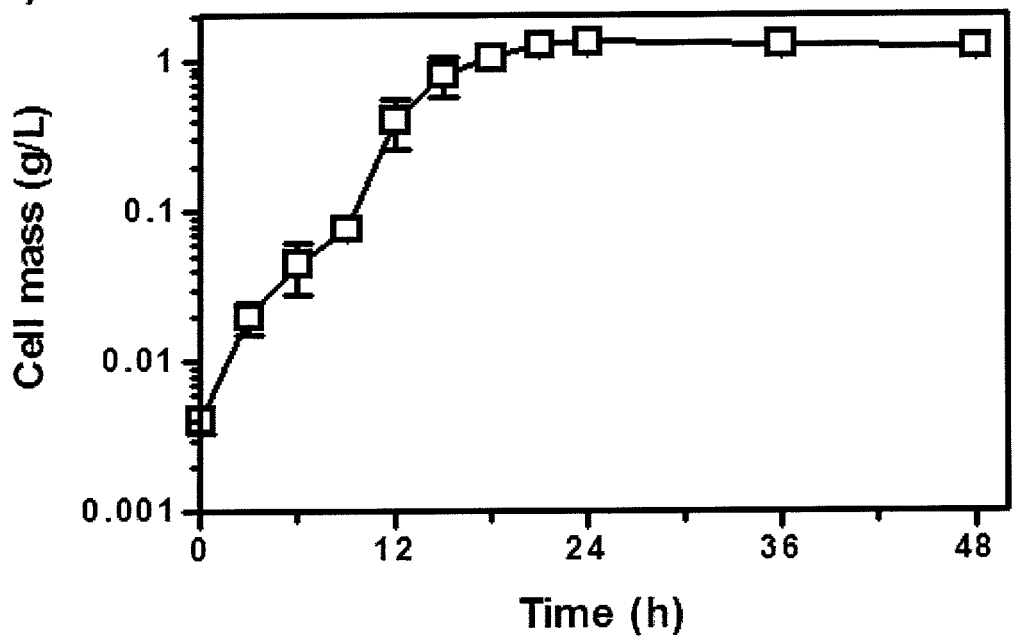
FIG. 38. Graphic that shows: I) the fermentation kinetics of the strain *E. coli* LL26 in AM2 medium with glucose (4%). II) Glucose consumption and lactate production. The yield was close to the theoretical (100%) and the volumetric productivity 1.17 g of lactate per liter per hour.
Figure 38:
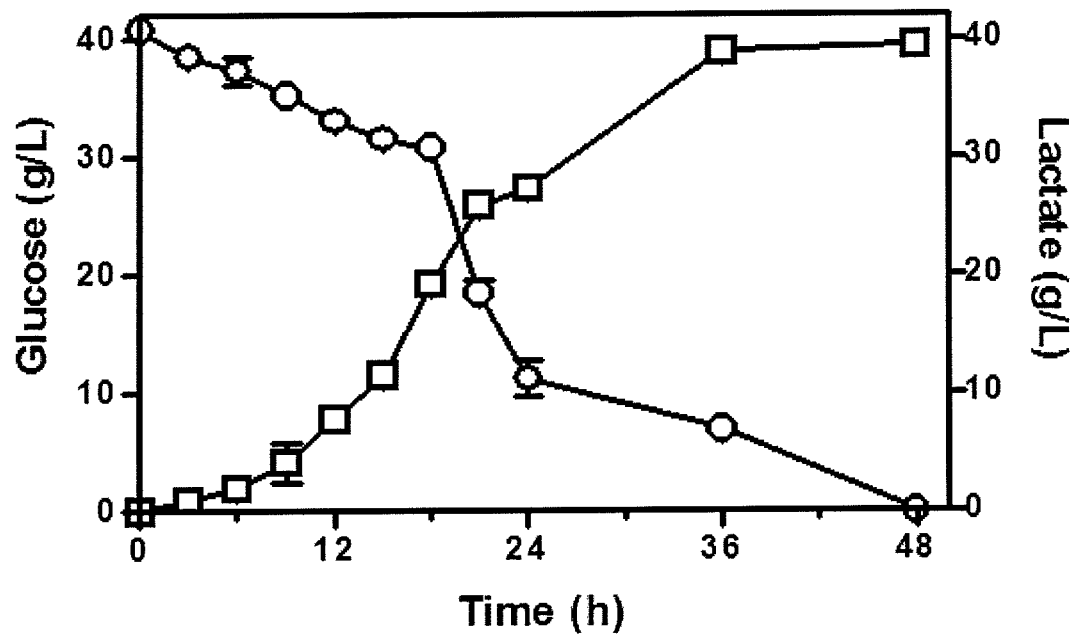
Figure 39:
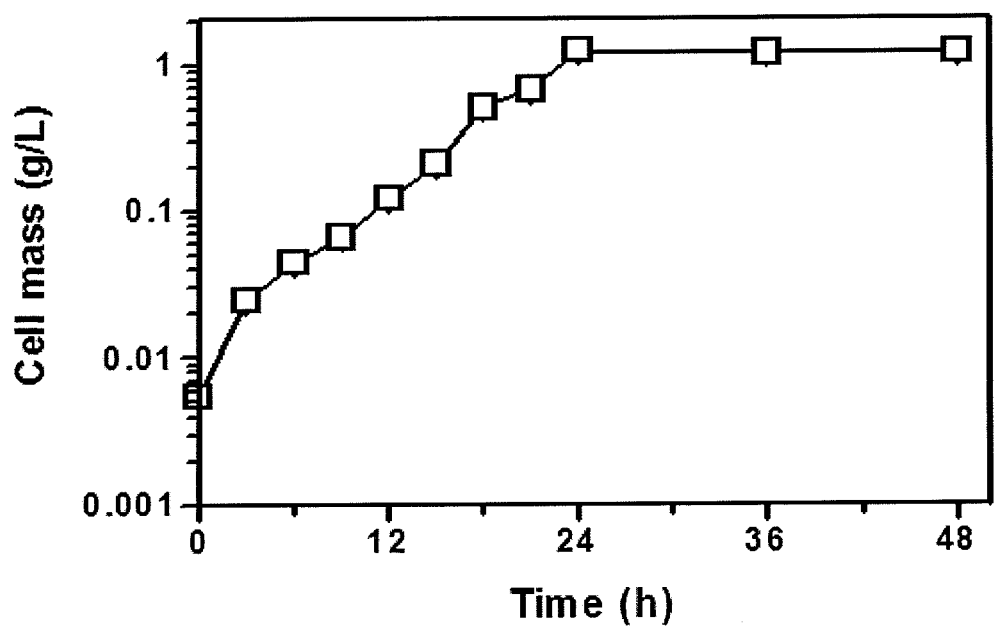
FIG. 39. Graphic that shows: I) the fermentation kinetics of the strain *E. coli* LL26 in AM2 medium with xylose (4%). II) Xylose consumption and lactate production. The yield was close to the theoretical (100%) and the volumetric productivity 0.68 g of lactate per liter per hour.
Figure 39:
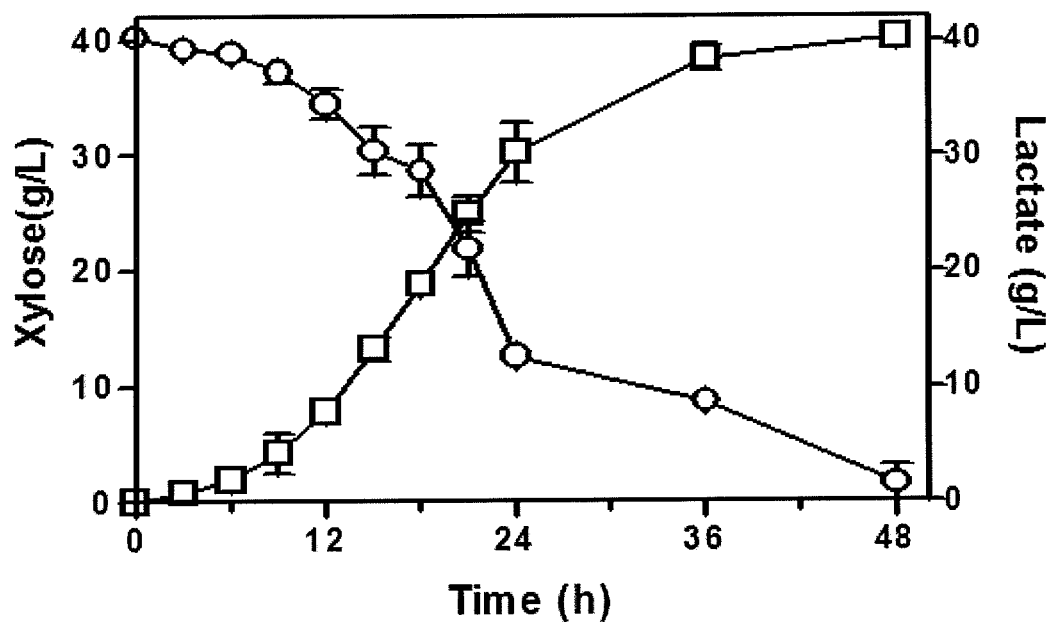

From cultures in glucose, it was observed that strain LL26 converts any carbon source to L-lactate with a yield near the theoretical value (>95%) and with a volumetric productivity of 1.17 g/L*h. For xylose, 95% conversion was observed, but the volumetric productivity was reduced to 0.68 g/L·h (see FIGS. 38 and 39).

Example 15

The Construction of an Ethanol-Generating Strain from Strain JU15A

Suppression of the IdhA Gene that Codes for the Lactate Dehydrogenase Enzyme

For the suppression of the IdhA gene in the *E. coli* strain JU15A, the inventors used the method described by Datsenko and Wanner (2000), which uses the λ phage Red recombination system to inactivate genes in the chromosome of *E. coli* with homologous recombination using linear PCR products.

The protocol for the suppression of the IdhA gene of *E. coli* strain JU15A (*E. coli* MG1655 ΔpflB, ΔadhE, Δfrd, ΔxilFGH::Km$^R$, resistant to acetic acid) using this method is described below.

Figure 31:
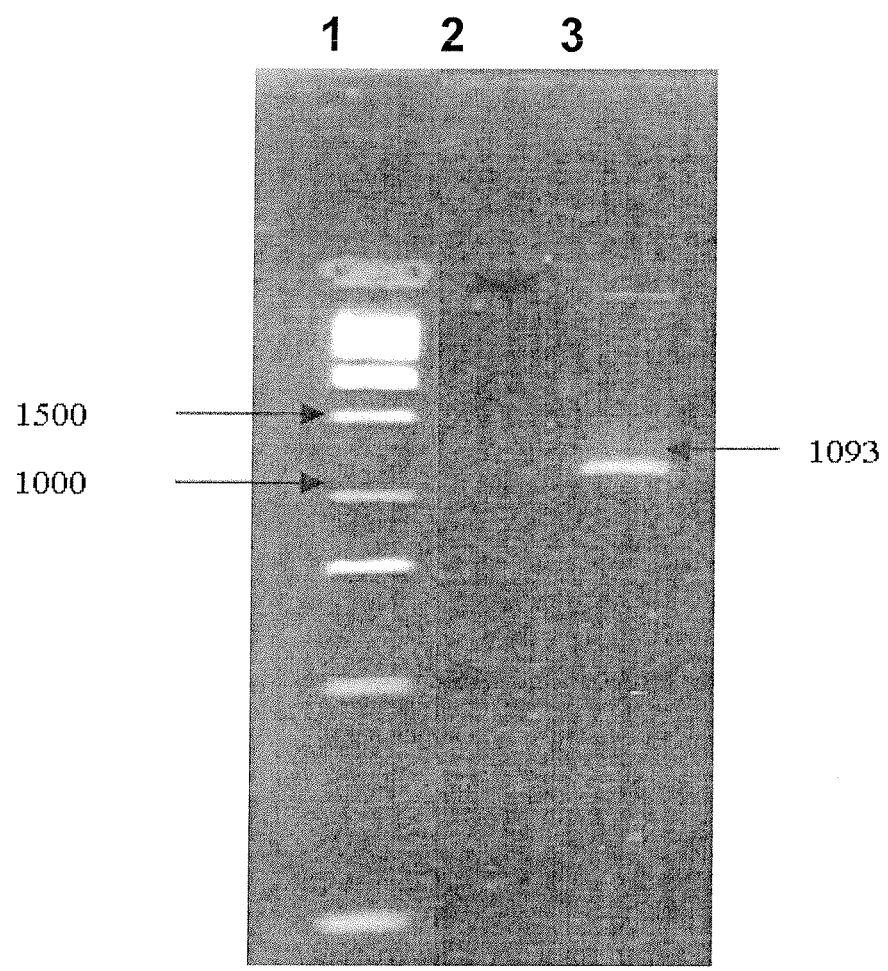
FIG. 31. Image that shows a 1% agarose gel with the PCR product of the chloramphenicol acetyl transferase gene (Cm), flanked by the FRT, PS1 and PS2 sites; and the JU15A IdhA gene homology sequences. Lane 1: molecular weight marker (size in bp), lane 3: PCR product.

When the inventors used the primers 716FWF (SEQ. ID NO: 17) and 717RVF (SEQ. ID NO: 18), they obtained a PCR product that consisted of the gene for resistance to chloramphenicol (cat) flanked by sequences homologous to the *E. coli* gene IdhA (see FIG. 31).

The PCR product was transformed by electroporation at 2,500 V into *E. coli* strain JU15A (pKD46). Next, 100 µL of the cells was seeded in LB and Cm 30 (µg/mL) medium to recover recombinant strains in which the IdhA gene was replaced by the Cm gene and flanked by the PS1 and PS2 sites. Thus, the strains recovered with resistance to Cm 30 were later analyzed by PCR to verify the suppression of the IdhA gene.

Figure 32:
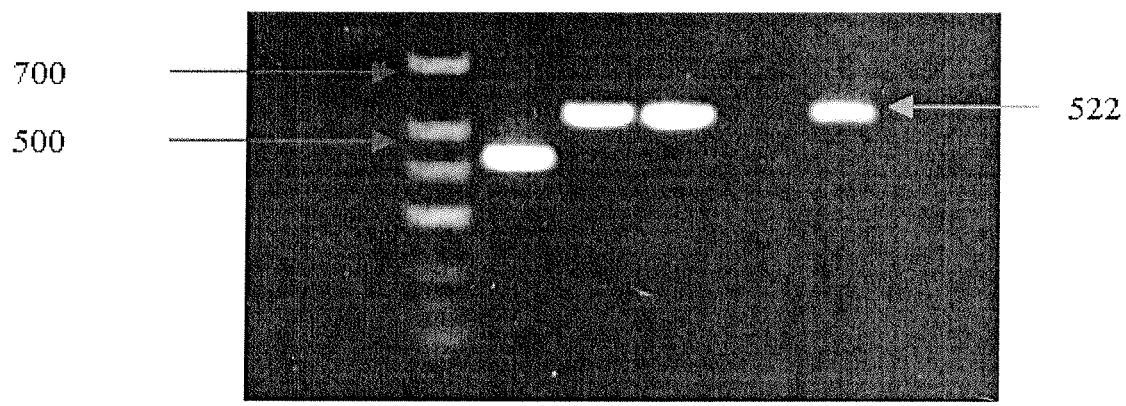
FIG. 32. Image that shows a 1% agarose gel with the verification of the IdhA gene inactivation by PCR. Lane 1: molecular weight marker (size in bp), lane 3: control $Cm^R$, Lanes 4-7: PCR product of 4 colonies transformed with an oligonucleotide with homology to the Cm gene region and the oligonucleootide 1190 RVF.

To phenotypically confirm that this recombination had taken place, several of the colonies obtained in the previous step and the control strain (JU15A, IdhA$^+$) were seeded in replicates in minimal M9 media with 20 g/L glucose and 30 mg/L Cm in aerobic conditions and in anaerobic systems at 37° C./24 h. The colonies were seeded in minimal medium and in anaerobic conditions to verify the suppression of the IdhA gene, as this was the only way that *E. coli* strain JU15A could regenerate reducing power (NAD$^+$) and survive metabolizing pure glucose in anaerobic conditions. Thus, the colonies that did not grow after 24 h in anaerobic conditions (IdhA$^-$) but that did grow in aerobic conditions were chosen for PCR analysis. To perform the PCRs for these strains and the control strain (JU15A), the primers 1189 FWF (SEQ ID NO: 19) and 1190 RVF (SEQ ID NO: 20) were designed, with approximately 20 bp homologous to regions located 200 bp before and after the IdhA gene. The PCR analysis was performed with these primers and the chromosomal DNA of the strains that did not grow in anaerobic conditions and were resistant to chloramphenicol. However, because of the size of the Cm gene insert and because the FRT and PS sites were very similar to the IdhA gene, the PCR products of strain IdhA$^-$ and of the control strain (JU15A, IdhA$^+$) only differed by 66 bp and could not be differentiated in agarose gels (data not shown). Through this analysis, a new primer was obtained that was homologous to an intermediate region of the Cm gene and, together with primer 1190 RVF (SEQ ID NO: 20), PCRs were once more performed on the chromosomal DNA of four colonies. Three of the colonies amplified a product of 522 bp, corresponding to the expected size using the Cm primer (FIG. 32), which insured that these three colonies had the Cm gene inserted in place of the IdhA gene.

Suppression of the Cm Resistance Cassette

Figure 33:
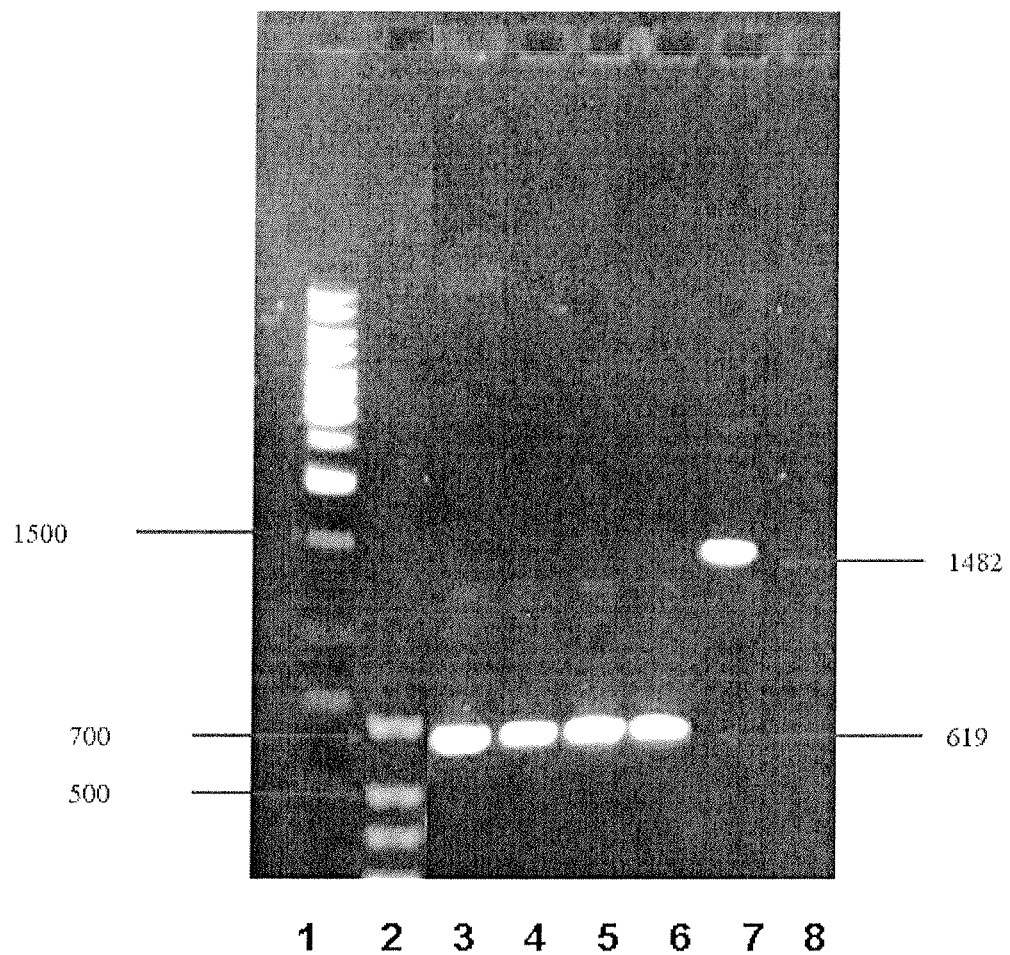
FIG. 33. Image that shows a 1% agarose gel: Lane 1-2 molecular weight marker (size in bp); Lane 3-6 PCR product showing the inactivation of the IdhA gene and the elimination of the Cm gene from 4 colonies transformed with the pCP20 plasmid, product size: 619 bp; Lane 7: control strain JU15A IdhA$^+$ (1482 bp).

The PCR products of four colonies with the suppressed IdhA gene and without the chloramphenicol resistance gene in addition to the control strain JU15A (IdhA$^+$) are shown in FIG. 33.

After isolating and identifying the colonies with suppressed IdhA and without resistance to chloramphenicol, they were seeded in LB media and stored in 40% glycerol at −70° C. This new strain was labeled E. coli MS01 with the genotype (ΔpflB, ΔadhE, Δfrd, ΔxilFGH::Km$^R$, ΔIdhA); it is incapable of growing in anaerobic conditions in mineral media and with glucose as the only carbon source.

Insertion of the pdc and adhB Z. mobilis Genes in E. coli MS01 under the Promoter Control of pflB.

The inserted pdc and adhB Z. mobilis genes were intended to be under the control of the promoter of pflB, which is strongly expressed in anaerobic conditions in E. coli, thus yielding a good level of the transcripts for these genes for the production of ethanol in anaerobiosis.

Strain MS01 (ΔpflB, ΔadhE, Δfrd, ΔxilFGH::Km$^R$, ΔIdhA, acetate resistant) has the pflB gene suppressed, so primers were designed with homology for several by before and after the pflB gene to amplify and sequence this region of the pflB gene and determine whether the sequences of its promoters were intact. The primers used to generate the PCR of this region were the primers 4166 (SEQ ID NO: 21) and 4167 (SEQ ID NO: 22).

Once the PCR product of the region before/after the gene pflB had been obtained (569 bp), it was sent for sequencing, and the sequencing results show that the method used to suppress pflB did not affect the promoter region of this gene and that 30 bp from the start codon (ATG) to the stop codon (TAA) remained as shown in the sequence below.

Sequencing of the pflB Gene Region:

```
                                        (SEQ ID NO: 25)
5'-tac gca gta aat aaa aaa tcc act taa gaa ggt agg tgt tac ATG TCC GAG CAA GCT TCT CAA TCT ATG TAA tta gat ttg act gaa atc gta cag taa aaa gcg tac aat-3'.
```

In the prior sequence (SEQ ID NO:25), the codons in capital letters represent the 30 bp of the pflB gene with a suppression sequence for Hind III, whereas the codons in lowercase letters show the regions approximately 40 bp before the start codon (ATG) and after the stop codon (TAA) of the pflB gene, which do not affect the promoter region of this gene (Sawers and Bock, 1989).

Figure 34:
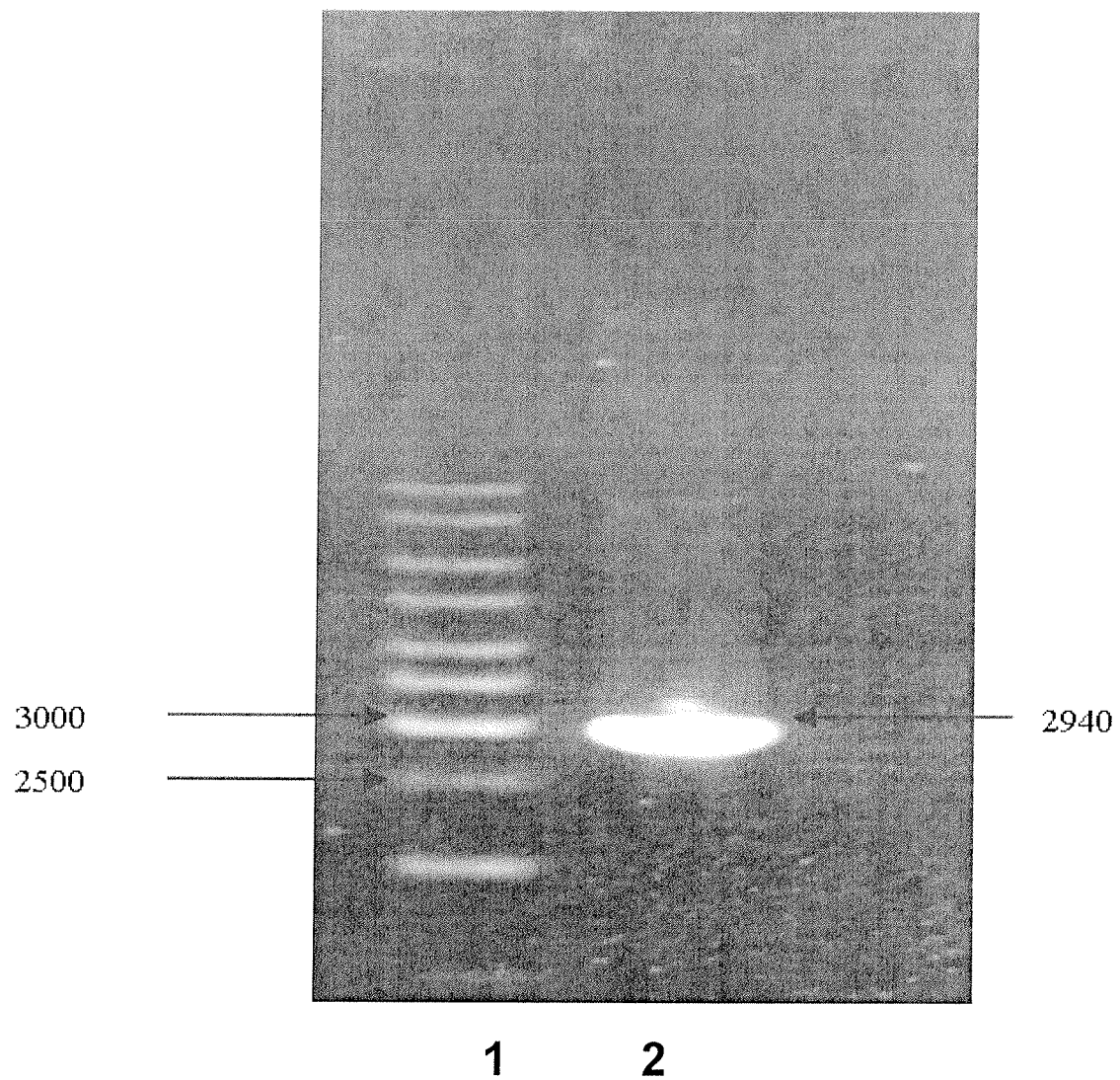
FIG. 34. Image that shows an agarose gel with a PCR product that carries the pdc and adhB genes from *Z. mobilis* flanked by homology sequences up and downstream from pflB gen of *E. coli* strain MS01. Lane 1: molecular weight marker (size in bp), lane 2: PCR product.

Using the data from the prior sequence, the inventors sought to insert the Z. mobilis pdc and adhB genes under the control of the promoter sequence for the E. coli MS01 gene pflB through double homologous recombination, exchanging those two genes with the leftover region of the pflB gene (the capital letter codons of the pflB sequence). To this end, the A phage Red recombination system was used again, with the methodology previously described, to modify strain MS01. According to this system, cells of E. coli strain MS01 were made chemocompetent, transformed with the pKD46 plasmid, isolated and selected for resistance to ampicillin (Amp 100). Afterward, the cells were cultured in SOB media with arabinose (1 mM) to induce the Red recombination system, and after they were made electrocompetent, they were electroporated with a PCR product that contained the two genes (pdc and adhB) in tandem flanked by regions homologous to the pflB gene. The primers designed to amplify this PCR product were 4512 FWF (SEQ ID NO: 23) and 4513 RVF (SEQ ID NO: 24). These primers, along with the purified pLOI510 plasmid, were used to generate a PCR product that amplified the two pLOI510 plasmid genes in tandem (pdc and adhB). These primers included the homologous sequences immediately before and after the pflB gene of E. coli MS01 that were used as sequences to conduct the double homologous recombination mediated by the Red recombination system of pKD46. Thus, the pdc and adhB genes were inserted under the pflB promoter in the MS01 strain. The PCR product digested with DpnI and purified with agarose (1%) gel electrophoresis is shown in FIG. 34.

The PCR product was transformed into strain MS01 (pKD46) by electroporation, and the cells were allowed to recover immediately afterward in SOC media (1 mL) for 12 h at 30 and 37° C., as the cells previously recovered at 37° C. for 2 h did not yield any colonies. Thus, future samples were incubated in anaerobic conditions and without shaking for a longer time at these two temperatures so that only the cells that had assimilated the pdc and adhB could be selected and grown. After 12 h of incubation at 30 and 37° C., 200 μL of each culture was inoculated in mineral medium with glucose (20 g/L) and Km 40 and incubated at 37° C. for 48 h in aerobic conditions to isolate colonies that had assimilated the pdc and adhB genes. Only the transformed cells would be capable of growing in anaerobic conditions because they would have a new pathway to regenerate reducing power (NAD$^+$) and to survive under such conditions. After 48 h of incubation, several colonies were recovered, mainly those that had been incubated at 30° C. in SOC media; however, after isolating them and reseeding them in the same medium in anaerobic conditions, they grew much faster.

Figure 35:
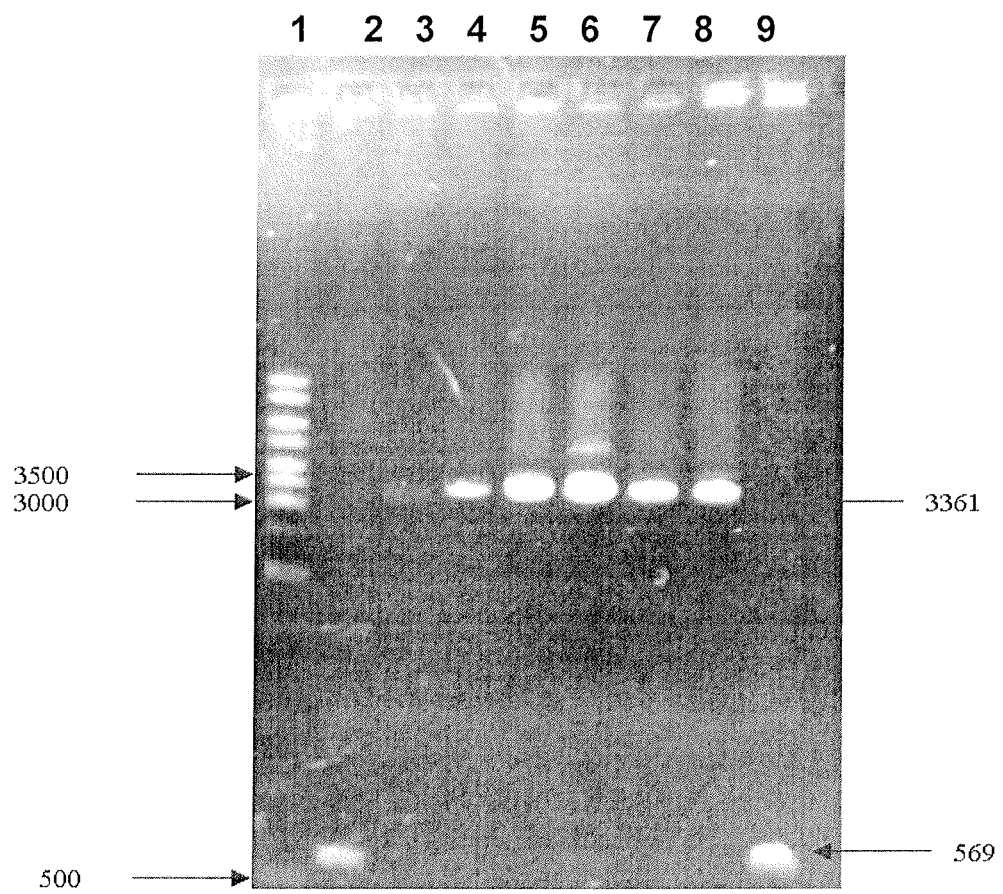
FIG. 35. Image that shows an agarose gel with a PCR product with oligonucleotides 250 bp up and downstream of pflB gen. Lane 1: molecular weight marker (size in bp), Lanes 2 and 9: control strain MS01; 569 pb, and lanes 3-8: PCR product resulting of the integration of pdc and adhB genes from *Z. mobilis* under the promoter of pflB: 3361 bp.

In this way, three colonies were selected for PCR analysis, along with the control strain MS01, using the primers 4166 FWF and 4167 RVF, which amplify a region 250 bp before and after pf/B, yielding PCR products of 3,361 bp for the strains transformed with Z. Mobilis pdc and adhB genes and 569 bp for the control strain MS01, which has suppression of pflB (FIG. 35).

Once the insertion of the pdc and adhB genes in the colonies had been determined phenotypically by growth in anaerobic conditions and genotypically by PCR, this strain was labeled as E. coli MS02 (ΔpflB, ΔadhE, Δfrd, ΔxilFGH:: Km$^R$, ΔIdhA, PpflB::pdc$_{Zm}$-adhB$_{Zm}$, resistant to acetic acid), (see FIG. 41) which produces ethanol, in contrast to strain MS01.

Figure 36:
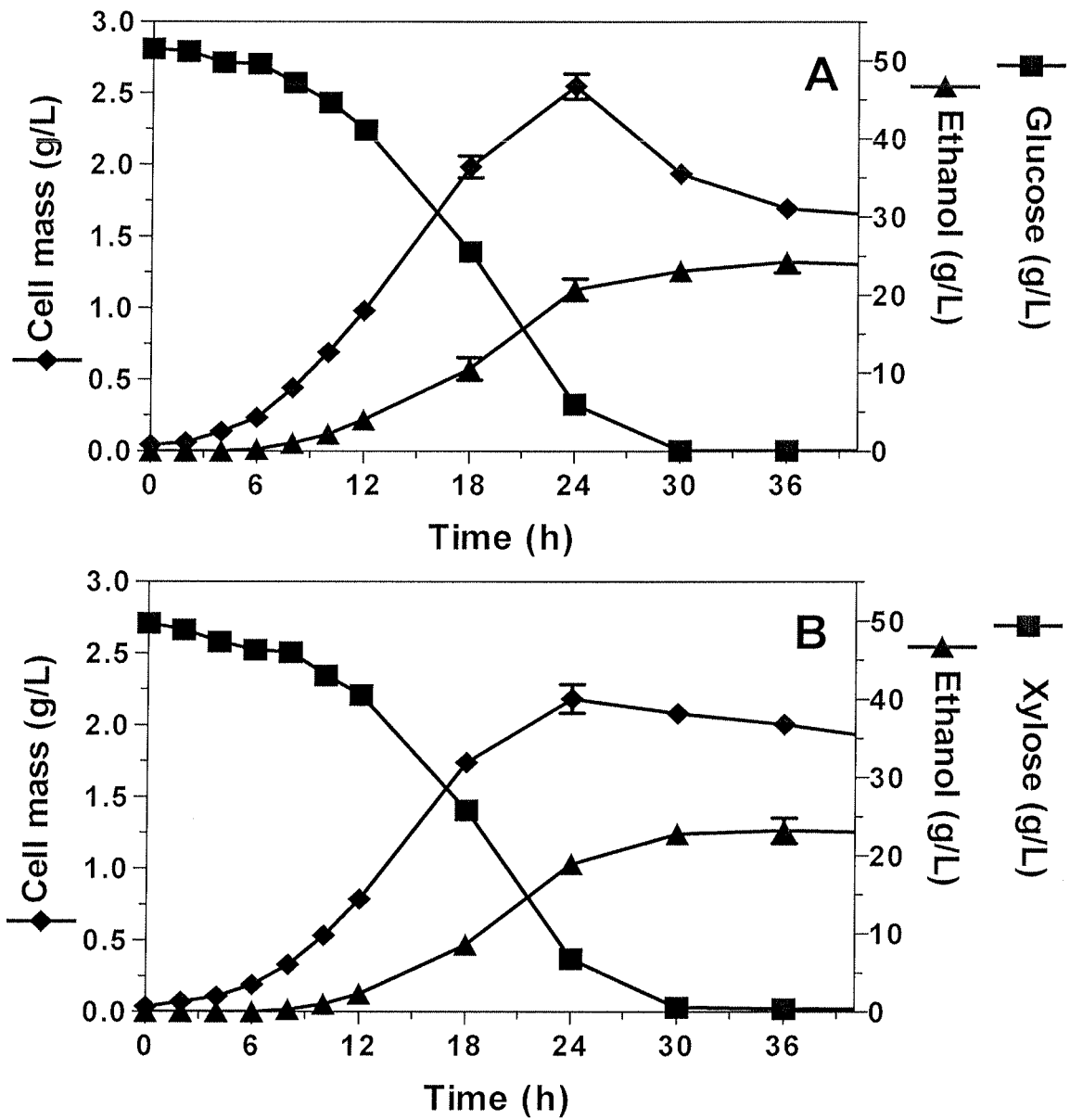
FIG. 36. Graphic that shows the fermentation kinetics of the strain *E. coli* MS01 in AM2 medium with A) glucose and B) xylose (50 g/L), all of them with acetate (2.05 g/L)
Figure 37:
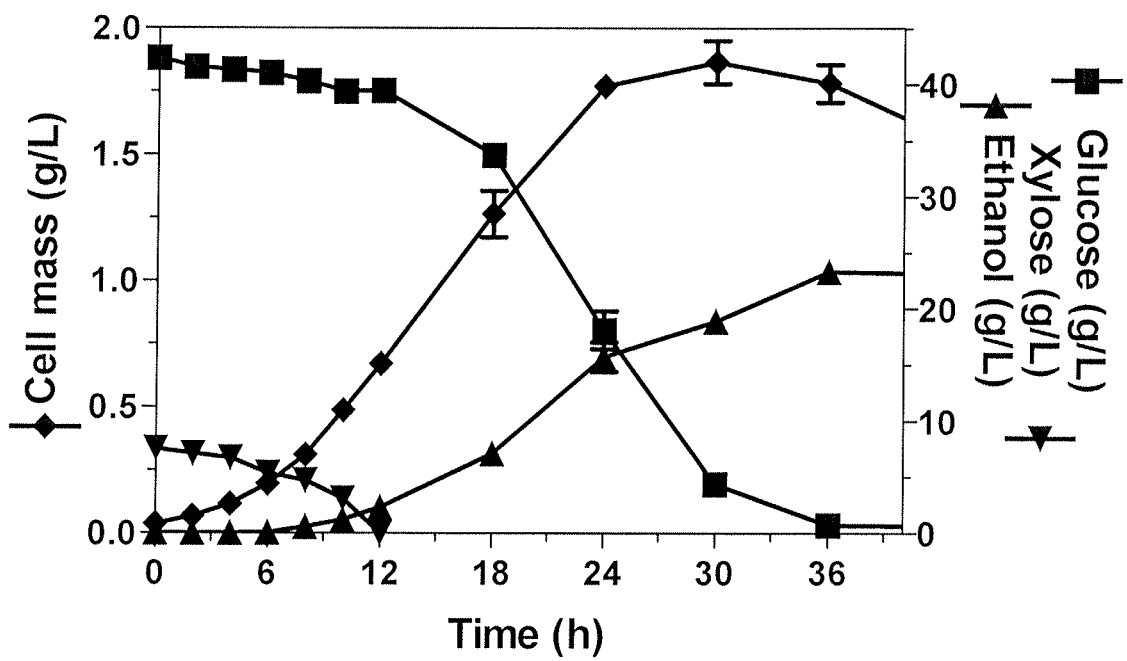
FIG. 37. Graphic that shows the fermentation kinetics of the strain *E. coli* MS04 in AM2 medium with glucose-xylose mixture (7.5-42.5 g/L) and acetate (2.05 g/L).

Subsequently, the E. coli strain MS02 was subjected to a process of adaptive evolution in AM2 mineral medium with glucose or xylose (50 g/L) supplemented with sodium acetate (2.05 g/L), with several passages performed when the cells were in the exponential growth phase. The strain obtained after the process of adaptive evolution was labeled E. coli MS04, and this strain was able to grow in glucose and xylose in the presence of acetic acid, producing ethanol (See FIGS. 36 and 37).

Kinetic Parameters of E. coli MS01 Strain in AM2 Medium with Glucose, Xylose (50 g/L) or a Glucose-Xylose Mixture (7.5-42.5) All of Them with Acetate (2.05 g/L).

| Parameter (exponential growth phase) | E. coli MS04 - Glucose | E. coli MS04 - Xylose | E. coli MS04 - Glucose-Xylose |
|---|---|---|---|
| μ (h$^{-1}$) | 0.3 | 0.26 | 0.25 |
| qs (gsubst/gcel mass h) | 3 | 3.3 | 2.85 |
| qp (gEtOH/gcel mass h) | 1.1 | 0.6 | 0.7 |
| Yps (% Theor. max.) | 92 | 92 | 93 |
| Vol. Prod (gEtOH/L h) | 0.67 | 0.65 | 0.65 |

Example 15

Ethanol Production from Rapid-Growth Grass Hydrolysates Using the Strain *E. coli* MS04 Derived from JU15

The inventors of the present invention conducted ethanol production using strain *E. coli* MS04 (NRRL B-50138), which was derived from *E. coli* JU15 (NRRL B-50140), using sugars from the thermochemical hydrolysis of the rapid-growth grass *Paspalum fasciculatum*. This grass grows naturally in several regions in southeast Mexico and has not been previously reported for use in the production of ethanol. Other rapid-growth grasses, such as elephant grass or switchgrass, have been proposed in the United States and in several countries of the European Union as raw materials to hydrolyze and to generate sugars that can be fermented into ethanol. However, no experiments have been conducted in Latin America to use rapid-growth grass in the production of second-generation ethanol.

Figure 42:
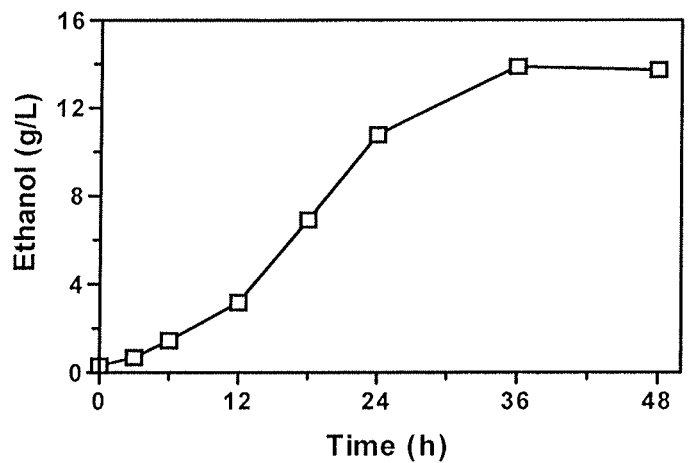
FIG. 42. Ethanol production kinetics using hydrolysate syrups from the grass *Paspalum fasciculatum*.

In this invention, grass collected from the Tabasco region was dried in sunlight. The material was characterized as having 15-25% xylan, 30-40% glucan, 2-3% arabinan, 2.5-3.5% acetate, 12-16% lignin and 1-3% ashes, with the remainder consisting of extractive material. The hemicellulose fraction of the grass was hydrolyzed via a thermochemical method at 121° C. using sulfuric acid with different concentrations (1, 2 and 4% w/w), times (10, 30 and 60 min) and reaction conditions (3 biomass to liquid ratios, 1:2, 1:5 and 1:10). A syrup was generated to test the fermentation ability of the *E. coli* strain MS04 (NRRL B-50138), which was derived from JU15 (NRRL B-50140). The syrup used had a mean level of 28.8 g/L of sugars, primarily xylose (5.5 g/L glucose, 19.6 g/L xylose and 3.7 g/L arabinose), 6.2 g/L acetate and a small amount of furans. The syrup was treated with calcium hydroxide, neutralized and supplemented with salts to ferment the sugars present within. The cultures were carried out in mini-fermenters with operation volumes of 200 mL at a temperature of 37° C. and a pH of 7, with the last value controlled by the automatic addition of 2 N KOH. FIG. 42 shows the results of the ethanol production; this example had a yield of 95% of the theoretical value for the sugar-to-ethanol conversion, converting practically all of the sugars into ethanol in 36 h.

Example 16

Ethanol Production from Agave Bagasse Hydrolysates Using the *E. coli* MS04 Strain Derived from JU15

The inventors of the present invention carried out the production of ethanol using the *E. coli* strain MS04 (NRRL B-50138), which was derived from *E. coli* JU15 (NRRL B-50140), using sugars from the thermochemical hydrolysis of agave bagasse obtained from blue agave distillate production plants. Agave bagasse is a factory waste product of tequila, mezcal and other spirits distilled in several regions of Mexico and now in other Latin American and African countries. This material is essentially lignocellulose and does not have any practical applications in distillation factories because it cannot be used as fuel, and it is a potential alternative source of five- and six-carbon sugars that can be fermented by the microorganisms that are the focus of the present invention patent.

Figure 43:
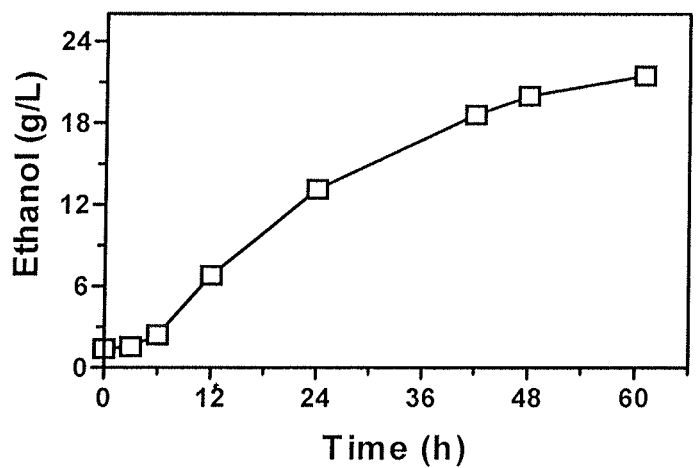
FIG. 43. Ethanol production kinetics using hydrolysate syrups from agave bagasse (*Agave tequilana*).

Blue agave bagasse, collected from an agave distillate factory in the southern region of Morelos, Mexico, was dried in sunlight. The material was characterized as having 12-18% xylan, 35-45% glucan, 3-5% acetate, 22-30% lignin and 2,5-5.5% of ashes, with the remainder consisting of extractive material. The hemicellulose fraction of the agave bagasse was hydrolyzed via a thermochemical method using sulfuric acid at different concentrations and reaction conditions. The syrup was treated with calcium hydroxide, neutralized and supplemented with salts to ferment the sugars present within. A syrup rich in xylose that also contained glucose and arabinose was generated, which was concentrated until a level 51 g/L of total sugars was obtained, including 87.5% xylose, 8.8% glucose and 3.7% arabinose. This syrup also contained 0.2 g/L of hydroxymethyl-furfural, 0.2 g/L of furfural and 20.3 g/L of acetate. The syrup was fermented in a bioreactor with a 1-L operating volume at a temperature of 37° C., with shaking at 360 rpm and a pH of 7 controlled by the automatic addition of 2 N KOH, using the *E. coli* MS04 strain (NRRL B-50138), which was derived from JU15 (NRRL B-50140). The results obtained in this last example of the present invention indicate that the conversion efficiency of the sugars into ethanol was 85% of the theoretical value after 61 h of fermentation; see FIG. 43.

REFERENCES

Bai D. M., Jia M. Z., Zhao X. M., Ban R., Shen F., Li X. G., Xu S. M. 2003. L(+)-lactic acid production by pellet-form *Rhizopus oryzae* R1021 in a stirred tank fermentator. *Chem. Eng. Science*. 58:785-791.

Bailey E. J. 1991. Toward a science of metabolic engineering. *Science*. 252: 1668-1674.

Beall D. S, Ohta K., Ingram L. O. 1991. Parametric studies of ethanol production from xylose and other sugars by recombinant *Escherichia coli. Biotechnol. Bioeng*. 38:296-303.

Böck A., Sawers G. 1996. Fermentation: In *Escherichia coli* and *Salmonella*. Celular and molecular biology. Eds. Neidhardt at al., American Society for Microbiology Press Washington D.C. 1:262-282.

Bungay, H. R. 2004 Confessions of a bioenergy advocate. *Trends Biotechnol*. 22 : 67-71.

Datsenko K. A., Wanner B. L. 2000. One-step inactivation of chromosomal genes in *Escherichia coli* K-12 using PCR products. *Proc Natl Acad Sci USA*. 97(12):6640-5.

Dien B. S., Nichols N. N., Bothast R. J. 2001. Recombinant Escherichia coli engineered for production of L-lactic acid from hexose and pentose sugars. *J. Ind. Microbiol. Biotechnol*. 27:259-264.

Dien B. S., Nichols N. N., Bothast R. J. 2002. Fermentation of sugar mixture using *Escherichia coli* catabolite repression mutants engineered for production of L-lactic acid. *J. Ind. Microbiol. Biotechnol*. 29:221-227.

Dien B. S., Cotta M. A., Jeffries T. W. (2003) Bacteria engineered for fuel ethanol production: Current status. *Appl. Microbiol. Biotechnol*. 63: 258-266

Gonzalez R., Tao, H., Shanmugam K. T., York S. W., Ingram L. O. (2002) Global gene expression differences associated with changes in glycolytic flux and growth rate in *Escherichia coli* during the fermentation of glucose and xilose. *Biothechnol. Prog.* 18: 6-20.

Hahn-Hagerdal B., Jeppsson H., Mohagheghi A. (1994) An interlaboratory comparison of the performance of etanol-producing micro-organisms in a xylose-rich acid hydrolysate. *Appl. Microbiol. Biotechnol.* 41: 62-72.

Hasona A., Kim Y., Healy F. G., Ingram L. O., Shanmugam K. T. 2004. Pyruvate formate lyase and acetate kinase are essential for anaerobic growth of *Escherichia coli* on xylose. *Journal of Bacteriology* 186(22):7593-7600

Hayashi K., Morooka N., Yamamoto Y., Fujita K., K Isono K., Choi S., Eiichi Ohtsubo E., Baba T., Wanner B. L., Mori H., Horiuch T., 2006 Highly accurate genome sequences of *Escherichia coli* K-12 strains MG1655 and W3110. *Molec Syst Biol* 2006.0007

Hernández-Montalvo V., Valle F., Bolívar F., Gosset G. 2001. Characterization of sugar mixtures utilization by an *Escherichia coli* mutant devoid of the phosphotransferase system. *Appl. Microbiol Biotechonol.* 57:186-191.

John R. P., Nampoothiri K. M., Pandey A. 2007. Fermentative production of lactic acid from biomass: an overview on process developments and future perspectives. *Applied Microbio/Biotechnol*. Springer-Verlag 2007.

Lara A. R., Vazquez-Límon C.,Gosset G., López-Munguía A., Ramirez O. T. 2006. Engineering *Escherichia coli* to improve culture performance and reduce formation of By-Product during recombinant protein production under transient intermittent anaerobic conditions. *Biotech Bioeng.* 94(6):1164-1175

Lawford H. G., Rousseau J. D. 1992. Effect of acetic acid on xylose conversion to ethanol by genetically engineered *E. coli*. *Appl. Biochem. Biotechnol.* 34(5):185-204.

Lawford H. G., Rousseau J. D. (1996) The relationship between growth enhancement and pet expression in *Escherichia coli*. *Appl. Biochem. Biotechnol.* 57-58:277-92.

Lawford H. G., Rousseau J. D. (1997) Fermentation of biomass-derived glucuronic acid by pet expressing recombinants of *E. coli* B. *Appl. Biochem. Biotechnol.* 63-65: 221-41

Lin E. C. C, 1996. Dissimilatory pathways for sugars polyols, and carboxylates, *Escherichia coli* and *Salmonella*. Cellular and molecular biology. Eds. Neidhardt et al., American Society for Microbiology. Press Washington D.C. 307-342

Linton, K. J., Higgins C. F., 1998 The *Escherichia coli* ATP-binding cassette (ABC) proteins. *Mol. Microbiol.* 28: 5-13

Martinez A., Grabar T. B., Shanmugam K. T., Yomano L. P., York S. W., Ingram L.O. 2007. Low salt medium for lactate and ethanol production by recombinant *Escherichia coli* B. *Biotechnol. Lett.* 29:397-404

Mielenz J. R. 2001. Etanol producction from biomass: technology and commercialization status. *Current Opinion Microbiol.* 4: 324-329

Narayanan N., Roychoudhury P. K., Srivastava A. 2004. L(+) lactic acid fermentation and its product polymerization. *Electronic J. Biotechnol.* 7(2):167-179.

Nuting G. C., 1970. The byproducts of Milk, *Byproducts of Milk Webb* B. H. y Whitter E. O. (Comps.) Westport, Avi Pub. Co. pp 1-23.

Ohta K., Beall D. S., Mejia J. P., Shanmugam K. T., Ingram L. O. 1991 Genetic improvement of *Escherichia coli* for ethanol production: Chromosomal integration of *Zymomonas mobilis* genes encoding piruvate decarboxylase and alcohol dehydrogenase II. *Appl. Environ. Microbiol.* 57(4): 893-900.

Saha, B. C. 2003. Hemicellulose conversion. *Ind. Microbiol. Biotechnol.* 30: 279-291.

Skory C. D. 2003. Lactic acid production by *Saccharomyces cerevisiae* expressing a *Rhizopus oryzae* lactate deshydrogenase gene. *J. Ind. Microbiol. Biotechnol.* 30: 22-27.

Stephanopoulos G. 1999. Metabolic fluxes and metabolic engineering. *Metab Eng.* 1:1-11.

Sun Y., Cheng J. 2002. Hydrolysis of lignocellulosic materials for etanol production: a review. *Bioresource Technol.* 83:1-11.

Utrilla J., Gosset G., Martinez A. 2009. ATP limitation in pyruvate formate lyase mutant of *Escherichia coli* MG1655 increases glycolytic flux to D-lactate. J. Ind. Microbiol. Biotechnol. 36:1057-1062.

US 2007/ 0037265A1 Zhou S., Ingram L. O., Shanmugam T., Yomano L., Grabar T. B., Moore J. C. Materials and methods for efficient lactic acid production.

Vazquez-Limon C., Vega-Badillo J.,Martinez A., Espinosa-Molina G., Gosset G., Soberón X., López-Munguia A., Osuna J. 2007 Growth rate of a non-fermentative *Escherichia coli* strain is influenced by $NAD^+$ regeneration. *Biotechnol Lett.* 29: 1857-1863.

Zhou S., Caussey T. B., Hasona A., Shanmugan K. T., Ingram L. O. 2003a. Production of optically pure D-lactic acid in mineral salts medium by metabolically engineered *Escherichia coli* W3110. *Applied and Environmental Microbiology* 69(1):399-407.

Zhou S., Shanmugam K. T., Ingram L. O. 2003b. Functional replacement of the *Escherichia coli* D(-)-Lactate Dehydrogenase gene (IdhA) whit the L-(+)-Lactate Dehydrogenase gene (IdhL) from *Pediococcus acidilactici*. Appl. Environ. Microbiol. 69:2237-2244.

Zhou S., Grabar T. B., Shanmugam K. T., Ingram L. O. 2006a. Betaine tripled the volumetric productivity of D(-)-lactate by *Escherichia coli* strain SZ132 in mineral salts medium. *Biotechnol Lett.* 28:671-676.

Zhou S., Shanmugam K. T., Yomano L. P., Grabar T. B., Ingram L. O. 2006b Fermentation of 12% (w/v) glucose to 1.2 M lactate by Escherichia coli strain SZ194 using mineral salts medium. *Biotechnol Lett* 28: 663-670.

Zhou S., Yomano L. P., Shanmugam K. T. Ingram L. O. 2005. Fermentation of 10% (w/v) sugar to D-Lactate by engineered *Escherichia coli* B. *Biotechnol Lett* 27: 1891-1896

Zhou S. Iverson A. G Grayburn W. S. 2008 Engineering a native homoethanol pathway in *Escherichia coli* B for ethanol production. *Biotechnol Lett.* 30:335-342

Zhu J., and Shimizu, K. 2004. The effect of pfl gene knockout on the metabolism for optically pure D-Lactate production by *Escherichia coli*. *App. Microbiol Biotechnol.* 64:367-375.

Zhu Y., Eiteman M. A., DeWitt K., Altman E. 2007. Homolactate fermentation by metabolically engineered *Escherichia coli* strains. *Appl. Environ. Microbiol.* 73(2):456-464.

The invention claimed is:

1. An *Escherichia coli* strain deposited in Agricultural Research Culture Collection (NRRL) under the accession number selected from the group consisting of NRRL B-50140, NRRL B-50137, NRRL B-50139 and NRRL B-50138.

2. The *E. coli* strain of claim 1, wherein the strain has the accession number NRRL B-50140.

3. The *E. coli* strain of claim 1, wherein the strain has the accession number NRRL B-50137.

4. The *E. coli* strain of claim 1, wherein the strain has the accession number NRRL B-50139.

5. The *E. coli* strain of claim 1, wherein the strain has accession number NRRL B-50138.

6. A method to produce D-lactic acid comprising the steps of:
   a) culturing the *E. coli* strain of claim 1 in a suitable medium that contains one or more of the carbon sources selected from the group consisting of xylose, arabinose, glucose, hydrolyzed lignocelluloses and milk whey, wherein the *E. coli* strain has the accession number NRRL B-50140 or NRRL B-50137;
   b) optionally, the recovery of the D-lactic acid; and
   c) optionally, the subsequent purification of the D-lactic acid.

7. A method to produce L-lactic acid comprising the steps of:
   a) culturing the E. coli strain of claim 1 in a suitable medium that contains one or more of the carbon sources selected from the group consisting of xylose, arabinose, glucose, hydrolyzed lignocelluloses and milk whey, wherein the *E. coli* strain has the accession number NRRL B-50139;
   b) optionally, the recovery of the L-lactic acid; and
   c) optionally, the subsequent purification of the L-lactic acid.

8. A method to produce ethanol comprising the steps of:
   a) culturing the *E. coli* strain of claim 1 in a suitable medium that contains one or more of the carbon sources selected from the group consisting of xylose, arabinose, glucose, hydrolyzed lignocelluloses and milk whey, wherein the *E. coli* strain has the accession number NRRL B-50138;
   b) optionally, the recovery of the ethanol; and
   c) optionally, the subsequent purification of the ethanol.

* * * * *